United States Patent
Nanjundan et al.

(10) Patent No.: US 8,211,646 B1
(45) Date of Patent: Jul. 3, 2012

(54) METHODS OF TREATING OVARIAN CANCER BY MODULATING SNON

(75) Inventors: Meera Nanjundan, Tampa, FL (US); Gordon Mills, Houston, TX (US); Dawn Smith, Polk City, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/619,345

(22) Filed: Nov. 16, 2009

Related U.S. Application Data

(60) Provisional application No. 61/114,728, filed on Nov. 14, 2008.

(51) Int. Cl.
*C12Q 1/68* (2006.01)
(52) U.S. Cl. .................................................. 435/6.14
(58) Field of Classification Search .................. None
See application file for complete search history.

(56) References Cited

OTHER PUBLICATIONS

Baldwin et al, Cancer Res. 63: 143 (2003).*
Braig et al, Cancer Res. 66 (6), 2881 (2006).*
Buess et al, Neoplasia 6 (3), 207 (2004).*
Chen, Annals N.Y. Acad. Sci. 908 (1), 111 (2000).*
Chen et al, Cancer Res. 61: 4679 (2001).*
Chia et al, BMC Cancer 6: 252 (2006).*
Coates, J. Pathol. 196: 371 (2002).*
Dellaire et al, BioEssays 26.9, 963 (2004).*
Eder et al, Proc. Natl. Acad. Sci. USA. 102 (35), 12519 (2005).*
Edmiston et al, Cancer Res. 65: 4782 (2005).*
Efeyan et al, Oncogene 26: 1645 (2007).*
Elliott et al, J. Clin. Oncol. 23 (9), 2078 (2005).*
Fukuchi et al, Int. J. Cancer 108: 818 (2004).*
He et al, J. Biol. Chem. 278 (33), 30540 (2003).*
Hsu et al, J. Biol. Chem. 281 (44), 33008 (2006).*
Imoto et al, Cancer Res. 63: 5691 (2003).*
Krakowski et al, Proc. Natl. Acad. Sci. USA. 102 (35), 12437 (2005).*
Kuhn et al, Br. J. Cancer 79 (11/12), 1746 (1999).*
Kutz et al, J. Cell Sci. 114: 3905 (2001).*
Levy et al, Mol. Cell. Biol. 27 (17), 6068 (2007).*
Michaloglou et al, Nature 436: 720 (2005).*
Muller et al, Oncogene 23: 1998 (2004).*
Nagano et al, J. Biol. Chem. 282 (28), 20492 (2007).*
Reed et al, Cancer & Metastasis Reviews 24: 265 (2005).*
Roninson, Cancer Res. 63: 2705 (2003).*
Sarkar et al, J. Biol. Chem. 280 (13), 13037 (2005).*
Sattler et al, The Prostate 39: 79 (1999).*
Sattler et al, The Prostate 45: 207 (2000).*
Shinagawa et al, Oncogene 20: 8100 (2001).*
Stroschein et al, Science 286: 771 (1999).*
Stroschein et al, Genes & Devel. 15: 2822 (2001).*
Sugita et al, Cancer Genet. Cytogenet. 117: 9 (2000).*
Sunde et al, Cancer Res. 66: 8404 (2006).*
Trost et al, Cancer Res. 65: 840 (2005).*
Weber-Mangal et al, Int. J. Cancer 107: 583 (2003).*
Wessels et al, Cancer Res. 62: 7110 (2002).*
Whitley et al, Exptl. Cell Res. 296: 151 (2004).*
Zhang et al, FEBS Lett. 527: 58 (2002).*
Zhang et al, Cancer Res. 63: 5005 (2003).*
Zhang et al, Genes & Dev. 18: 3028 (2004).*
Zhu et al, Mol. Cell. Biol. 25 (24), 10731 (2005).*
Zhu et al, Mol. Cell. Biol. 27 (1), 324 (2007).*
Zhang et al, Oncogene 20: 7146 (2001).*
Bornstein et al, Gynecologic Oncology 99: 726 (2005).*
Kong et al, Int. J. Gynecological Cancer 15: 872 (2005).*
Uslu et al, Clin. Cancer Res. 6: 4957 (2000).*
Shackelford et al, Cancer Res. 66: 11360 (2006).*
Hurteau et al, Cancer 74 (1), 93 (1994).*
Imoto et al, Biochem. Biophys. Res. Comm. 286: 559 (2001).*
Pelicano, H. et al. 2006. "Targeting Hsp90 by 17-AAG in Leukemia Cells: Mechanisms for Synergistic and Antagonistic Drug Combinations with Arsenic Trioxide and Ara-C." Leukemia. vol. 20. pp. 610-619.
Wetzler, M. et al. 2007. "Synergism Between Arsenic Trioxide and Heat Shock Protein 90 Inhibitors on Signal Transducer and Activator of Transcription Protein 3 Activity-Pharmacodynamic Drug-Drug Interaction Modeling." Clin. Cancer Res. vol. 13. No. 7. pp. 2261-2270.
Wrighton, K. H. et al. 2008. "Critical Regulation of TGFbeta Signaling by Hsp90." Proc. Natl. Acad. Sci. USA. vol. 105. No. 27. pp. 9244-9249.
Kilbey, A. et al. 1998. "Evi-1 ZF1 DNA Binding Activity and a Second Distinct Transcriptional Repressor Region are Both Required for Optimal Transformation of Rat1 Fibroblasts." Oncogene. vol. 16. pp. 2287-2291.
Kajino, T. et al. 2007. "TAK1 MAPK Kinase Kinase Mediates Transforming Growth Factor-Beta Signaling by Targeting SnoN Oncoprotein for Degradation." J. Biol. Chem. vol. 282. No. 13. pp. 9475-9481.
Conery, A. R. et al. 2004. "Akt Interacts Directly with Smad3 to Regulate the Sensitivity to TGF-Beta-Induced Apoptosis." Nat. Cell. Biol. vol. 6. No. 4. pp. 366-372.
Pettersson, H. M. et al. 2009. "Arsenic Trioxide is Highly Cytotoxic to Small Cell Lung Carcinoma Cells." Mol. Cancer Ther. vol. 8 No. 1. pp. 160-170.
Du, C. W. et al. 2006. "Arsenic Trioxide Reduces the Invasive and Metastatic Properties of Nasopharyngeal Carcinoma Cells in vitro." Braz. J. Med. Bio. Res. vol. 39. No. 5. pp. 677-685.

(Continued)

*Primary Examiner* — James Martinell
(74) *Attorney, Agent, or Firm* — Robert Varkonyi; Smith & Hopen, P.A.

(57) ABSTRACT

Genomic analysis of ovarian cancers demonstrated a regional chromosomal increase in expression and gene duplication. TGF-β stimulation indicated a link between SnoN RNA and TGF-β. In TIOSE, SnoN protein levels were reduced 15 min post TGF-β-stimulation, likely by proteosome-mediated degradation. SnoN inhibition decreased cell growth between 20 and 50% concurrent with increased p21 levels. Stable expression of SnoN led to growth arrest through induction of senescence. Collectively, these results implicate SnoN levels in multiple roles during ovarian carcinogenesis: promoting cellular proliferation in ovarian cancer cells and as a positive mediator of cell cycle arrest and senescence in non-transformed ovarian epithelial cells.

12 Claims, 38 Drawing Sheets

OTHER PUBLICATIONS

Park, M. et al. 2005. "Arsenic Trioxide (As2O3) Inhibits Invasion of HT1080 Human Fibrosarcoma Cells: Role of Nuclear Factor-KappaB and Reactive Oxygen Species." J. Cell. Biochem. vol. 95. pp. 955-969.

Trachootham, D. et al. 2009. "Targeting Cancer Cells by ROS-Mediated Mechanisms: a Radical Therapeutic Approach?" Nat. Rev. Drug Discov. vol. 8. pp. 579-591.

Davison, K. et al. 2003. "Glutathione Depletion Overcomes Resistance to Arsenic Trioxide in Arsenic-Resistant Cell Lines." Leukemia. vol. 17. pp. 931-940.

Salerno, M. et al. 2002. "The MRP1-Mediated Effluxes of Arsenic and Antimony Do Not Require Arsenic-Glutathione and Antimony-Glutathione Complex Formation." Journal of Bioenergetics and Biomembranes. vol. 34. No. 2. pp. 135-145.

Soo, E.T., et al. 2008. "Heat Shock Proteins as Novel Therapeutic Targets in Cancer." In Vivo. vol. 22. pp. 311-316.

White, E. 2008. "Autophagic Cell Death Unraveled Pharmacological Inhibition of Apoptosis and Autophagy Enables Necrosis." Autophagy. vol. 4. No. 4. pp. 399-401.

Shayesteh, L. et al. 1999. "PIK3CA is Implicated as an Oncogene in Ovarian Cancer." Nat. Genet. vol. 21. pp. 99-102.

Meng, Q. et al. 2006. "Role of PI3K and AKT Specific Isoforms in Ovarian Cancer Cell Migration, Invasion and Proliferation Through the p70S6K1 Pathway." Cell. Signal. vol. 18. pp. 2262-2271.

Ramos, A. M. et al. 2005. "Pharmacologic Inhibitors of PI3K/Akt Potentiate the Apoptotic Action of the Antileukemic Drug Arsenic Trioxide Via Glutathione Depletion and Increased Peroxide Accumulation in Myeloid Leukemia Cells." Blood. vol. 105. pp. 4013-4020.

Liu, X. et al. 2001. "Ski/Sno and TGF-Beta Signaling." Cytokine and Growth Factor Reviews. vol. 12. pp. 1-8.

Kanzawa, T. et al. 2003. "Induction of Autophagic Cell Death in Malignant Glioma Cells by Arsenic Trioxide." Cancer Res. vol. 63. pp. 2103-2108.

Scherz-Shouval, R. et al. 2007. "Oxidation as a Post-Translational Modification that Regulates Autophagy." Autophagy. vol. 3. No. 4. pp. 371-373.

Yatsula, B. et al. 2005. "Identification of Binding Sites of EVI1 in Mammalian Cells." J. Biol. Chem. vol. 280. No. 35. Issue of Sep. 2. pp. 30712-30722.

Riazimand, S. H. et al. 2002. "Investigations for Fine Mapping of Amplifications in Chromosome 3q26.3-28 Frequently Occurring in Squamous Cell Carcinomas of the Head and Neck." Oncology. vol. 63. pp. 385-392.

Shinagawa, T. et al. 2000. The sno Gene, Which Encodes a Component of the Histone Deacetylase Complex, Acts as a Tumor Suppressor in Mice. Embo J. vol. 19. No. 10. pp. 2280-2291.

Wang, D. et al. 1999. "Mutation Analysis of the Smad3 Gene in Human Ovarian Cancers." Int. J. Oncol. vol. 15. pp. 949-953.

Wilson, J. J. et al. 2004. "Crystal Structure of the Dachshund Homology Domain of Human SKI." Structure. vol. 12. pp. 785-792.

Zhang, J. et al. 2006. "Arsenic Trioxide (As2O3) Inhibits Peritoneal Invasion of Ovarian Carcinoma Cells in vitro and in vivo." Gynecol. Oncol. vol. 103. pp. 199-206.

Drysdale, M. J. et al. 2006. "Targeting Hsp90 for the Treatment of Cancer." Current Opinion in Drug Discovery & Development. vol. 9. No. 4. pp. 483-495.

Morishita, K. et al. 1990. "Unique Expression of the Human Evi-1 Gene in an Endometrial Carcinoma Cell Line: Sequence of cDNAs and Structure of Alternatively Spliced Transcripts." Oncogene. vol. 5. pp. 963-971.

Cheng, B. et al. 2008. "Arsenic Trioxide Induced the Apoptosis of Laryngeal Cancer via Down-Regulation of Survivin mRNA." Auris. Nasus. Larynx. vol. 35. pp. 95-101.

Han, Y. H. et al. 2008. "Suppression of Arsenic Trioxide-Induced Apoptosis in HeLa Cells by N-Acetylcysteine." Molecules and Cells. vol. 26. pp. 18-25.

Rubinsztein, D. C. et al. 2009. In Search of an "Autophagomometer". Autophagy. vol. 5. No. 5. pp. 585-589.

Wu, Y. C. et al. 2009. "Inhibition of Macroautophagy by bafilomycin A1 Lowers Proliferation and Induces Apoptosis in Colon Cancer Cells." Biochem. Biophys. Res. Commun. vol. 382. pp. 451-456.

Bellacosa, A. et al. 1995. "Molecular Alterations of the AKT2 Oncogene in Ovarian and Breast Carcinomas." Int. J. Cancer. vol. 64. pp. 280-285.

Liu, Z. et al. 2008. "Inhibitory Role of TGIF in the As2O3-Regulated p21 WAF1/CIP1 Expression." Journal of Biomedical Science. vol. 15. pp. 333-342.

Snijders, A. M. et al. 2001. "Assembly of Microarrays for Genome-Wide Measurement of DNA Copy Number." Nat. Genet. vol. 29, 263-264.

Tsutsumi, S. et al. "Extracellular Heat Shock Protein 90: a Role for a Molecular Chaperone in Cell Motility and Cancer Metastasis." Cancer Sci. vol. 98. No. 10. pp. 1536-1539, (2007).

Hoang, B., et al. 2009. Effect of Autophagy on Multiple Myeloma Cell Viability. Mol Cancer Ther. vol. 8. No. 7. pp. 1974-1984.

Garrido, C. et al. 2003. "Spotlight on Heat Shock Proteins HSP27 and HSP70 Potentially Oncogenic Apoptosis Inhibitors." Cell Cycle. vol. 2. No. 6. pp. 579-584.

Nanjundan et al., Overexpression of SnoN/SkiL. Amplified at the 3q26.2 Locus, in Ovarian Cancers: A Role in Ovarian Pathogenesis, Molecular Oncology, 2008, vol. 2, pp. 164-181.

Fears et al., Intergenic Splicing of MDS1 and EVI1 Occurs in Normal Tissues as Well as in Myeloid Leukemia and Produces a New Member of the PR Domain Family, Proc Natl. Acad. Sci. USA, 1996, vol. 93, pp. 1642-1647.

Chelbi-Alix et al., Induction of the PML Protein by Interferons in Normal and APL Cells, Leukemia, 1995, vol. 9, pp. 2027-2033.

Weichert et al., Protein Kinase C Isoform Expression in Ovarian Carcinoma Correlates with Indicators of Poor Prognosis, International Journal of Oncology, 2003, vol. 23, pp. 633-639.

Chen et al., Superoxide is the Major Reactive Oxygen Species Regulating Autophagy, Cell Death and Differentiation, 2009, vol. 16, pp. 1040-1052.

Liu et al., Inhibitory Role of TGIF in the As2O3-Regulated p21WAF1/CIP1 Expression, J. Biomed. Sci., 2008, vol. 15, pp. 333-342.

Nanjundan et al., Amplification of MDS1/EVI1, Located in the 3q26.2 Amplicon, Is Associated with Favorable Patient Prognosis in Ovarian Cancer, Cancer Research, 2007, vol. 67, No. 7, pp. 3074-3084.

Wu et al., Arsenic Trioxide Inhibits Proliferation in K562 Cells by Changing Cell Cycle and Survivin Expression, Journal of Huazhong University of Science and Technology, 2004, vol. 24, No. 4, pp. 342-344.

* cited by examiner

SEQUENCE LISTING

<160> NUMBER OF SEQ ID NOS: 7

<210> SEQ ID NO 1
<211> LENGTH: 25
<212> TYPE: DNA
<213> ORGANISM: artificial

```
<220> FEATURE:
<223> OTHER INFORMATION: EVI1 exon III qPCR forward primer

<400> SEQUENCE: 1
cgaagactat ccccatgaaa ctatg                                          25

<210> SEQ ID NO 2
<211> LENGTH: 22
<212> TYPE: DNA
<213> ORGANISM: artificial
<220> FEATURE:
<223> OTHER INFORMATION: EVI1 exon III qPCR reverse primer

<400> SEQUENCE: 2
tcacagtctt cgcagcgata tt                                             22

<210> SEQ ID NO 3
<211> LENGTH: 14
<212> TYPE: DNA
<213> ORGANISM: artificial
<220> FEATURE:
<223> OTHER INFORMATION: EVI1 exon III qPCR probe

<400> SEQUENCE: 3
tccacgaaga cgga                                                      14

<210> SEQ ID NO 4
<211> LENGTH: 34
<212> TYPE: DNA
<213> ORGANISM: artificial
<220> FEATURE:
<223> OTHER INFORMATION: SnoN RT-PCR forward primer

<400> SEQUENCE: 4
cggaacaagg gccaccatgg aaaacctcca gaca                                34

<210> SEQ ID NO 5
<211> LENGTH: 28
<212> TYPE: DNA
<213> ORGANISM: artificial
<220> FEATURE:
<223> OTHER INFORMATION: SnoN RT-PCR reverse primer

<400> SEQUENCE: 5
caggcctggc gccctattct ttagcagt                                       28

<210> SEQ ID NO 6
<211> LENGTH: 21
<212> TYPE: RNA
<213> ORGANISM: artificial
<220> FEATURE:
<223> OTHER INFORMATION: EVI1 exon VII siRNA custom sequence

<400> SEQUENCE: 6
acuacgucuu ccuuaaauau u                                              21

<210> SEQ ID NO 7
<211> LENGTH: 21
<212> TYPE: RNA
<213> ORGANISM: artificial
<220> FEATURE:
<223> OTHER INFORMATION: TAK1 siRNA custom sequence

<400> SEQUENCE: 7
guagauccau ccaagacuuu u                                              21
```

METHODS OF TREATING OVARIAN CANCER BY MODULATING SNON

CROSS REFERENCE TO RELATED APPLICATION

This application claims priority to pending U.S. Provisional Patent Application No. 61/114,728, entitled "Overexpression of SnoN/SkiL, Amplified at the 3Q26.2 Locus, In Ovarian Cancers: A Role in Ovarian Pathogenesis", filed on Nov. 14, 2008, the contents of which are herein incorporated by reference.

GOVERNMENT SUPPORT STATEMENT

This invention was made with government support under Grant Nos. CA123219-01A2, CA083639, CA16672 and CA64602, awarded by the National Cancer Institute, RO1-CA123219-01A2, awarded by the National Institutes of Health, and DE-AC03-76SF00098, awarded by the Department of Energy. The Government has certain rights in the invention.

FIELD OF INVENTION

This invention relates to cancer therapy. Specifically, the invention is a method of treating cancers, namely ovarian cancer by modulating TGF-β signaling pathway modulators.

BACKGROUND OF THE INVENTION

Ovarian cancer is the 5$^{th}$ most common cancer in women with approximately 23,000 new cases and 15,000 deaths each year in the United States. Although advances in surgery and chemotherapy have improved the survival rate, the development of resistance to chemotherapy continues to represent a challenging clinical problem in the treatment of advanced stage ovarian carcinoma. Thus, greater effort is needed to identify novel therapeutic targets and develop novel treatment strategies. Targeting signaling pathways that are dysregulated in cancer is one approach to improving patient survival. Transforming growth factor-beta (TGFβ) signaling critically regulates development and homeostasis in multiple cell types. TGFβ initiates intracellular signaling by binding to cell surface receptors (TGFβRI and TGFβRII) leading to phosphorylation of SMAD2/3, which bind to SMAD4 and translocates into the nucleus to interact with transcription factors to regulate expression of target genes. TGFβ can also signal through SMAD-independent pathways, including PI3K/AKT (Elliott, & Blobe, 2005. Role of transforming growth factor Beta in human cancer. J Clin Oncol 23, 2078-2093), which is aberrant in ovarian carcinomas. Several TGFβ signaling mediators are altered during ovarian cancer development including ecotropic viral integration site-1 (EVI1) (Nanjundan, et al. 2007. Amplification of MDS1/EVI1 and EVI1, located in the 3q26.2 amplicon, is associated with favorable patient prognosis in ovarian cancer. Cancer Res 67, 3074-3084), and TGFβRII (Sunde, et al. 2006. Expression Profiling Identifies Altered Expression of Genes That Contribute to the Inhibition of Transforming Growth Factor-{beta} Signaling in Ovarian Cancer. Cancer Res 66, 8404-8412). TGFβ mediates both tumor suppressing and tumor promoting activities by repressing transformation in normal cells and increasing aggressiveness of transformed cells through induction of epithelial-mesenchymal transition (EMT) leading to increased invasion and metastases. In ovarian cancers, proposed mechanisms for resistance to TGFβ-mediated growth inhibition include decreased expression of TGFβ receptors, repression by oncoproteins (EVI1 and SnoN), dysregulation of RUNX1 activation, and activation of additional pathways such as PKC (Elliott, & Blobe, 2005. Role of transforming growth factor Beta in human cancer. J Clin Oncol 23, 2078-2093).

Arsenic trioxide ($As_2O_3$), an effective treatment for patients with acute promyelocytic leukemia (APL) (Zhang, et al. 2001. Arsenic trioxide, a therapeutic agent for APL. Oncogene 20, 7146-7153), is active in vitro in several solid tumor cell lines, including ovarian cancer cells (Bornstein, et al. 2005. Arsenic Trioxide inhibits the growth of human ovarian carcinoma cell line. *Gynecol Oncol* 99, 726-729; Kong, et al. 2005. Arsenic trioxide induces apoptosis in cisplatin-sensitive and -resistant ovarian cancer cell lines. Int J Gynecol Cancer 15, 872-877; Uslu, et al. 2000. Arsenic trioxide-mediated cytotoxicity and apoptosis in prostate and ovarian carcinoma cell lines. Clin Cancer Res 6, 4957-4964). In human ovarian carcinoma cell lines, $As_2O_3$ is reported to be highly cytotoxic, inducing apoptosis, necrosis, autophagy, and inhibiting invasion (Bornstein, et al. 2005. Arsenic Trioxide inhibits the growth of human ovarian carcinoma cell line. Gynecol Oncol 99, 726-729; Zhang & Wang. 2006. Arsenic trioxide (As(2)O(3)) inhibits peritoneal invasion of ovarian carcinoma cells in vitro and in vivo. Gynecol Oncol 103, 199-206). The mechanism of action of $As_2O_3$ is presently unclear. Interestingly, in primary murine leukemia cells, $As_2O_3$ (between 2-10 μM) has been shown to degrade EVI1, a well known TGFβ signaling repressor, by the ubiquitin-proteosome pathway, while MDS1 degradation occurs via a proteosome-independent pathway (Shackelford, et al. 2006. Targeted degradation of the AML1/MDS1/EVI1 oncoprotein by arsenic trioxide. Cancer Res 66, 11360-11369). The heat shock protein-90 (HSP90) inhibitor, geldanamycin (17-allylaminogeldanamycin, 17-AAG), which is presently in phase II clinical trials (Tsutsumi & Neckers. 2007. Extracellular heat shock protein 90: a role for a molecular chaperone in cell motility and cancer metastasis. Cancer Sci 98, 1536-1539), is responsible for degrading a number of "client" proteins, including TGFβRI and TGFβRII via the ubiquitin-proteosome pathway. HSP90 directly interacts with TGFβRI and TGFβRII increasing TGFβ receptor degradation by modulating the activity of the E3 ubiquitin ligase SMURF2 (Wrighton, et al. 2008. Critical regulation of TGFbeta signaling by Hsp90. Proc Natl Acad Sci USA 105, 9244-9249). Interestingly, HSP90 is overexpressed in a number of cancers and maintains the conformational stability and function of a number of oncogenic "client" proteins which have been shown to have roles in regulating cellular proliferation, invasion, metastasis, and angiogenesis (Drysdale, et al. 2006. Targeting Hsp90 for the treatment of cancer. Current opinion in drug discovery & development 9, 483-495; Soo, et al. 2008. Heat shock proteins as novel therapeutic targets in cancer. In Vivo 22, 311-315). Dual treatment of arsenic trioxide and geldanamycin has been previously reported to have synergistic functional effects (Pelicano, et al. 2006. Targeting Hsp90 by 17-AAG in leukemia cells: mechanisms for synergistic and antagonistic drug combinations with arsenic trioxide and Ara-C. Leukemia 20, 610-619; Wetzler, et al. 2007. Synergism between arsenic trioxide and heat shock protein 90 inhibitors on signal transducer and activator of transcription protein 3 activity—pharmacodynamic drug-drug interaction modeling. Clin Cancer Res 13, 2261-2270).

TGF-β mediates differential roles depending on the stage of tumorigenesis (Elliott and Blobe, 2005. Role of transforming growth factor Beta in human cancer. J. Clin. Oncol. 23, 2078-2093). During tumor initiation, TGF-β functions as a growth inhibitor increasing apoptosis. In contrast, during tumor progression, TGF-β increases epithelial mesenchymal transition (EMT) increasing invasiveness and metastatic potential leading to a worsened outcome. Although it is clear that TGF-β function is aberrant in ovarian cancer (Hurteau et al., 1994. Transforming growth factorbeta inhibits proliferation of human ovarian cancer cells obtained from ascites. Cancer 74, 93-99) and there are rare mutations in the TGF-β receptors and SMADs in ovarian cancer (Chen et al., 2001. Transforming growth factor-beta receptor type I gene is frequently mutated in ovarian carcinomas. Cancer Res. 61, 4679-4682; Wang et al., 1999. Mutation analysis of the Smad3 gene in human ovarian cancers. Int. J. Oncol. 15, 949-953; Wang et al., 2000. Mutation analysis of the Smad6 and Smad7 gene in human ovarian cancers. Int. J. Oncol 17, 1087-1091), the mechanisms underlying the aberrations in TGF-β function in ovarian cancer remain unclear. Recently, EVI1 as well as DACH1 have been shown to be upregulated in ovarian cancers where both gene products inhibited TGF-β signaling in immortalized normal ovarian epithelial cells. Further, a DACH1 dominant negative partially restored signaling in ovarian cancer cell lines resistant to TGF-β suggesting that these aberrantly expressed genes may be partially responsible for disrupting TGF-β signaling in ovarian cancer (Nanjundan et al., 2007. Amplification of MDS1/EVI1 and EVI1 located in the 3q26.2 amplicon, is associated with favorable patient prognosis in ovarian cancer. Cancer Res. 67, 3074-3084; Sunde et al., 2006. Expression profiling identifies altered expression of genes that contribute to the inhibition of transforming growth factor-{beta} signaling in ovarian cancer. Cancer Res. 66, 8404-8412).

The role of SnoN/SkiL in tumorigenesis is complex. SnoN has been proposed to act as an oncoprotein since its expression is increased in many human tumor cell lines and overexpression results in transformation of fibroblasts (He et al., 2003. The transforming activity of Ski and SnoN is dependent on their ability to repress the activity of Smad proteins. J. Biol. Chem. 278, 30540-30547; Zhu et al., 2005. Requirement for the SnoN oncoprotein in transforming growth factor beta-induced oncogenic transformation of fibroblast cells. Mol. Cell. Biol. 25, 10731-10744). However, contrasting reports have suggested that SnoN may also act as a tumor suppressor. Patients with stage D colorectal carcinomas had decreased expression of SnoN levels particularly in microsatellite unstable cancers perhaps due to a disrupted TGF-β signaling pathway (Chia et al., 2006. SnoN expression is differently regulated in microsatellite unstable compared with microsatellite stable colorectal cancers. BMC Cancer 6, 252). Studies in lung epithelial cells indicated that SnoN acts as a positive mediator of TGF-β-induced transcription and cell cycle arrest (Sarker et al., 2005. SnoN is a cell type specific mediator of transforming growth factor-beta responses. J. Biol. Chem. 280, 13037-13046). Further, although SnoN expression is elevated in lung and breast cancer cell lines and promotes cellular proliferation, it inhibits epithelial- to -mesenchymal transition resulting in decreased metastatic potential in xenografts (Thu et al., 2007. Dual role of SnoN in mammalian tumorigenesis. Mol. Cell. Biol. 27, 324-339). Moreover, heterozygous knockout SnoN mice display increased susceptibility to chemical-induced tumorigenesis (Shinagawa et al., 2000. The sno gene, which encodes a component of the histone deacetylase complex, acts as a tumor suppressor in mice. Embo J. 19, 2280-2291; Shinagawa et al., 2001. Increased susceptibility to tumorigenesis of ski-deficient heterozygous mice. Oncogene 20, 8100-8108). Thus, depending on the cell context and the activity of other intracellular signaling pathways, the activities of SnoN/SkiL may either promote transformation or tumor suppression while inhibiting malignant progression which may contribute to the well-established dual effects of TGF-β in tumor development (Elliott and Blobe, 2005. Role of transforming growth factor Beta in human cancer. J. Clin. Oncol. 23, 2078-2093).

SUMMARY OF THE INVENTION

SnoN was shown to locate at a frequent and localized point of genomic amplification at 3q26.2 in advanced stage serous epithelial ovarian cancers by high-resolution array CGH using a bacterial artificial chromosome (BAC) contig encompassing the q arm of chromosome 3. Further, there is a marked and frequent accumulation of SnoN transcripts in ovarian cancer. Although transient expression of SnoN repressed both the PAI-1 and CAGA promoters as well as the AP-1 reporter in TAg/hTert immortalized normal ovarian epithelial T29 cells (TIOSE), there was little effect on the p21 promoter and cell growth. However, SnoN knockdown using siRNA in both TIOSE and OVCA indicated that SnoN increases cellular proliferation. In contrast, stable expression of SnoN in T29 cells induced growth arrest and senescence in several independent SnoN expressing clones. Thus, although SnoN levels are elevated in ovarian cancers likely contributing to tumor progression, SnoN functions to decrease tumorigenic properties in normal ovarian epithelial cells. Thus, SnoN may contribute to the pro- and anti-tumorigenic properties of TGF-β during tumor initiation and progression.

To further understand the mechanism of drug-induced cell death, the effects of $As_2O_3$ and 17-AAG on TGFβ signaling mediators were examined. In contrast to geldanamycin, arsenic trioxide markedly altered protein levels of EVI1 SnoN, TGFβRII, as well as other key TGFβ signaling mediators, including SMAD2/3 and AKT. EVI1 protein expression was restored following MG132/PS-341 treatment suggesting that $As_2O_3$ induced effects on EVI1 may be regulated through the ubiquitin-proteosome pathway. Functionally, $As_2O_3$ elicited a marked effect on cell growth, migratory potential, autophagy, and apoptosis in a number of ovarian cell lines. The induction of autophagy appears to be a cell survival mechanism whereby SnoN alters cellular sensitivity to apoptosis by modulating LC3-II levels. These results suggest that SnoN could be a potential target for therapy as it promotes cell survival via induction of autophagy.

It was found that administering the compounds of the present invention were effective in treating cancer. As such, a method is presented for the treatment of cancer, comprising administering a first compound, where the first compound is at least one of arsenic trioxide, 17-allylaminogeldanamycin, TGF-β and a salt thereof; along with administering a second compound, where the second compound is 3-methyladenine, bafilomycin A, JNK II inhibitor, LY294002, triciribine, wortmanin, anti-Akt siRNA, dominant negative Akt, anti-SnoN siRNA, dominant negative SnoN, dominant negative DASCH1, dominant negative MRP1, anti-MRP1 siRNA, TGF-βRII, anti-GSH siRNA, or dominant negative GSH. In specific embodiments, the second compound is 3-methyladenine, bafilomycin A, or LY294002, and in more particular embodiments, the second compound is 3-methyladenine is administered at between 0.1 mM and 10 mM; bafilomycin A is administered at between 25 mM and 100 mM; LY294002 is administered at 50 μM; or JNK II inhibitor administered at 25 μM. The first compound may optionally be arsenic trioxide is administered at between 2 μM 50 μM; 17-allylaminogeldanamycin is administered at between 2 μM and 50 μM; or TGF-β is administered at 50 pM.

Also disclosed is a method of treating cancer comprising modulating TGF-β signaling by modulating SnoN expression; and administering a anti-proliferative agent, where the antiproliferative agent is selected from the group consisting of arsenic trioxide, 17-allylaminogeldanamycin, and a salt thereof. In specific embodiments, the SnoN expression is modulated by administering anti-SnoN siRNA, dominant negative SnoN, or exogenous SnoN. More particularly, arsenic trioxide may be administered at between 2 μM 50 μM or 17-allylaminogeldanamycin administered at between 2 μM and 50 μM.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
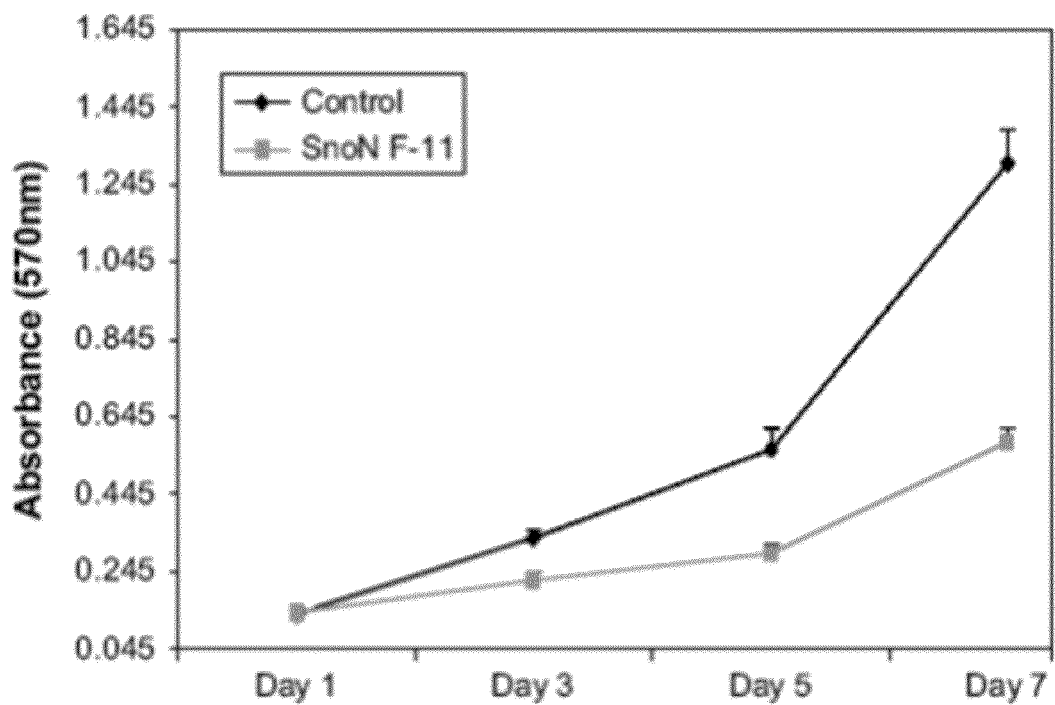
FIG. 1 is a graph showing stable expression of SnoN induces senescence by bypassing cellular immortalization in Tag/hTERT immortalized ovarian TIOSE (T29) cells. Stable overexpression of SnoN-EGFP (clone F-11) in TIOSE cells on proliferation was performed an analyzed in triplicate.

Regions of genomic aberrations frequently harbor important oncogenes and tumor suppressor genes. Amplification of chromosome 3q26 has consistently been found in tumors of the ovary (Eder et al., 2005. Atypical PKCiota contributes to poor prognosis through loss of apical-basal polarity and cyclin E overexpression in ovarian cancer. Proc. Natl. Acad. Sci. USA 102, 12519-12524; Sugita et al., 2000. Molecular definition of a small amplification domain within 3q26 in tumors of cervix, ovary, and lung. Cancer Genet. Cytogenet 117, 9-18; Weichert et al., 2003. Protein kinase C isoform expression in ovarian carcinoma correlates with indicators of poor prognosis. Int. J. Oncol. 23, 633-639), cervix (Sugita et al., 2000. Molecular definition of a small amplification domain within 3q26 in tumors of cervix, ovary, and lung.

Cancer Genet. Cytogenet 117, 9-18), esophagus (Imoto et al., 2001. SNO is a probable target for gene amplification at 3q26 in squamouscell carcinomas of the esophagus. Biochem. Biophys. Res. Commun 286, 559-565; Imoto et al., 2003. Identification of ZASC1 encoding a Kruppel-like zinc finger protein as a novel target for 3q26 amplification in esophageal squamous cell carcinomas. Cancer Res. 63, 5691-5696), breast (basal and BRCA1-associated) (Weber-Mangal et al., 2003. Breast cancer in young women (< or =35 years): genomic aberrations detected by comparative genomic hybridization. Int. J. Cancer 107, 583-592; Wessels et al., 2002. Molecular classification of breast carcinomas by comparative genomic hybridization: a specific somatic genetic profile for BRCA1 tumors. Cancer Res. 62, 7110-7117), lung (Sugita et al., 2000. Molecular definition of a small amplification domain within 3q26 in tumors of cervix, ovary, and lung. Cancer Genet. Cytogenet 117, 9-18), head and neck (Riazimand et al., 2002. Investigations for fine mapping of amplifications in chromosome 3q26.3-28 frequently occurring in squamous cell carcinomas of the head and neck. Oncology 63, 385-392), and prostate (Sattler et al., 1999. Comparative genomic hybridization reveals DNA copy number gains to frequently occur in human prostate cancer. Prostate 39, 79-86; Sattler et al., 2000. Novel amplification unit at chromosome 3q25-q27 in human prostate cancer. Prostate 45, 207-215). In ovarian cancers, it has been demonstrated that the p110a catalytic subunit of PIK3CA (Shayesteh et al., 1999. PIK3CA is implicated as an oncogene in ovarian cancer. Nat. Genet. 21, 99-102) and PKCi (Eder et al., 2005. Atypical PKCiota contributes to poor prognosis through loss of apical-basal polarity and cyclin E overexpression in ovarian cancer. Proc. Natl. Acad. Sci. USA 102, 12519-12524) are functionally deregulated by 3q26 copy number increase. Recent studies indicate that EVI1 and MDS1/EVI1 located at 3q26.2 are also elevated in advanced stage serous epithelial ovarian cancers (Nanjundan et al., 2007. Amplification of MDS1/EVI1 and EVI1 located in the 3q26.2 amplicon, is associated with favorable patient prognosis in ovarian cancer. Cancer Res. 67, 3074-3084). SnoN/SkiL (Imoto et al., 2001. SNO is a probable target for gene amplification at 3q26 in squamouscell carcinomas of the esophagus. Biochem. Biophys. Res. Commun 286, 559-565) and PKCi, which is located adjacent to SnoN, are located in a unique region of genomic amplification independent from those encompassing PIK3CA, EVI1 and MDS1/EVI1. In malignant cells, SnoN expression has been reported to be elevated not only due to gene amplification, but also as a result of increased transcription and protein stability (Buess et al., 2004. Amplification of SKI is a prognostic marker in early colorectal cancer. Neoplasia 6, 207-212; Fukuchi et al., 2004. Increased expression of c-Ski as a co-repressor in transforming growth factor-beta signaling correlates with progression of esophageal squamous cell carcinoma. Int. J. Cancer 108, 818-824; Krakowski et al., 2005. Cytoplasmic SnoN in normal tissues and nonmalignant cells antagonizes TGF-β signaling by sequestration of the Smad proteins. Proc. Natl. Acad. Sci. USA 102, 12437-12442; Reed et al., 2005. SKI pathways inducing progression of human melanoma. Cancer Metastasis Rev. 24, 265-272; Zhang et al., 2003. Ski-related novel protein N (SnoN), a negative controller of transforming growth factor-beta signaling, is a prognostic marker in estrogen receptor-positive breast carcinomas. Cancer Res. 63, 5005-5010; Zhu et al., 2005. Requirement for the SnoN oncoprotein in transforming growth factor beta-induced oncogenic transformation of fibroblast cells. Mol. Cell. Biol. 25, 10731-10744; Zhu et al., 2007. Dual role of SnoN in mammalian tumorigenesis. Mol. Cell. Biol. 27, 324-339).

SnoN is an important negative regulator of TGF-β signaling via its interaction with SMAD proteins (Liu et al., 2001. Ski/Sno and TGF-β signaling. Cytokine Growth Factor Rev. 12, 1-8; Stroschein et al., 1999. Negative feedback regulation of TGF-β signaling by the SnoN oncoprotein. Science 286, 771-774). Elevated SnoN expression may contribute, in some cases, to the resistance of malignant cancer cells to TGF-β-induced growth arrest (Edmiston et al., 2005. Inability of transforming growth factor-beta to cause SnoN degradation leads to resistance to transforming growth factorbeta-induced growth arrest in esophageal cancer cells. Cancer Res. 65, 4782-4788). SnoN/SkiL can interact with SMAD2, SMAD3, and SMAD4 to prevent them from binding to transcriptional coactivators thus leading to repression of target genes and blockade of TGF-β-induced growth arrest (Edmiston et al., 2005. Inability of transforming growth factor-beta to cause SnoN degradation leads to resistance to transforming growth factor beta-induced growth arrest in esophageal cancer cells. Cancer Res. 65, 4782-4788; Stroschein et al., 1999. Negative feedback regulation of TGF-β signaling by the SnoN oncoprotein. Science 286, 771-774; Stroschein et al., 2001. Smad3 recruits the anaphase-promoting complex for ubiquitination and degradation of SnoN. Genes Dev. 15, 2822-2836).

The term "neoplasm" and "neoplastic growth" broadly refers to the development of neurological deficits associated with impaired blood flow to the brain regardless of the cause. The term is intended to include cancers, i.e. diseases caused by any type of tumor including those with the capacity to metastasize with loss of growth control and positional control.

The term "effective amount" or pharmaceutically effective amount" refers to a nontoxic, but significant, amount of the disclosed agent required to provide the desired biological result. The result can be a reduction and/or alleviation of symptoms, causes of disease, or other desired alteration of a biological system. An "effective amount" for therapeutic purposes is the amount of the composition of sigma receptor ligand required to provide a clinically significant decrease in neoplastic growth, such as those resulting from cancer cells. An appropriate effective amount may be determined by one of ordinary skill in the art using routine experimentation.

The term "treat" or "treatment" means a postponement of progression of cancer and/or a reduction in neoplastic growth and/or reduction in the severity of symptoms that have or are expected to develop. The term also is intended to include reducing current neoplastic growth mass, preventing further growth, and ameliorating or preventing the underlying metabolic causes.

The term "patient" includes mammals and non-mammals. Non-limiting examples include humans, non-human primates, species of the family bovidae, species of the family suidae, domestic animals including rabbits, dogs, and cats, laboratory animals, such as rats, mice, guinea pigs, and non-mammals, including birds and fish.

The term "pharmaceutically acceptable salt" means a salt that possesses the desired pharmacological activity of the parent compound. Such salts include, without limiting the scope of the invention, salt derivatives prepared by methods known to those of skill in the art. For example, acid addition salts, formed with inorganic acids, such as hydrochloric acid, hydrobromic acid, sulfuric acid, nitric acid, phosphoric acid, lewis acids, or formed with organic acids, such as acetic acid, propionic acid, hexanoic acid, cyclopentancepropionic acid, glycolica acid, pyruvic acid, lactic acid, malonic acid, succinic acid, malic acid, meleic acid, fumaric acid, and citric acid. Alternatively, the salt derivatives are formed when an acidic poton present in the patent compound is replaced by a metal ion, such as an alkali metal, an alkaline earth ion, or coordinates with an organic base. Some non-limiting exemplary inorganic bases include aluminum hydroxide, calcium hydroxide, potassium hydroxide, sodium carbonate, and sodium hydroxide.

In general, the compounds of the present invention are administered in a therapeutically effective amount by any accepted mode of administration. Suitable dosage ranges depend upon factors known to one skilled in the art. Non-limiting examples of factors include the severity of the disease to be treated, the age of the patient, the relative health of the subject, the potency of the compound utilized, and the route and form of administration. Once of skill in the art will also be capable of ascertaining the therapeutically effective amount of compound needed for a given disease, without undue experimentation and in reliance of his or her experience.

Compound of this invention are administered as pharmaceutical formulations, including those suitable for oral—including buccal and sub-lingual—rectal, nasal, topical, pulmonary, vaginal, or parenteral—including intramuscular, intraarterial, intrathecal, subcutaneous, and intravenous. In some embodiments, intravenous or intraarterial administration is a preferred manner of providing a daily dosing regimen that can be adjusted according to the degree of affliction.

For solid compositions, conventional solid carriers include, without limiting the scope of the invention to any particular material, pharmaceutical grades of mannirol, lactose, starch, magnesium stearate, magnesium carbonate, sodium saccharin, talc, cellulose, glucose, and sucrose. Liquid pharmaceutically administrable compositions can be prepared by dissolving, dispersing, suspending, an active compound of the present invention in an optional pharmaceutical adjuvant or excipient. Non-limiting examples include water, saline, aqueous dextrose, glycerol, ethanol, similar materials, and combinations thereof. If desired, the pharmaceutical composition to be administered may also contain deminimis amounts of nontoxic auxiliary substances, such as wetting or emulsifying agents, pH buffers—such as sodium acetate, sorbitan monolaurate, triethanolamine sodium acetate, triethanolamine oleate. Methods of preparing such substances is known or apparent to one of skill in the art, and described in art-recognized literature, such as Remington's Pharmaceutical Sciences, $18^{th}$ Ed (Easton, Pa.; Mack Publishing Co., 1990).

Parenteral formulations may be prepared using conventional materials, either as liquid solutions or suspensions, solid forms suitable for use in suspension or solublization before injection, or emulsion. Injectable solutions or suspensions using known dispersing or wetting agents are known in the art, and optionally include nontoxic diluents or solvents. Exemplary vehicles include, without limiting the scope of the invention, water, Ringer's solution, isotonic sodium chloride, and phosphate buffered saline. Sterile, fixed oils, fatty esters, and polyols. The parenteral solution or solvent may also include a slow release or sustained release systems, which maintains a constant dosage level. Other variations of administration agents containing compounds of the present invention are known in the art.

Cell Lines and Cell Culture

Ovarian cell lines were utilized in the following studies. T antigen/hTERT immortalized normal ovarian surface epithelial cells (T80), SKOV3 (amplification at the EVI1 locus), HEY (high expressing EVI1 cell line), and OVCA429 (high expressing EVI1 cell line) (Nanjundan, et al. 2007. Amplification of MDS1/EVI1 and EVI1, located in the 3q26.2 amplicon, is associated with favorable patient prognosis in ovarian cancer. Cancer Res 67, 3074-3084). Cell lines were cultured in RPMI 1640 with 8% FBS and penicillin/streptomycin and maintained in an incubator with a humidified atmosphere containing 95% air and 5% $CO_2$ at 37° C.

Preparation of patient samples Stage I-IV serous epithelial ovarian cancers were obtained from the Ovarian Cancer Tumor Bank of the MD Anderson Cancer Center (Houston, Tex.). Benign ovarian tumors and stage III and IV serous epithelial ovarian cancers were obtained from the Basic Biology of Ovarian Cancer Program Project Grant Bank Tissue and Pathology Core at the University of California San Francisco. Normal ovarian epithelial scrapings were obtained from Northwestern University. The normal scrapings were collected using a cytobrush, and the cells were immediately suspended and frozen in RLT buffer (Qiagen, Valencia, Calif.). Benign ovarian cysts were macrodissected to increase the amount of epithelium present. All cancer samples were selected to contain greater than 70% tumors. Where necessary, early stage and late stage ovarian cancers were macrodissected to contain greater than 70% tumor. DNA was extracted as previously described (Snijders et al., 2001. Assembly of microarrays for genome-wide measurement of DNA copy number. Nat. Genet. 29, 263-264). Total RNA was extracted from all ovarian cancers and normal ovarian epithelial scrapings using the RNeasy Kit (Qiagen, Valencia, Calif.) according to the manufacturer's protocol. Institutional Review Board approval had been obtained at each participating institution prior to the initiation of this study.

Quantitative PCR Analysis

RNA was isolated using the RNeasy Mini Kit (Qiagen, Valencia, Calif.) from normal, benign, stage I-IV ovarian patient samples and quantitative PCR was performed. A one-step RT-PCR Taqman master mix from Applied Biosystems (Foster City, Calif.) and primers for genes in the 3q26.2 amplicon were obtained using Genebank sequences as well as from Assays on Demand (Hs00180524_m1 (SnoN/SkiL)), with the following primers and probe sets.

EVI1 Exon III—(detects both EVI1 and MDS1/EVI1):
SEQ ID 1: Forward primer, CGAAGACTATCCCCATGAAACTATG;
SEQ ID 2: Reverse primer, TCACAGTCTTCGCAGCGATATT;
SEQ ID 3: Probe sequence, TCCACGAAGACGGA.

Primers/probe sequences for SnoN (Hs00180524_m1), TGFβRII (Hs00234253_m1), and LC3 (Hs00261291_m1) were obtained from Applied Biosystems (Assays by Design).

mRNA levels were determined using the One-Step-Plus Applied Biosystems Detection System or ABI PRISM 7700 Sequence Detection System using β-actin as a reference. PCR conditions were as follows: stage I: 48° C. for 30 min; stage II: 95° C. for 10 min; stage III: [40 cycles] 95° C. for 15 s followed by 60° C. for 1 min Using the correlative method, RNA-fold change in expression was calculated as Ct of gene—Ct of β-actin to generate ΔCt from which ΔCt of the normal sample was subtracted. These values were then converted to $\log_2$ values.

SDS-PAGE and Western Blot Analyses

Proteins were resolved on an 8%, 12%, or 15% SDS-PAGE gel (as appropriate) and electrophoretically transferred to polyvinyldifluoride (PVDF) membranes. After blocking with 5% (w/v) milk in TBST (Tris-Buffered Saline containing 0.1% Tween-20) for one hour at room temperature, membranes were incubated with primary antibodies (at appropriate dilution) overnight at 4° C., followed by extensive washing and incubation for 1 hour with the appropriate horseradish peroxidase-conjugated secondary antibodies (BioRad, Hercules, Calif.). Blots were washed extensively. A rabbit polyclonal EVI1 antibody was obtained (1:3000 dilution, St. Jude's Children's Hospital, Memphis, Tenn.). SnoN rabbit polyclonal (1:1000 dilution), PML, and p21 SMURF2 rabbit polyclonal (1:500 dilution), MRP1 mouse monoclonal (1:500 dilution) and GAPDH mouse monoclonal (1:250 dilution) antibodies were obtained from Santa Cruz Biotechnology (Santa Cruz, Calif.). TGFβRII rabbit polyclonal (1:1000 dilution) antibody was obtained from Strategic Diagnostics (Newark, Del.). Smad2/3 rabbit polyclonal (1:1000 dilution), Beclin-1 rabbit polyclonal (1:1000 dilution), AKT rabbit polyclonal (1:1000 dilution), TAK1 rabbit polyclonal (1:1000 dilution), PARP rabbit polyclonal (1:1000 dilution), Beclin-1 rabbit polyclonal (1:1000 dilution), caspase-3 rabbit polyclonal (1:1000) which detects the pro-caspase form, and ATG5 rabbit polyclonal (1:1000 dilution), LC3-II rabbit polyclonal (1:1000 dilution) antibodies were obtained from Cell Signaling Technology (Danvers, Mass.). The HSP27 mouse monoclonal (1:1000 dilution) antibody was obtained from Stressgen (Ann Arbor, Mich.). Blots were developed using chemiluminescence substrates (Amersham Piscataway, N.J. or BioRad, Hercules, Calif.). Monoclonal PAI-1 antibody was obtained from BD Pharmingen. PSMAD2, total SMAD2/3, p-ERK, p-AKT, and total AKT antibodies were obtained from Cell Signaling Technology. A monoclonal antibody against Arkadia was obtained from Abnova (Taiwan).

Densitometric analysis was performed using the HP Scanjet 5590 and the Image J program (Image Processing and Analysis in Java, NIH Image Software). Bands were selected and the intensity values were normalized to those for GAPDH. The values are presented as fold-changes relative to control siRNA treated cells.

Proliferation and Cellular Migration Assays

TAg/hTert immortalized normal ovarian epithelial cells (TIOSE: T29 and T80) and ovarian cancer cells (OVCAR8, OVCA429, SKOV3, and HEY) were transfected with siRNA were counted 24 h post-transfection and 5000 cells were plated in each well of a 96-well plate maintained in 10% FBS. At various days, cells were fixed and stained with crystal violet solution, dissolved in Sorenson's buffer, and absorbance measured at 570 nm. To assess migration, cells transfected with siRNA were counted 24 h post-transfection and seeded into Boyden chamber inserts in serum-free media. FBS in the lower chamber media (RPMI 1640) was used as a chemoattractant for 24 h. The cells that migrated onto the lower membrane were stained with crystal violet, photographed, and counted.

Cell Viability Assays

Measurement of Intracellular ATP Levels. T80, HEY, and SKOV3 ovarian cells were seeded in triplicate for each treatment group at 5000 cells per well into each well of a 96 well white-opaque plate. Following overnight cell attachment, cells were treated for 18 hours with appropriate doses of arsenic trioxide or geldanamycin (0 mM, 2 µM, 5 µM, 10 µM, 25 µM, and 50 µM). Following termination of the cell treatments, the media was removed from the wells and replaced with 100 µl of phosphate-buffered saline (PBS). The plate was equilibrated to room temperature, 100 µl of Cell-Titer Glo reagent (Promega, Madison, Wis.) was added, and mixed on a plate shaker for 2 minutes. The plate was further incubated for 10 minutes at room temperature prior to reading with a Biotek luminescence plate reader to obtain relative light unit (RLU) measurements. Empty wells (containing no cells) were utilized as a correction for background luminescence. All experiments were performed in triplicate.

Glutathione (GSH) was measured using the GSH Glo kit (Promega). Briefly, T80, HEY, and SKOV3 ovarian cells were plated at 5000 cells/well in opaque white 96 well plates. Following overnight attachment, cells were treated with $As_2O_3$ for 18 hours. Following cell treatments, the media was discarded and fresh PBS was added for washout followed by the addition of 100 µl of GSH-Glo reagent. Following a 2 minute shake, the cells were incubated at room temperature for 30 minutes followed by the addition of reconstituted luciferase detection reagent. The cells were incubated for a further 15 minutes at room temperature and the plate was read on a Biotek luminescence plate reader. All measurements were performed in triplicate.

For assessment of apoptosis, the Annexin V-propidium iodide staining kit (Calbiochem, San Diego, Calif.) was used according to the manufacturer's protocol. Briefly, cells were treated with $As_2O_3$ for 24 hours at which time both the floating and adherent cells (removed by trypsinization) were collected. Cells were resuspended in PBS followed by the addition of annexin V-FITC and propidium iodide. The samples were then analyzed by flow cytometry at the MD Anderson Cancer Center FACS Core Facility. The FITC and the propidium iodide signals were detected at 518 nm with FL1 and at 620 nm with FL2, respectively. The log fluorescence values of annexin V-FITC and propidium iodide are displayed on the X and Y axis, respectively.

Direct and Indirect Immunofluorescence Microscopy

HEY cells were seeded onto glass coverslips and allowed to adhere following overnight incubation. The cells were then transiently transfected with EGFP-LC3 (Addgene, Cambridge, Mass.) and allowed to recover for 24 hours. The cells were treated at the appropriate concentrations of $As_2O_3$ in the absence or presence of 3-MA (5 and 10 mM), for 18 hours. The cells were then fixed in 4% paraformaldehyde in PBS for 30 minutes at room temperature, washed twice in PBS, and blocked for 1 hour at room temperature in PBS containing 5% goat serum and 0.1% Triton X-100. The cells were counterstained with Hoescht nuclear stain, washed 3 times for 5 minutes in PBS, anti-Fade containing DAPI nuclear stain was then applied, and coverslips mounted onto glass slides and viewed under a Zeiss inverted fluorescence microscope (Moffitt Cancer Center Microscopy Core).

Alternatively, Normal ovarian epithelial cells immortalized with hTert/large T antigen (TIOSE: T29) cells were nucleofector transfected with SnoN with EGFP plasmid or control vector in the absence or presence of PML isoforms (PML1, PML2, PML3, PML4, or PML5 in pcDNA3.1) and plated onto glass coverslips for 24 h. The cells were then fixed in 4% paraformaldehyde in phosphate-buffered saline (PBS) for 30 min at room temperature, washed twice in PBS, and blocked for 1 h at room temperature in PBS containing 5% goat serum and 0.1% Triton X-100. Primary antibodies (PML used at 1:1000 dilution) were incubated in PBS containing 1% goat serum and 0.1% Triton X-100 overnight at 4° C. The cells were washed 3 times for 5 min in PBS and then incubated with the appropriate cy3-fluorescent conjugated antibody for 1 h in PBS containing 1% goat serum and 0.1% Triton X-100. The cells were washed 3 times for 5 min in PBS, and mounted onto glass slides and viewed under a fluorescence microscope.

Autophagy induction was analyzed using electron microscopy. To demonstrate the induction in arsenic trioxide treated cells morphologically, HEY cells were treated with or without arsenic trioxide (dose) across a series of time points (h) in T-75 culture flasks. Cells were then fixed in 2.5% glutaraldehyde in 0.1M phosphate buffer overnight at 4° C. Following rinsing in buffer, cells were scraped from the culture flasks, washed, and then post-fixed in 1% osmium tetroxide in buffer. After dehydration in a graded series of acetone, the cells were embedded in Embed 812 epoxy resin. Thin sections (70 nm) were cut on an Ultramicrotome. The sections on the grids were stained with uranyl acetate and lead citrate. The sections were examined on a Transmission Electron Microscope (Morgagni 268D).

RT-PCR Cloning and Plasmid Construction

One-step RT-PCR (Invitrogen) was used to amplify SnoN PCR products, which were gel purified, cloned into pTOPO-XL vector, and sequenced. EcoRI was used to release the full-length insert and used for ligation into pEGFP-C1 (Invitrogen) vector for expression studies. All constructs were sequenced prior to use. The following primers were used for RT-PCR:

SEQ ID 4: SnoN Forward Primer: CGG AAC AAG GGC CAC CAT GGA AAA CCT CCA GAC A.
SEQ ID 5: SnoN Reverse Primer: CAG GCC TGG CGC CCT ATT CTT TAG CAG T.

Transcriptional Assays

Nucleofector transfection was performed in TIOSE (T29) cells with SnoN (5 mg) in combination with p21 (obtained from Dr. WafikEl-Deiry (University of Pennsylvania)), p3TP-Lux (containing the firefly luciferase reporter gene under the control of three 12-O-tetradecanoylphorbol-13-acetate (TPA) response elements and a fragment of the PAI-1 promoter), and p(CAGA)12-Lux, a reporter gene containing 12 repeats of Smad binding sequences from the PAI-1 promoter (obtained from Dr. Carlos Arteaga (Vanderbilt University)) (1 mg) as well as the AP-1 cis-reporter plasmid (Stratagene) using $Renilla$ luciferase to normalize (0.05 mg). Cells were re-seeded 6 h post-transfection, allowed to adhere for 6 h, and serum starved/treated with 50 pM TGF-β. TGF-β was chosen as being on the linear portion of the dose response curve. The following day (24 h post-transfection), cells were harvested in passive lysis buffer and assessed for luciferase activity using Dual Luciferase Assay kit (Promega).

SiRNA Transfection of Ovarian Cells

Two independent siRNAs against SnoN/SkiL were obtained from Ambion (Austin, Tex.; catalog #: AM16704; ID #: 107695 and 107696), AKT from Cell Signaling Technology (Danvers, Mass.), HSP27 (Cell Signaling Technology), PML (L-006547-00), SMURF2 (Dharmacon, L-007194-00), non-targeting control-1 siRNA from Dharmacon (Lafayette, Colo.) (D-001210-01-05);
EVI1 Exon VII from Dharmacon, custom-designed sequence:
SEQ ID 6: sense 5' ACU ACG UCU UCC UUA AAU AUU-3', and
TAK1 from Dharmacon, custom-designed sequence:
SEQ ID 7: sense 5'-GUA GAU CCA UCC AAG ACU UUU-3'.

The ovarian cancer cells, HEY and OVCA429, were plated at 250,000 cells (unless otherwise specified) in each well of a 6-well plate. The following day, the cells were transfected using 20 μM siRNA against SnoN, EVI1 Exon VII, AKT, HSP27, TAK1, SMURF2, or non-targeting control-1 siRNA were transfected using Dharmafect I transfection reagent (Dharmacon). Briefly, cells were cultured in complete medium for 24 hours prior to transfection (2 ml media in each well of 6 well plate) at which time the medium was changed to serum and antibiotic-free medium. Dharmafect I (4 μl) was incubated in 100 μl of serum and antibiotic-free media for 10 minutes at room temperature, followed by the addition of 5 μl of siRNA (20 μM) and further incubated for 20 minutes at room temperature. The mixture was added to the cells and incubated for 48 hours prior to isolation of RNA and protein for qPCR and western analysis, respectively.

Cell Treatments with Clinical Inhibitors

The clinical inhibitors $As_2O_3$, geldanamycin (17-AAG) (dissolved in dimethylsulfoxide [DMSO]), and MG132 (dissolved in DMSO) were obtained from Sigma-Aldrich (St. Louis, Mo.), Fisher Scientific (Pittsburgh, Pa.), and Alexis Biochemicals (Farmingdale, N.Y.), respectively. N-acetyl-L-cysteine (NAC; dissolved in media) and Bortezomib (PS-341; dissolved in DMSO) were obtained from Fisher Scientific. 3-Methyladenine (3-MA; dissolved in media) was obtained from MP Biomedicals (Solon, Ohio). Tiron (4,5-Dihydroxy-1,3-benzenedisulfonic acid, dissolved in media) was obtained from Fisher Scientific. zVAD-fmk (dissolved in DMSO) and bafilomycin A (dissolved in DMSO) was obtained from Axxora LLC (San Diego, Calif.). Bovine catalase was obtained from Sigma-Aldrich. HBED and Mn TBAP was obtained from ENZO Life Sciences (Farmingdale, N.Y.). Ovarian cells were plated in 6-well plates at 250,000 cells per well and grown in complete medium. The following day, the cells were treated with 5 μM MG132, $As_2O_3$ (between 2-50 μM), 17-AAG (between 2-50 μM), NAC (Fisher Scientific, between 25 μM to 1 mM), Tiron (between 25 μM to 1 mM), 3-MA (0.1 mM to 10 mM), or zVAD-fmk (25 μM to 100 μM). For control cells, DMSO (a final concentration of <0.5%) was added to compare appropriately to drugs dissolved in DMSO. After the appropriate incubation time (6 or 18 hours), cell lysates were collected, protein quantified, and SDS-PAGE/western analysis was performed. In addition, for selected studies, RNA was isolated, quantified, and used for qPCR analysis.

Colony Formation Assays and SA-β-Gal Staining

TAg/hTert immortalized normal ovarian epithelial cells (TIOSE: T29) infected with SnoN or control retrovirus and selected for 2 weeks in G418 were counted and 5000 cells were plated in each well of a 96-well plate maintained in 10% FBS. At various days, cells were fixed and stained with crystal violet solution, dissolved in Sorenson's buffer, and absorbance measured at 570 nm. For colony formation assays, cells were plated at 500 cells/well in each well of 6 well plate and grown in G418-selection media for 2 weeks after which time the cells were stained with Coomassie staining solution (0.1% Coomassie Brilliant Blue R-250 in 30% methanol and 10% acetic acid) and photographed. Staining for β-galactosidase activity at pH 6 was performed using a staining kit from Cell Signaling Technology.

Long-Term Expression of SnoN Induces Senescence in Non-Transformed Immortalized Ovarian Epithelial Cells SnoN is located at a frequent and localized point of genomic amplification at 3q26.2 in advanced stage serous epithelial ovarian cancers, as seen by high-resolution array CGH using a bacterial artificial chromosome (BAC) contig encompassing the q arm of chromosome 3. Further, there is a marked and frequent accumulation of SnoN transcripts in ovarian cancer. Although transient expression of SnoN repressed both the PAI-1 and CAGA promoters as well as the AP-1 reporter in TAg/hTert immortalized normal ovarian epithelial T29 cells (TIOSE), there was little effect on the p21 promoter and cell growth. However, SnoN knockdown using siRNA in both TIOSE and OVCA indicated that SnoN increases cellular proliferation. In contrast, stable expression of SnoN in T29 cells induced growth arrest and senescence in several independent SnoN expressing clones. Thus, although SnoN levels are elevated in ovarian cancers likely contributing to tumor progression, SnoN functions to decrease tumorigenic properties in normal ovarian epithelial cells. Thus, SnoN may contribute to the pro- and anti-tumorigenic properties of TGF-β during tumor initiation and progression.

To explore the consequences of stable SnoN overexpression in ovarian cancer cells on tumor initiation and progression, T29 cell line SnoN expression was established at levels similar to those present in ovarian cancer cells. Surprisingly, SnoN expression conferred a distinct growth disadvantage to 3 independent SnoN expressing clones (F-11, E-9, and G-11), seen in FIG. 1. The F-11 clone which expressed the lowest levels of SnoN was used for subsequent detailed functional analysis although similar results were observed with the E-9 and G-11 SnoN clones. Both in proliferation and anchorage-dependent colony forming assays, seen in FIG. 1, SnoN expressing F-11 cells exhibited a growth disadvantage when assessed in the presence of 10% FBS. Furthermore, many of the F-11 cells were observed to have a flat morphology reminiscent of senescence, data not shown. SA-β-gal activity represents the gold standard for detection of oncogene-induced senescence (Coates, 2002. Markers of senescence? J. Pathol 196, 371-373; Roninson, 2003. Tumor cell senescence in cancer treatment. Cancer Res. 63, 2705-2715). Indeed, staining with SA-β-gal demonstrated a high frequency of senescent cells in SnoN expressing F-11 cells, data not shown. Western analysis showed increased p21 and PAI-1 levels as well as elevated phospho-ERK in SnoN stably expressing cells, data not shown.

Although p21 is a principal p53 target gene (Efeyan et al., 2006. Genetic dissection of the role of p21(Cip1/Waf1) in p53-mediated tumour suppression. Oncogene 26, 1645-1649) and a central component in a variety of p53-mediated stress responses, its expression is likely mediated through p53-independent mechanisms in T29 cells, which are immortalized with large T antigen which binds and inactivates p53. Strikingly, p-AKT levels were reduced in SnoN expressing cells indicating that the cell survival pathway mediated through AKT is likely aberrant. Thus, multiple signaling pathways appear to be aberrant in SnoN expressing cells likely contributing to the observed growth arrest and senescence.

Example 1

Increased SnoN DNA Copy Number in Ovarian Carcinomas

Figure 2:
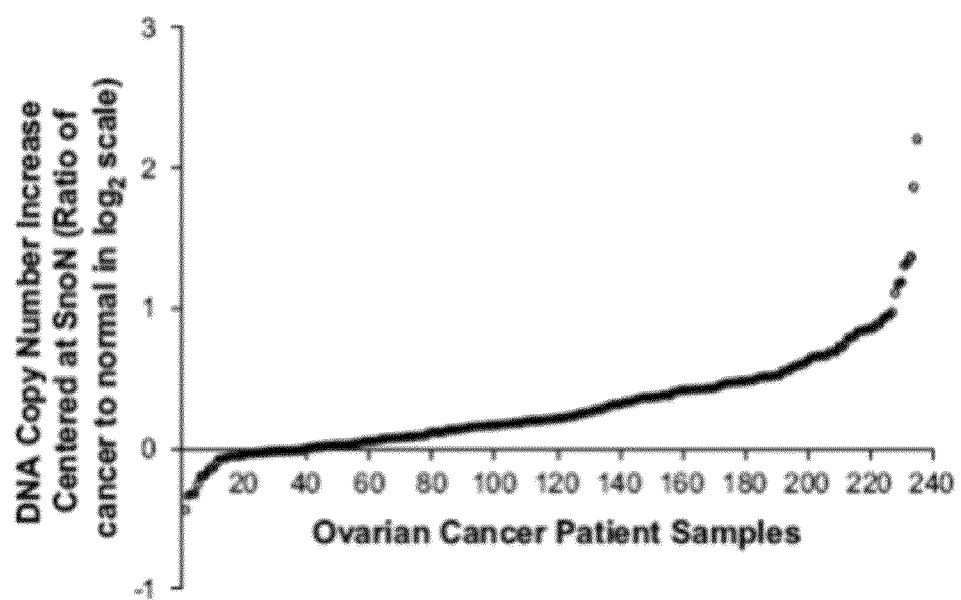
FIG. 2 is a graph showing CGH analysis of DNA copy number increase centered at SnoN in 235 advanced stage serous epithelial ovarian cancers represented at log 2 ratio of cancer patient DNA to normal DNA.

It has been demonstrated that EVI1 (Nanjundan et al., 2007. Amplification of MDS1/EVI1 and EVI1, located in the 3q26.2 amplicon, is associated with favorable patient prognosis in ovarian cancer. Cancer Res. 67, 3074-3084), the p110a catalytic subunit of phosphatidylinositol-3-kinase (PI3K), and PKCi (Eder et al., 2005. Atypical PKCiota contributes to poor prognosis through loss of apical-basal polarity and cyclin E overexpression in ovarian cancer. Proc. Natl. Acad. Sci. USA 102, 12519-12524; Shayesteh et al., 1999. PIK3CA is implicated as an oncogene in ovarian cancer. Nat. Genet. 21, 99-102) are elevated at the mRNA and protein levels in association with the 3q26 copy number increase in ovarian cancer. Further, reports indicate that SnoN, located adjacent to PKCi, may be a target for gene amplification at 3q26 in squamous-cell carcinomas of the esophagus (Imoto et al., 2001. SNO is a probable target for gene amplification at 3q26 in squamous cell carcinomas of the esophagus. Biochem. Biophys. Res. Commun. 286, 559-565). SnoN mRNA was found to be increased and associated with a worsened prognosis in estrogen receptor-positive breast carcinomas (Zhang et al., 2003. Ski-related novel protein N (SnoN), a negative controller of transforming growth factor-beta signaling, is a prognostic marker in estrogen receptor-positive breast carcinomas. Cancer Res. 63, 5005-5010) and is increased in breast and lung cancer cell lines (Thu et al., 2007. Dual role of SnoN in mammalian tumorigenesis. Mol. Cell. Biol. 27, 324-339). As indicated by a high-density array CGH contig, amplifications and deletions on chromosome 3q varies dramatically between different patients with several occurring frequently, data not shown. The complex pattern of aberrations at 3q in different patients suggests that different genetic events may contribute to overall structure and selection of the 3q amplicon. Chromosome 3q26.2 exhibits multiple regional amplifications including a discrete amplicon encompassing Ch3: 171039661-171634577 (FLJ23259 to CLDN11) encompassing SnoN at Ch3: 171558210-171593226, PKCi at Ch3: 171422921-171503889 and a number of neighboring genes including GPCR150, and PHC3 as well as a discreet amplicon upstream of SnoN encompassing MDS1 at Ch3: 170349964-170864112 and EVI1 at Ch3: 170285244-170346787, which is frequently and highly amplified in ovarian cancer (Nanjundan et al., 2007. Amplification of MDS1/EVI1 and EVI1, located in the 3q26.2 amplicon, is associated with favorable patient prognosis in ovarian cancer. Cancer Res. 67, 3074-3084). As indicated in FIG. 2, based on the BAC encompassing SnoN, the DNA copy number of SnoN was increased in approximately 60% of 235 serous epithelial advanced stage ovarian cancers with 35% showing a gain of at least one copy.

Sequencing of exon 1, which contains the transformation and SMAD binding domain of SnoN (Liu et al., 2001. Ski/Sno and TGF-β signaling. Cytokine Growth Factor Rev. 12, 1-8) from genomic DNA in 48 serous epithelial advanced stage ovarian cancers, did not identify any mutations other than one documented SNP (A38V), which was present in all samples analyzed. The frequency of this polymorphism in normal or benign samples as well as the functional relevance of this conserved amino acid change is presently unknown. Nevertheless, amplification was not associated with mutations in the functional domain of SnoN.

Figure 3:
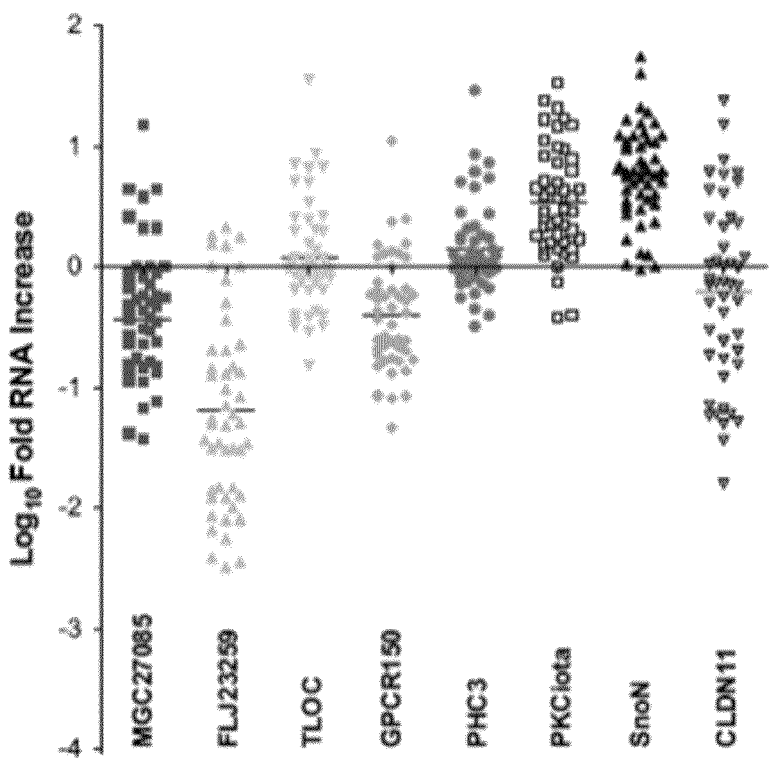
FIG. 3 is a graph showing SnoN genomic copy number increase is associated with a selective accumulation of SnoN transcripts. RNA expression levels of genes surrounding SnoN along chromosome 3q, from MGC27085 to CLDN11, were assessed by quantitative polymerase chain reaction (qPCR) analysis in ovarian tissue samples. The results are displayed as fold-alterations in RNA expression for normal ovarian epithelium, benign tumor samples, and advanced tumors (stage III and IV), compared to the average of the normal epithelium. MGC27085 and FLJ23259 are anonymous transcripts, TLOC is translocation protein 1, GPCR150 is G-protein coupled receptor 150 (GPR160), and PHC3 is polyhomeotic-like 3, PKCi is protein kinase C iota, SnoN is Ski-like, and CLDN11 is claudin 11.
Figure 4:
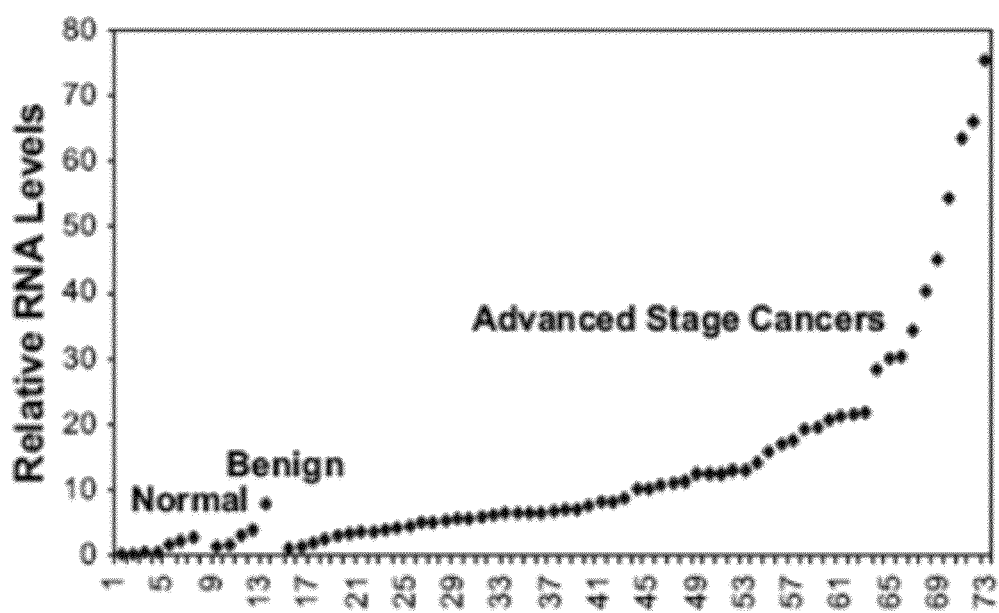
FIG. 4 is a graph showing the results from FIG. 2, displayed as log 10-fold-alterations in RNA expression for average of the normal and benign patient samples relative to advanced stage ovarian cancer patient samples.
Figure 5:
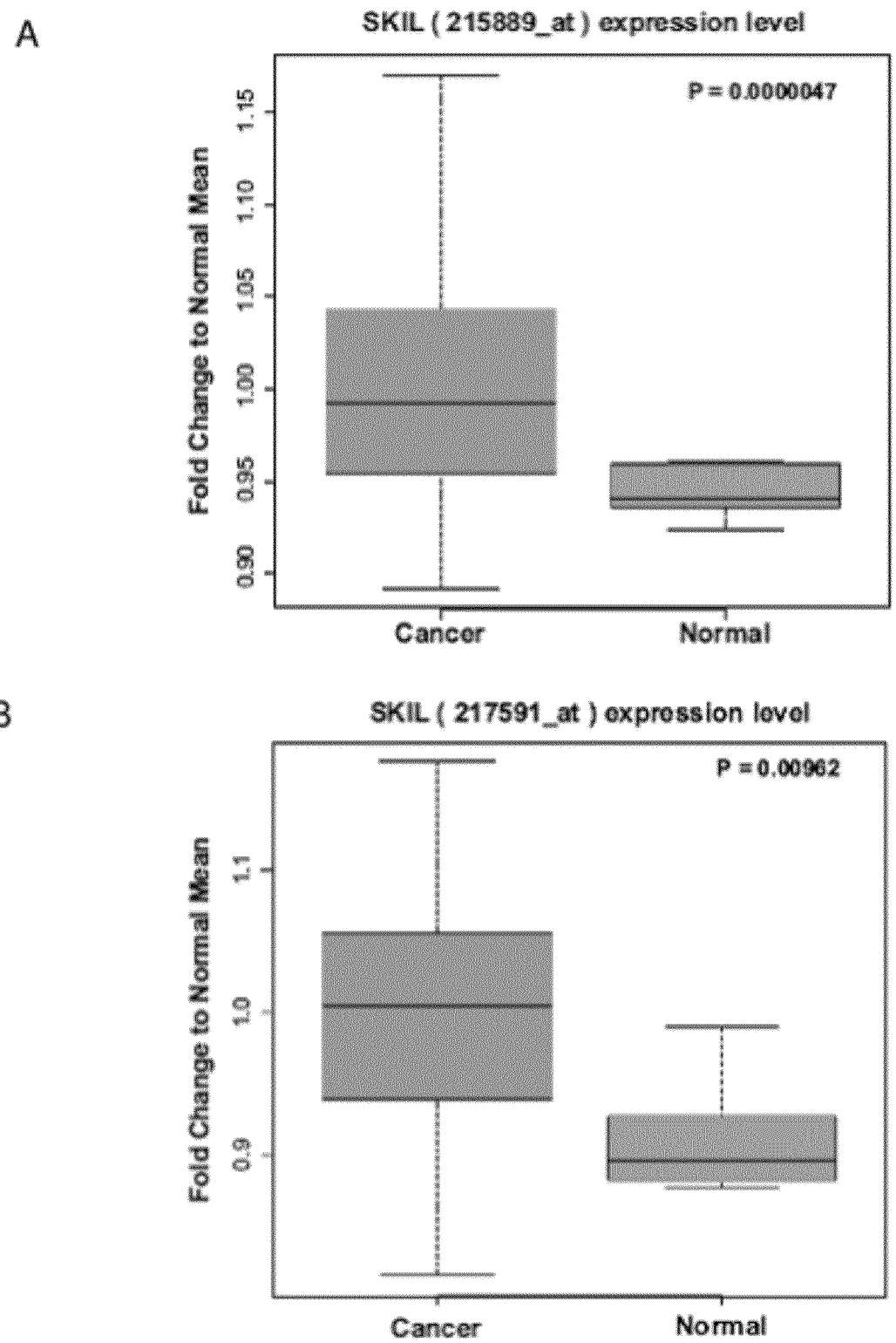
FIGS. 5(A) and (B) are block graphs showing transcriptional profiling of the UCSF ovarian dataset showing the elevated SnoN RNA expression with 3 probes and displayed as fold change to normal mean. Sixty-nine patients were analyzed in the "cancer" group while 6 benign tumors were analyzed in the "normal" group.

To assess whether the observed DNA copy number increase in SnoN is associated with increased transcript levels, transcripts from the 8 open reading frames in the region encompassed by MGC27085 to CLDN11 (Ch3: 170993963-171634589) were determined by quantitative polymerase chain reaction (qPCR) analysis. SnoN was found to be the most highly and frequently elevated transcript within this region followed by PKCi, seen in FIG. 3. SnoN RNA levels were increased at least 3-fold in >80% of serous epithelial ovarian cancers as compared to normal ovarian surface epithelial cells and benign tumors, seen in FIGS. 3 and 4. Another independent data set of 69 cancer patient samples compared to 5 benign patient samples (3 probes) confirmed the presence of increased SnoN levels in advanced stage ovarian cancers by transcriptional profiling (p-value<0.05), seen in FIG. 5. Furthermore, SnoN DNA and RNA levels demonstrated significant correlation suggesting that tumors with increased DNA copy number are likely to have increased SnoN transcripts ($R^2=0.3955$, p-value=<0.01), data not shown. However, in many cases SnoN mRNA is increased in the absence of increases at the DNA level and the level of increase in mRNA levels frequently exceed the magnitude of DNA increases. This could be a reflection of the status of the TGF-β signaling pathway. Thus, epigenetic modifications of SnoN presently unreported may play an important role in the regulation of its activity or expression during ovarian cancer progression.

Although the levels of SnoN protein expression appears to be present and elevated in stage II, III, and IV cancer patients compared to 3 stage I tumors, there is substantial variability in its level of expression across the different stages, data not shown. Thus, SnoN expression and activity may vary during different stages of cancer progression. Of the 44 patient samples analyzed, 38 samples were high grade tumors and the remaining were low grade or low metastatic potential (LMP) tumors. However, there was no clear pattern in the expression of SnoN between these different tumor grades.

SnoN levels are not only tightly transcriptionally regulated upon activation of the TGF-β signaling cascade where a marked increase in SnoN expression in both epithelial cells and fibroblasts results in termination of SMAD-mediated transactivation (Thu et al., 2005. Requirement for the SnoN oncoprotein in transforming growth factor beta-induced oncogenic transformation of fibroblast cells. Mol. Cell. Biol. 25, 10731-10744), but also further regulated by proteosome-mediated degradation. To test this possibility, the expression of phospho-SMAD2/3 and Arkadia, which are regulators of the TGF-β signaling pathway, was evaluated. Arkadia, an E3 ubiquitin ligase, induces the degradation of SnoN, allowing induction of transcription upon TGF-β stimulation (Levy et al., 2007. Arkadia activates Smad3/Smad-4-dependent transcription by triggering signal-induced SnoN degradation. Mol. Cell. Biol. 27, 6068-6083; Nagano et al., 2007. Arkadia induces degradation of SnoN and c-Ski to enhance transforming growth factor-beta signaling. J. Biol. Chem. 282, 20492-20501). In fibroblasts, within 30 min following TGF-β stimulation, SnoN is rapidly degraded by the ubiquitin dependent proteosome via SMAD2/3-dependent recruitment of ubiquitin ligase SMURF2 and CDH-1 anaphase-promoting ubiquitin ligase complex. Subsequent degradation by the proteasome removes SnoN-mediated inhibition of the TGF-β signaling pathway thus, allowing activation of TGF-β target genes (Zhang et al., 2002. Proteasomal activity modulates TGF-ss signaling in a gene-specific manner. FEBS Lett. 527, 58-62; Zhu et al., 2005. Requirement for the SnoN oncoprotein in transforming growth factor beta-induced oncogenic transformation of fibroblast cells. Mol. Cell. Biol. 25, 10731-10744). However, the expression of both phospho-SMAD2/3 as well as Arkadia by Western analysis were very low to undetectable across the ovarian cancer patients (stage I-IV); therefore, it remains unclear whether the known levels of regulation of SnoN in ovarian cancer correlates to its protein stability.

Figure 6:
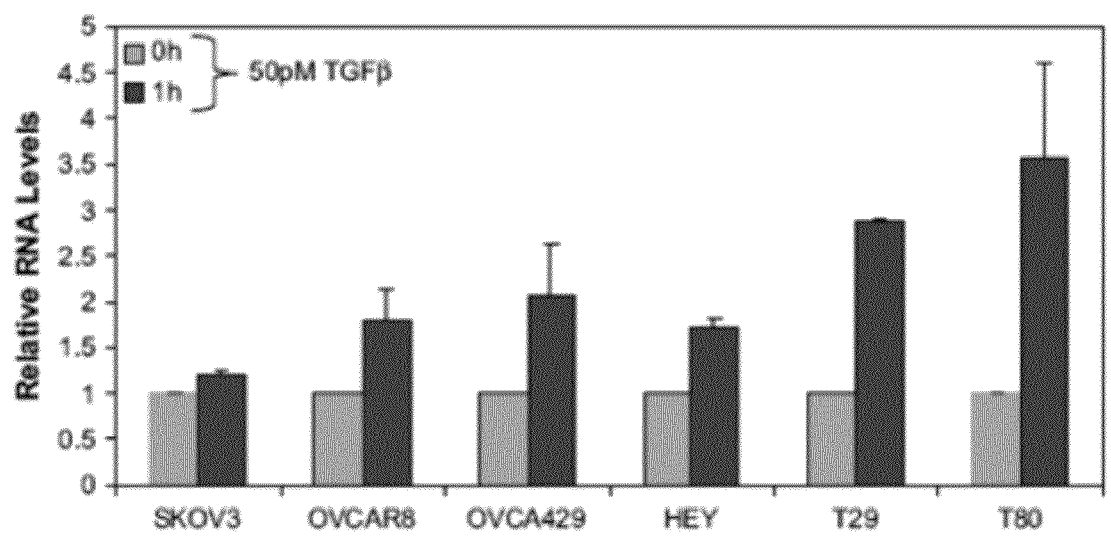
FIG. 6 is a graph showing induction of SnoN RNA levels by TGF-β is controlled by multiple signaling pathways. Immortalized normal ovarian epithelial cells and ovarian carcinoma cells were treated for 1 h with 50 pM TGF-β. RNA was extracted and qPCR analysis was performed to assess SnoN expression. The results are presented as RNA-fold increases.

At the transcriptional level, SnoN levels are regulated both in TAg and hTert immortalized normal ovarian epithelial cells (T80 and T29) as well as ovarian cancer cell lines (SKOV3, OVCAR8, OVCA429, and HEY). Endogenous SnoN RNA levels are upregulated (as assessed by qPCR) following a 1 h treatment with 50 pM TGF-β ranging from 1.5-fold to 5-fold which was most markedly induced in immortalized normal ovarian epithelial cell (T29 and T80) and to a lesser degree in ovarian carcinoma cell lines, seen in FIG. 6.

Figure 7:
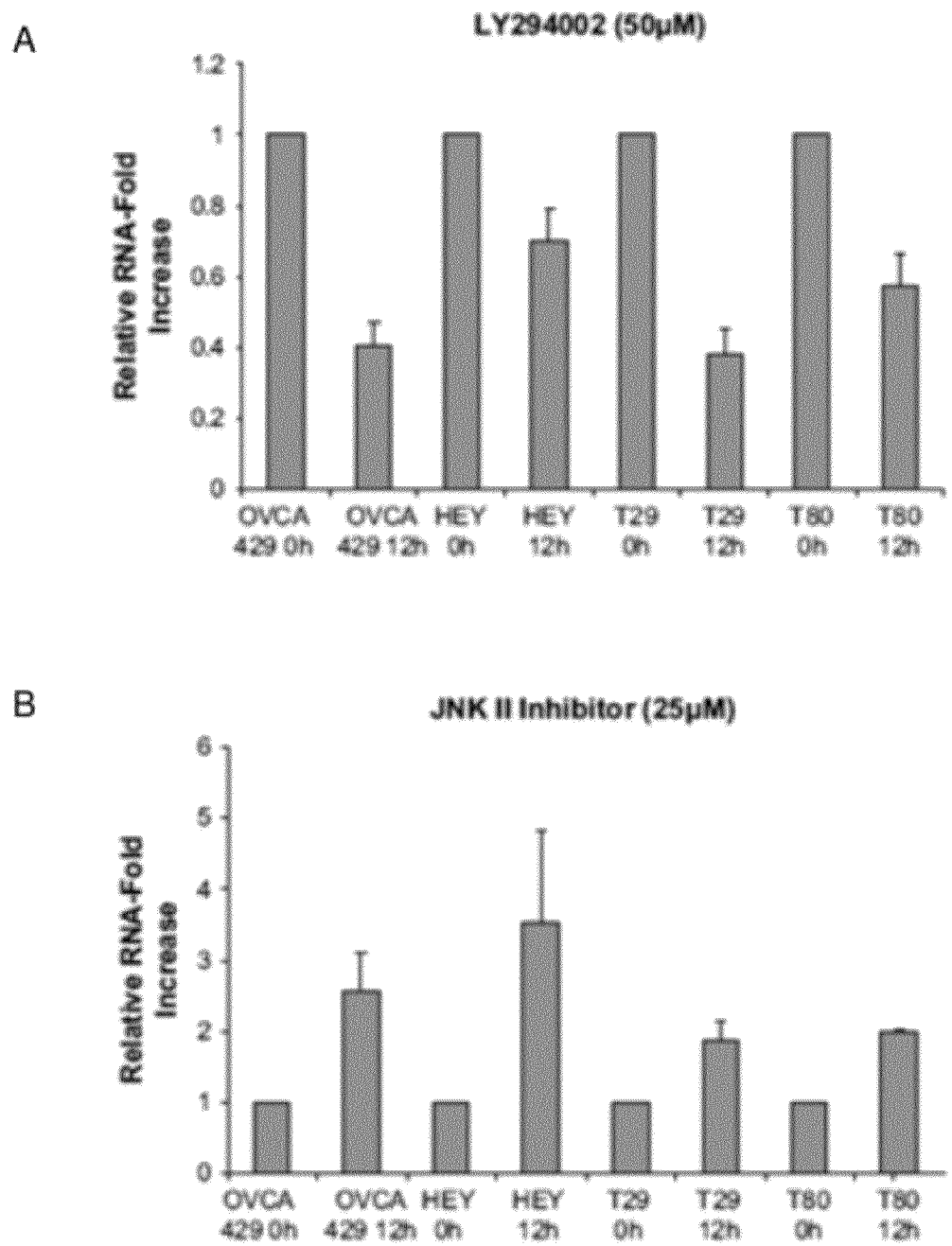
FIGS. 7(A) and (B) are graphs showing the effect of (A) LY294002 or (B) JNK II inhibitor on SnoN RNA levels. OVCA429, HEY, T29, and T80 cells were treated with 50 mM PI3K inhibitor or 25 mM JNK II inhibitor for 12 h. RNA was extracted and qPCR analysis was performed to assess SnoN expression. The results are presented as RNA-fold increases.

Modulation of mRNA stability plays a central role in cellular homeostasis and many pathologies arise due to dysregulated mRNA stability including cancer which is controlled through a variety of RNA/protein interactions as well as modulation of signaling pathways that post-translationally modify RNA binding proteins and other associated proteins. Some signaling pathways that alter these events include the PI3K/AKT, JNK, and MEK pathways. Strikingly, basal SnoN RNA levels (0 h, unstimulated/untreated cells) were found regulated by signaling pathway inhibitors including the PI3K inhibitor (LY294002 at 50 mM) where SnoN RNA levels were dramatically reduced by 50%, seen in FIG. 7(a), and the JNK inhibitor (25 mM) which induced a 2-fold to 4-fold increase, seen in FIG. 7(b), in SnoN levels 12 h post-treatment in both ovarian carcinoma cell lines (including OVCA429 and HEY) and immortalized normal ovarian epithelial cells (T29 and T80). In addition, the MEK pathway was examined using the U0126 inhibitor (25 mM). However, its effect was not significant, data not shown, compared to the effects of the PI3K and JNK inhibitors. These results implicate positive and negative regulation by the PI3K and JNK pathway, respectively, which regulates basal SnoN RNA levels.

Figure 8:
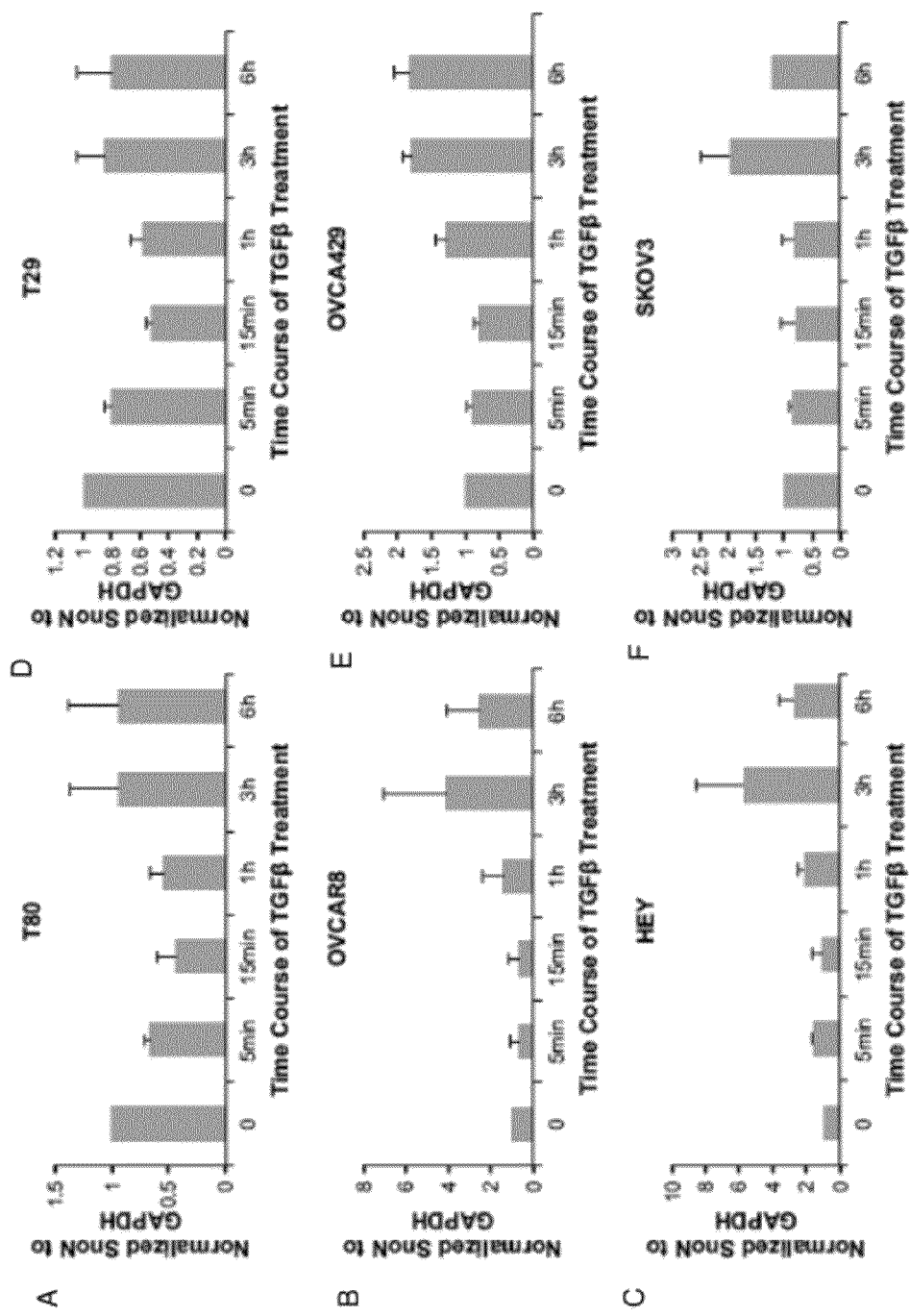
FIG. 8(A) through (F) are graphs showing the densitometric analyses (avg±std of 2 independent experiments) of TGF-β and MG132 on SnoN expression levels in ovarian carcinoma cells. (A) T80, (B) OVCAR8, (C) HEY, (D) T29, (E) OVCA429, and (F) SKOV3 cells were treated with 50 pM TGF-β from 5 min to 6 h followed by Western analysis to examine protein expression levels of GAPDH.

With respect to post-transcriptional regulation of SnoN, there was a dramatic decrease in SnoN protein levels in immortalized normal ovarian epithelial cells (T29 and T80) between 15 min and 1 h post-TGF-β stimulation returning to baseline levels by 3 h. In contrast, a similar marked decrease was not observed in SnoN protein levels in ovarian carcinoma cell lines (SKOV3, OVCA429, OVCAR8, and HEY), seen in FIG. 8, following TGF-β addition within 1 h post-stimulation. However, in ovarian cancer cells, TGF-β induced a dramatic increase in SnoN protein levels between 1 and 3 h post stimulation potentially functioning as a feedback loop to constrain TGF-β signaling (Stroschein et al., 1999. Negative feedback regulation of TGF-β signaling by the SnoN oncoprotein. Science 286, 771-774). In addition, both immortalized normal (T29 and T80) and ovarian carcinoma cells (SKOV3, HEY, OVCA429, and OVCAR8) are responsive to TGF-β since phospho-SMAD2 levels were markedly elevated 1 h post stimulation.

Figure 9:
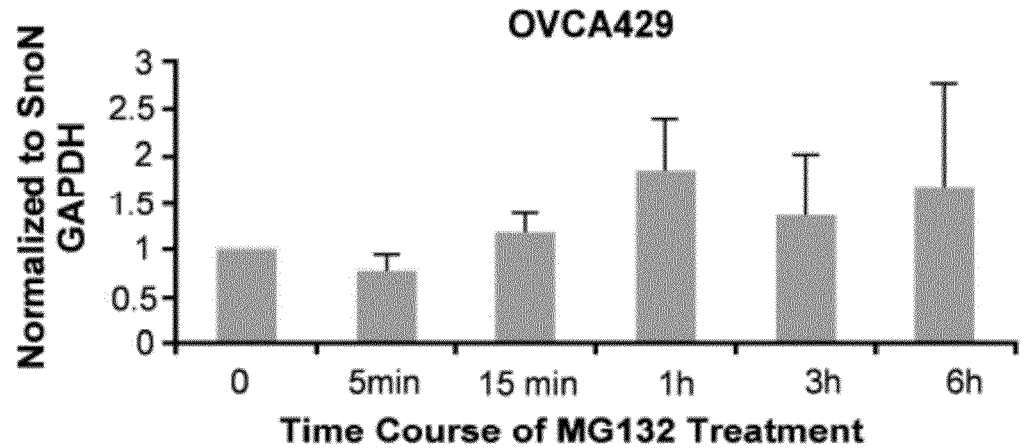
FIGS. 9(A) and (B) are graphs of the densitometric analyses (avg±std of 2 independent experiments) of (A) OVCA429 and (B) HEY cells treated with MG132 from 5 min to 6 h followed by Western analysis to examine protein expression levels of SnoN and GAPDH as a loading control. Westerns is also presented.
Figure 9:
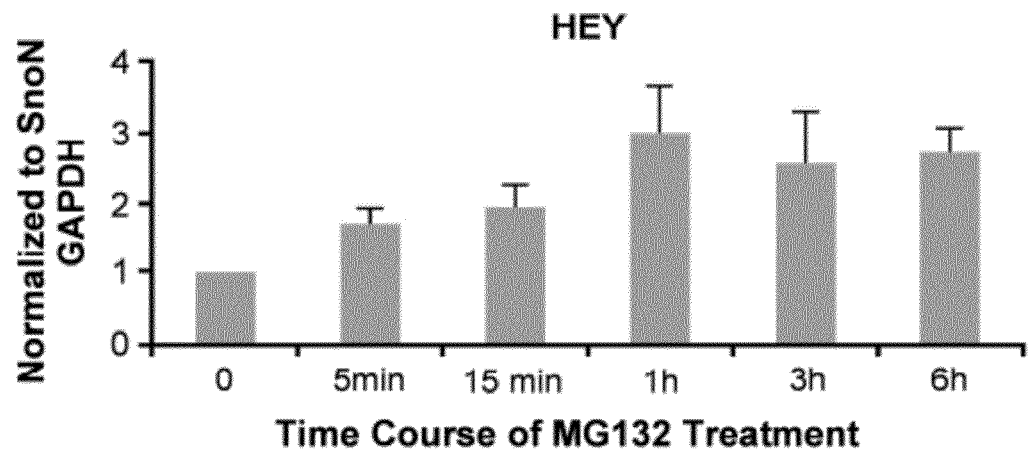
Figure 10:
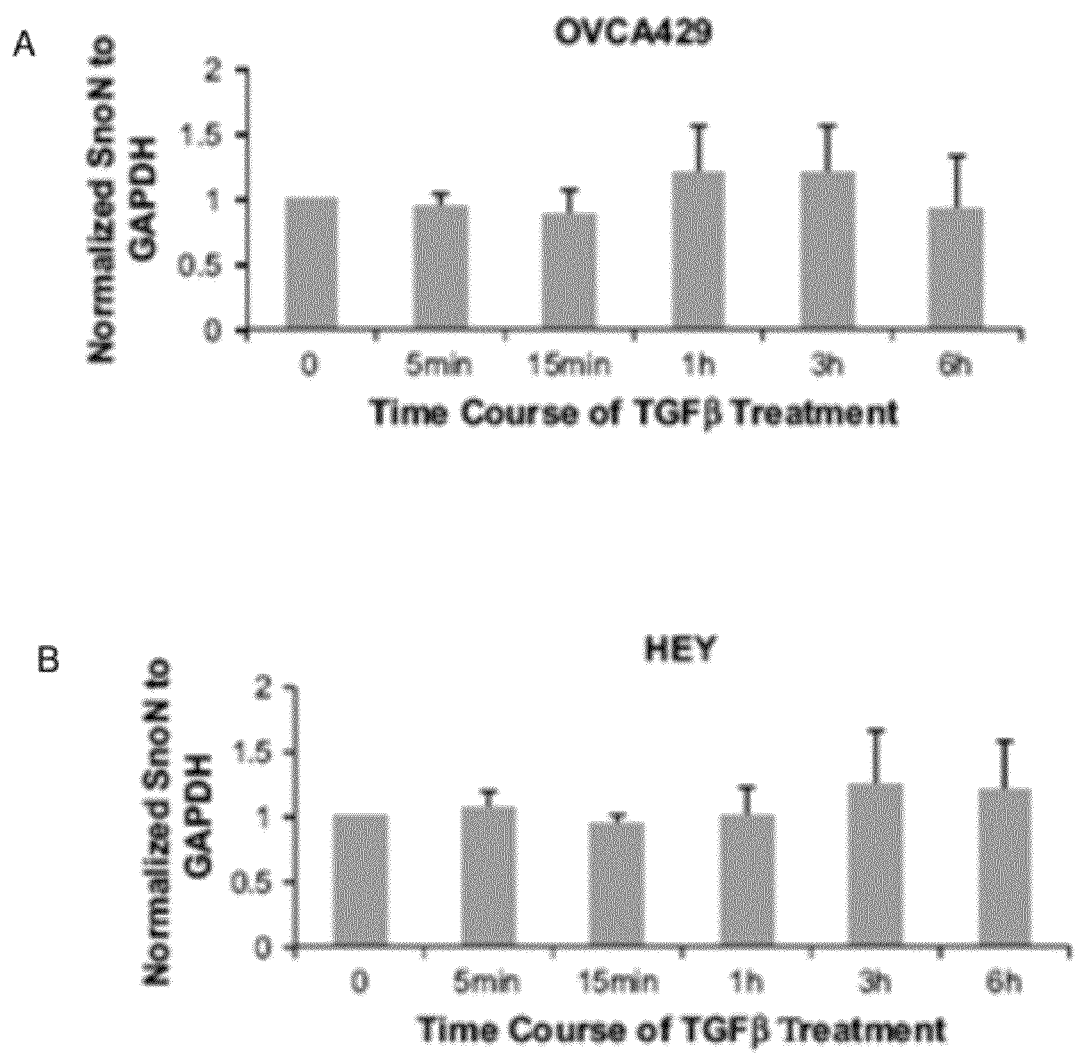
FIGS. 10(A) and (B) are graphs of the densitometric analyses (avg±std of 2 independent experiments) of (A) OVCA429 and (B) HEY cells pretreated with MG132 (10 mM) for 4 h followed by 50 pM TGF-β stimulation from 5 min to 6 h. Lysates were collected and Western analysis was performed to examine protein expression levels of SnoN using GAPDH as a loading control.

The increase in SnoN levels 1-3 h post-TGF-β stimulation may be the result of inhibition of the proteosome. To determine whether the increases in SnoN levels in the cancer cell lines after TGF-β treatment was, indeed, due to proteosome inhibition, ovarian cell lines (HEY and OVCA429) were pre-treated with MG132 for 4 h prior to stimulation with TGF-β. Treatment was selected at 4 h with MG132 (10 mM) as it induced a marked increase in SnoN basal levels attaining a threshold level between 3 and 6 h, seen in FIG. 9. These ovarian cancer cell lines were treated with TGF-β (from 5 min to 6 h) following 4 h pretreatment with MG132. In contrast to TGF-β treatment in the absence of MG132, seen in FIG. 8, TGF-β with MG132 pretreatment was observed not to markedly alter SnoN expression, seen in FIG. 10. Collectively, these results suggest that the resistance of ovarian carcinoma cell lines to TGF-β-induced growth arrest (Baldwin et al., 2003. Loss of c-myc repression coincides with ovarian cancer resistance to transforming growth factor beta growth arrest independent of transforming growth factor beta/Smad signaling. Cancer Res. 63, 1413-1419) may be a result of the failure to degrade SnoN. Thus, SnoN protein levels are tightly linked to the activation status of the TGF-β signaling cascade in ovarian epithelial cells.

Example 2

Figure 11:
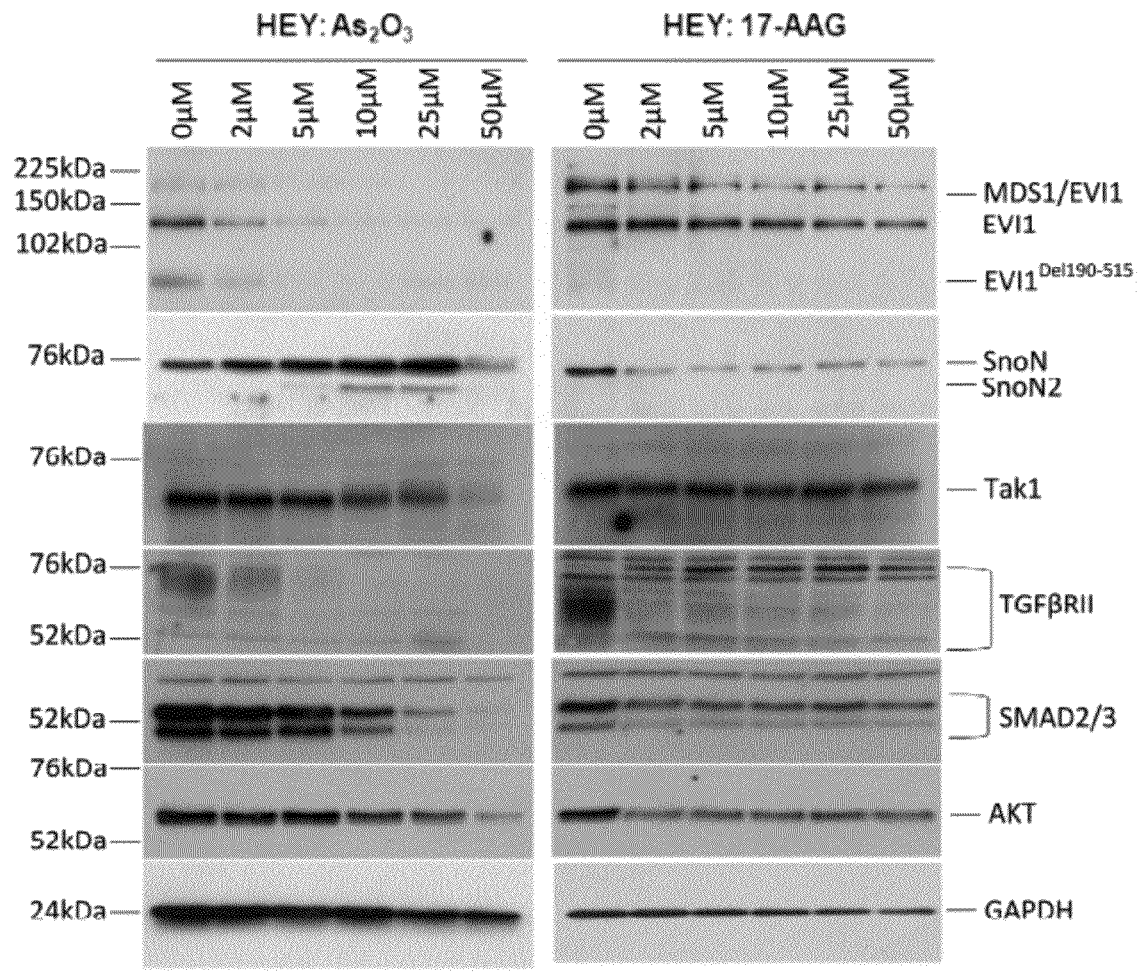
FIG. 11 is a Western blot showing dose response of $As_2O_3$ and 17-AAG in HEY ovarian cancer cell line in HEY cells after an 18 hour incubation. Cells were initially seeded at 250,000 cells per 6-well.
Figure 12:
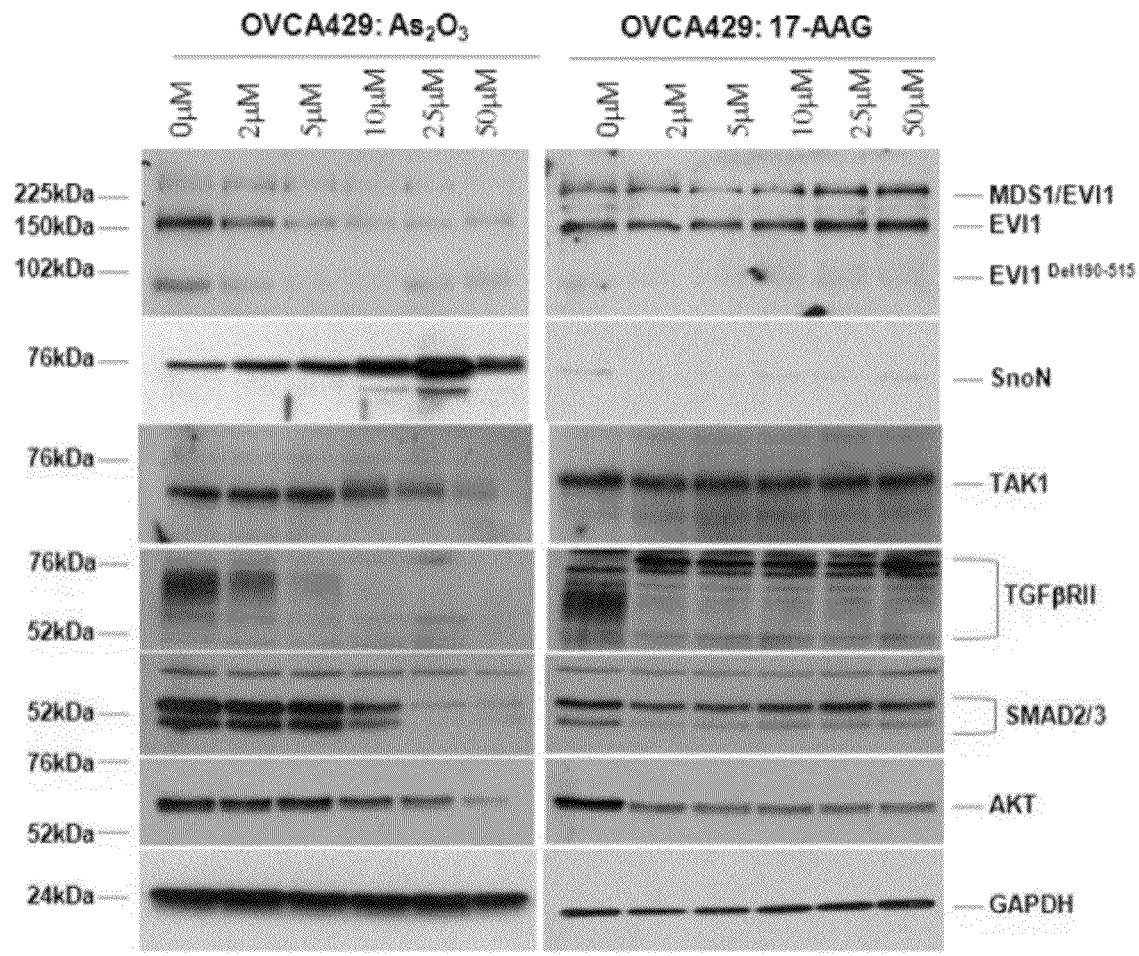
FIG. 12 is a Western blot showing the dose response of $As_2O_3$ and 17-AAG in OVCA429 ovarian cancer cells after an 18 hour incubation. Cells were initially seeded at 250,000 cells per 6-well.

As$_2$O$_3$ Alters Expression of TGFβ Signaling Mediators in Ovarian Cancer Cells As noted above, EVI1 is amplified at 3q26.2 in ovarian cancers, and As$_2$O$_3$ treatment reduces expression of EVI1 in acute promyelocytic leukemia (APL) cells (Shackelford, et al. 2006. Targeted degradation of the AML1/MDS1/EVI1 oncoprotein by arsenic trioxide. Cancer Res 66, 11360-11369). To determine whether As$_2$O$_3$ and/or 17-AAG could alter expression of EVI1 and other TGFβ signaling mediators in ovarian cancer cell lines, HEY and OVCA429 cells (both high EVI1 expressing cell lines) were treated for 18 hours with increasing doses of As$_2$O$_3$ and 17-AAG, seen in FIGS. 11 and 12. Interestingly, As$_2$O$_3$ markedly decreased protein levels of several EVI1 forms in both cell lines including MDS1/EVI1 (which consists of sequences derived from both EVI1 and the MDS1 gene, located telomeric to EVI1; Fears, et al. 1996. Intergenic splicing of MDS1 and EVI1 occurs in normal tissues as well as in myeloid leukemia and produces a new member of the PR domain family. Proc Natl Acad Sci USA 93, 1642-1647), full-length EVI1 and EVI1$^{Del190-515}$ (similar to the identified Δ324 isoform isolated from human endometrial carcinoma cells; Kilbey, A. & Bartholomew. 1998. Evi-1 ZF1 DNA binding activity and a second distinct transcriptional repressor region are both required for optimal transformation of Rat1 fibroblasts. Oncogene 16, 2287-2291; Morishita, et al. 1990. Unique expression of the human Evi-1 gene in an endometrial carcinoma cell line: sequence of cDNAs and structure of alternatively spliced transcripts. Oncogene 5, 963-971). These $As_2O_3$ induced effects are similar to effects in leukemia cell lines (Shackelford, et al. 2006. Targeted degradation of the AML1/MDS1/EVI1 oncoprotein by arsenic trioxide. Cancer Res 66, 11360-11369). In contrast to these effects, $As_2O_3$ significantly increased SnoN/SkiL levels, also amplified at the 3q26.2 locus in ovarian cancers (Nanjundan, et al. 2007. Overexpression of SnoN/SkiL, amplified at the 3q26.2 locus, in ovarian cancers: A role in ovarian pathogenesis. Molecular Oncology 2(2), 164-81). Other TGFβ signaling mediators that are markedly reduced by $As_2O_3$ treatment include (1) TAK1 which can phosphorylate SnoN targeting it for degradation (Kajino, et al. 2007. TAK1 MAPK kinase kinase mediates transforming growth factor-beta signaling by targeting SnoN oncoprotein for degradation. J Biol Chem 282, 9475-9481 (2007)), (2) SMAD2/3, (3) TGFβRII which is down-regulated in advanced ovarian carcinomas relative to normal epithelium (Sunde, J. S., et al. 2006. Expression Profiling Identifies Altered Expression of Genes That Contribute to the Inhibition of Transforming Growth Factor-{beta} Signaling in Ovarian Cancer. Cancer Res 66, 8404-8412) (western analysis shows multiple bands likely reflecting heterogeneity of the receptor), and (4) AKT, which can signal through the TGFβ pathway by binding to SMAD3 (Conery, et al. 2004. Akt interacts directly with Smad3 to regulate the sensitivity to TGF-β induced apoptosis. Nat Cell Biol 6, 366-372).

Figure 13:
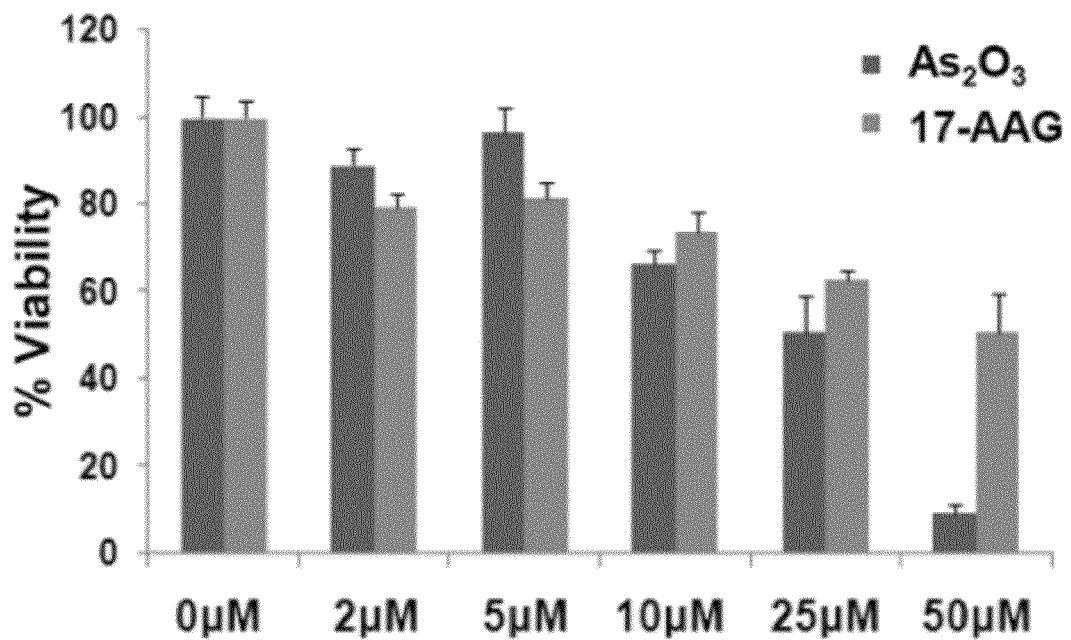
FIG. 13 is a graph showing the cell viability of ovarian cancer cells after 18 hour-treatment with $As_2O_3$ or 17-AAG. Viability was assessed using the Cell titer glo assay, with results presented as % cell viability relative to control cells (0 μM).

In contrast to these marked effects with $As_2O_3$, 17-AAG induced only a slight decrease in expression of certain EVI1 forms and SnoN with more marked reductions in TGFβRII, SMAD2/3, and AKT. Nonetheless, both $As_2O_3$ and 17-AAG had marked effects on cellular viability at 25 μM reducing cell growth by 50% and 63%, respectively as seen in FIG. 13.

Figure 14:
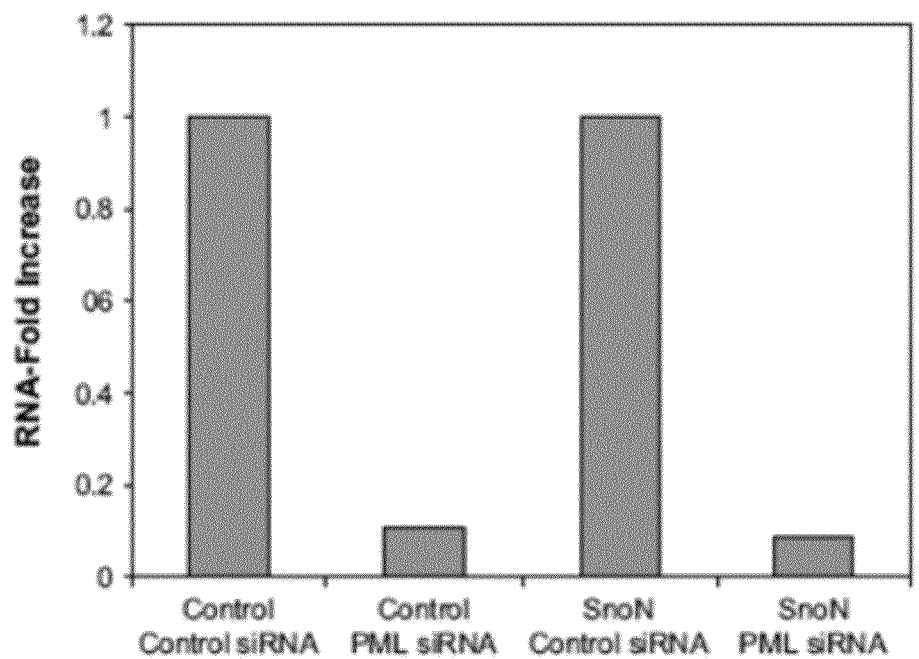
FIG. 14 is a graph showing knock-down of PML decreases SnoN-induced increases in p21 levels. Control and SnoN-EGFPF-11 cells were transfected with PML siRNA, and PML qPCR performed to measure RNA-fold changes.
Figure 15:
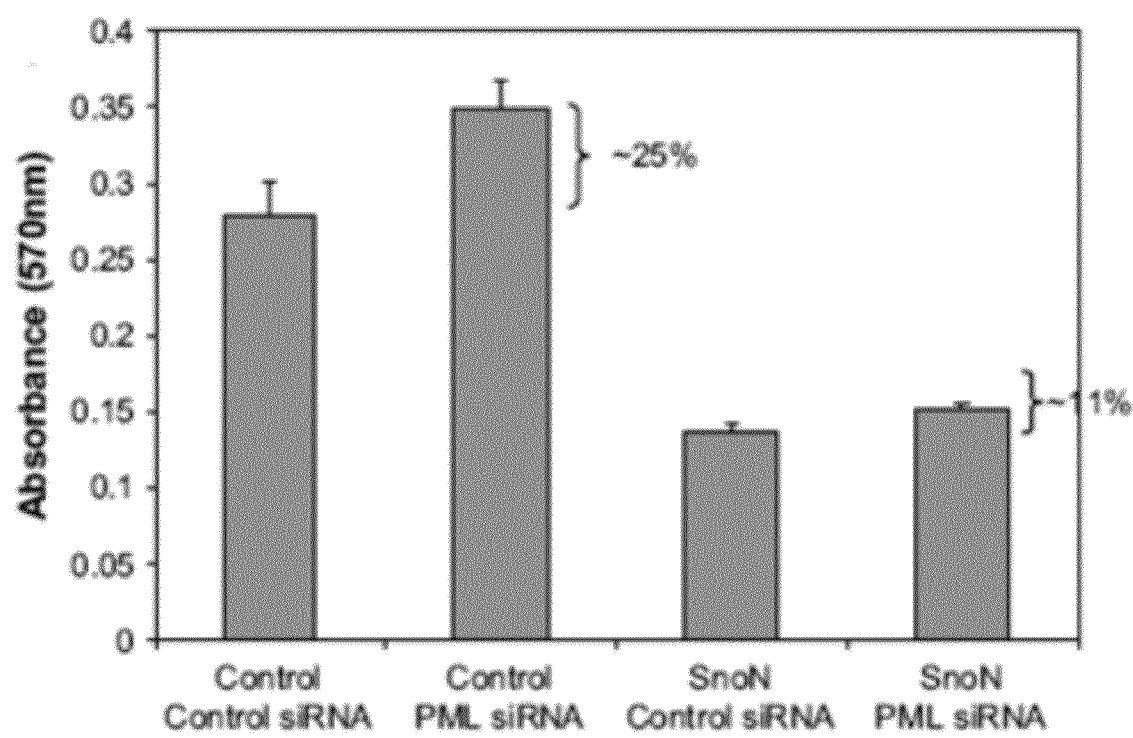
FIG. 15 is a graph showing growth rates for PML siRNA transfected cells. Control and PML siRNA treated TIOSE cells at 24 h post-transfection, were re-seeded on to 96 well plates at 5000 cells were well and allowed to grow for another 48 h, followed by MTS assay.

The localization of SnoN EGFP-fusion proteins was investigated in ovarian epithelial cells by transient expression of SnoN in T29 cells, data not shown. SnoN was found expressed exclusively in the nucleus in a distinct speckle-like distribution, data not shown. In an effort to address the nature of the nuclear speckles, coexpressed SnoN with PML (promyelocytic leukemia protein) which is a group of distinct nuclear subregions (Chelbi-Alix et al., 1995. Induction of the PML protein by interferons in normal and APL cells. Leukemia 9, 2027-2033). PML nuclear bodies are implicated in the regulation of transcription, apoptosis, senescence, and antiviral responses (Dellaire and Bazett-Jones, 2004. PML nuclear bodies: dynamic sensors of DNA damage and cellular stress. Bioessays 26, 963-977). PML is thought to regulate transcription, in part by mediating the assembly of complexes comprised of Ski (a related SnoN family member), Sin 3, and N-CoR/SMRT corepressors, together with histone deacetylases by which it may induce growth arrest, apoptosis, and senescence (Wilson et al., 2004. Crystal structure of the dachshund homology domain of human SKI. Structure 12, 785-792). SnoN localized to nuclear domains containing PML4, and colocalizes with other PML isoforms (PML1, 2, 3, and 5) but not to the same extent as with PML4, data not shown. This observed colocalization with PML suggests a potential functional relationship between PML and SnoN through which PML may regulate the ability of SnoN to mediate growth arrest. Significant differences were not observed in PML protein levels between control, as assessed by Western analysis, data not shown, and SnoN expressing or SnoN siRNA treated cells. Since p21 levels were dramatically elevated in cells stably expressing SnoN, and p21 could contribute to SnoN-mediated growth arrest or senescence, knockdown of PML was investigated to determine its effects of SnoN on p21 levels and thus, the observed growth arrest and senescence induced by SnoN. Reduction in PML RNA and protein levels (~60%), seen in FIG. 14, markedly decreased p21 levels in F-11 SnoN expressing cells indicating an essential role for PML in SnoN induction of p21, data not shown. In control T29 cells, p21 levels were only slightly reduced by PML siRNA suggesting that PML does not play a major role in the regulation of basal p21 levels but rather selectively mediates the effects of SnoN. Despite modest effects on p21 levels in control cells, PML siRNA increased proliferation to a greater extent in control cells (~25%) compared to SnoN expressing cells (~11%), seen in FIG. 15, despite the decrease in p21 levels induced by PML siRNA in SnoN expressing cells. Thus SnoN induced growth inhibition appears to proceed primarily through a PML and p21 independent pathway in immortalized, non-transformed, normal ovarian epithelial cells.

SnoN is regulated by sumoylation, which enhances the ability of SnoN to suppress transcription of p21 (Hsu et al., 2006. Sumoylated SnoN represses transcription in a promoter specific manner J. Biol. Chem. 281, 33008-33018). Modification of proteins by SUMO-1 is proposed to regulate specific protein-protein interactions, target proteins to specific subcellular compartments, and to prevent degradation by the ubiquitin-dependent pathway (Muller et al., 2004. SUMO: a regulator of gene expression and genome integrity. Oncogene 23, 1998-2008). Interestingly, many SUMO-1 conjugated proteins interact with PML as well as localize to PML nuclear bodies (Muller et al., 2004. SUMO: a regulator of gene expression and genome integrity. Oncogene 23, 1998-2008). However, knock-down of PML with siRNA did not significantly alter SnoN protein levels suggesting that in T29, PML does not regulate SnoN levels in immortalized normal ovarian epithelial cell, data not shown.

Example 3

Figure 16:
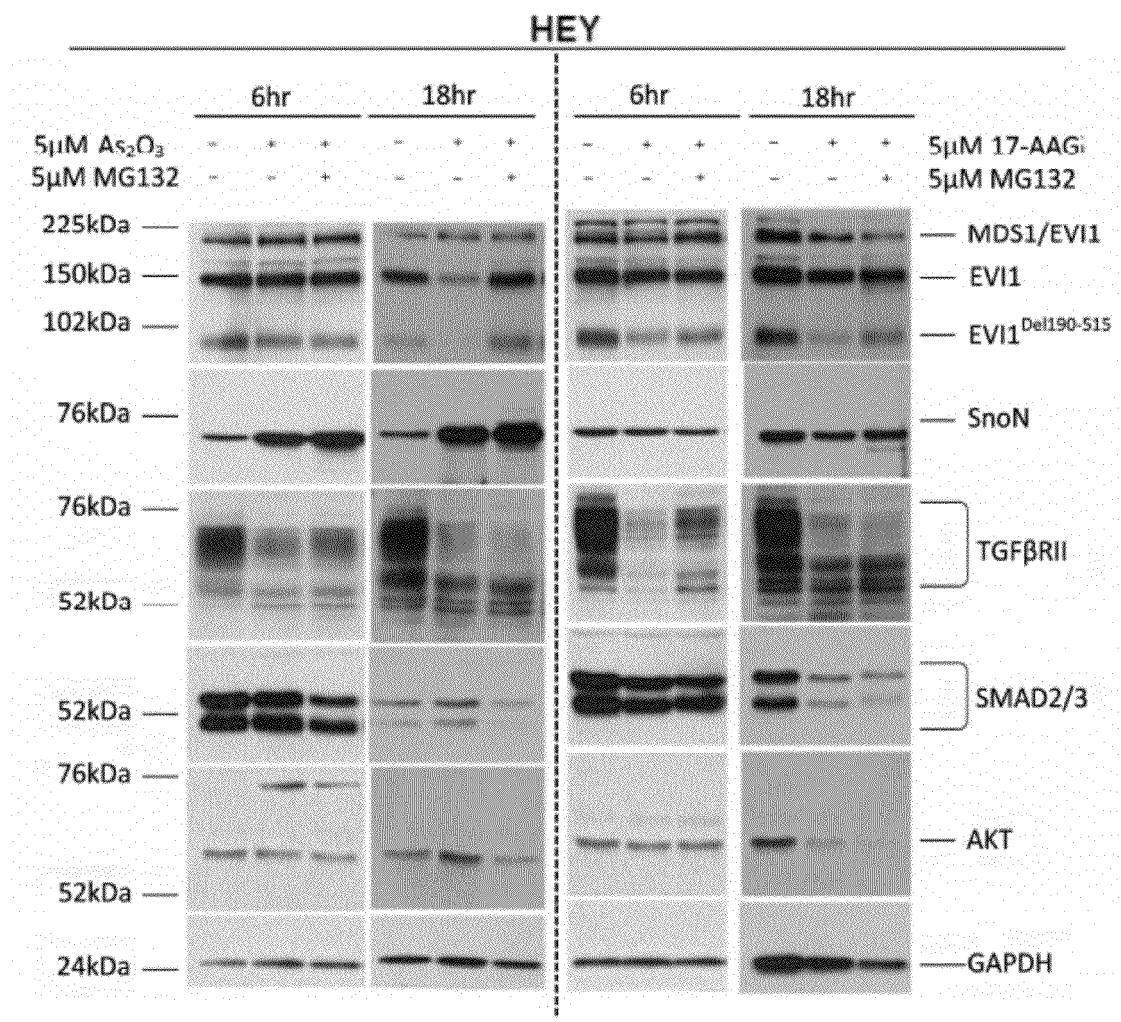
FIG. 16 is a Western blot showing dose response of $As_2O_3$ and 17-AAG in HEY ovarian cancer cells seeded at 250,000 cells per 6-well. After overnight attachment, the cells were treated with ASO and/or MG132 or 17-AAG and/or MG132.
Figure 17:
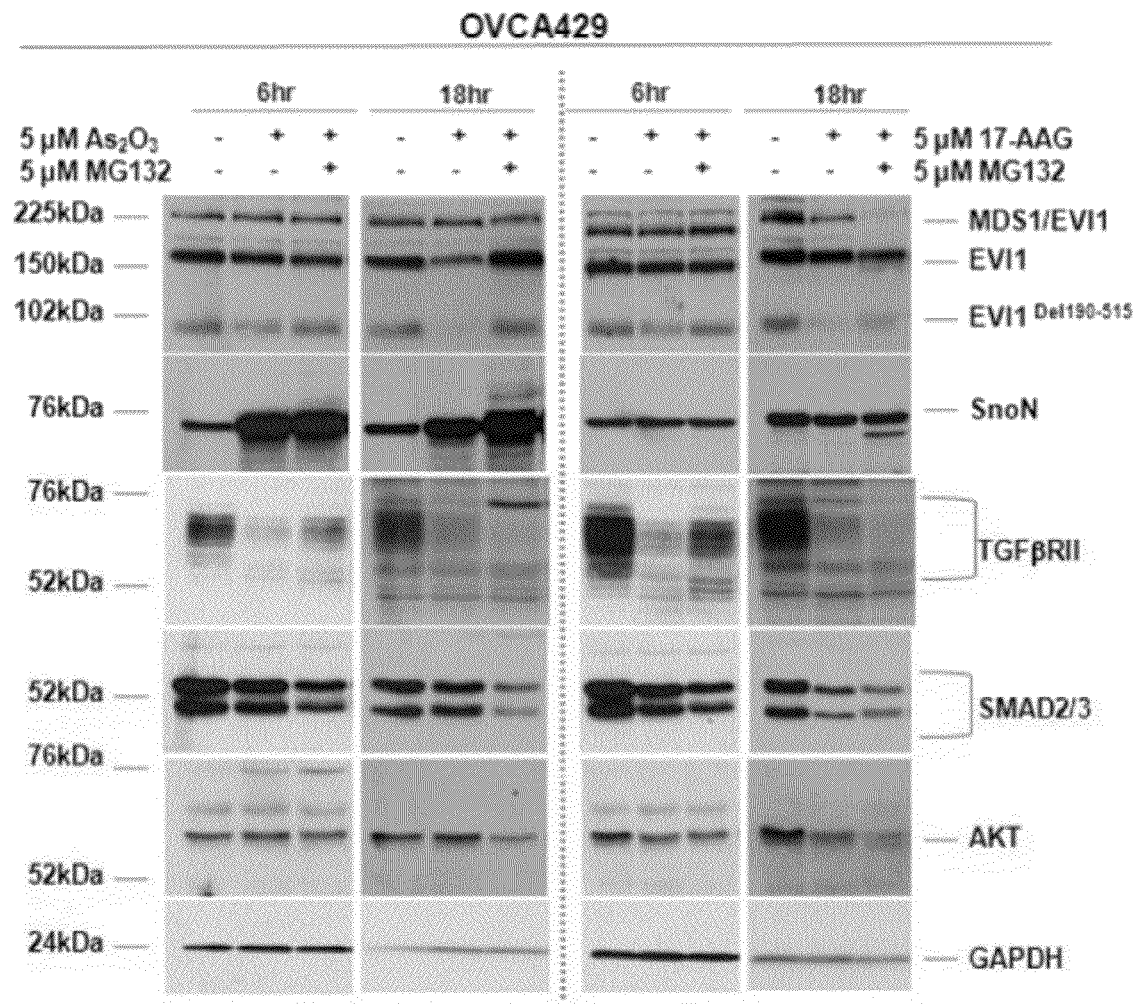
FIG. 17 is a Western blot showing dose response of $As_2O_3$ and 17-AAG in OVCA429 ovarian cancer cells seeded at 250,000 cells per 6-well. After 24 hours, the cells were treated at different time points with MG132 and Western analysis performed.
Figure 18:
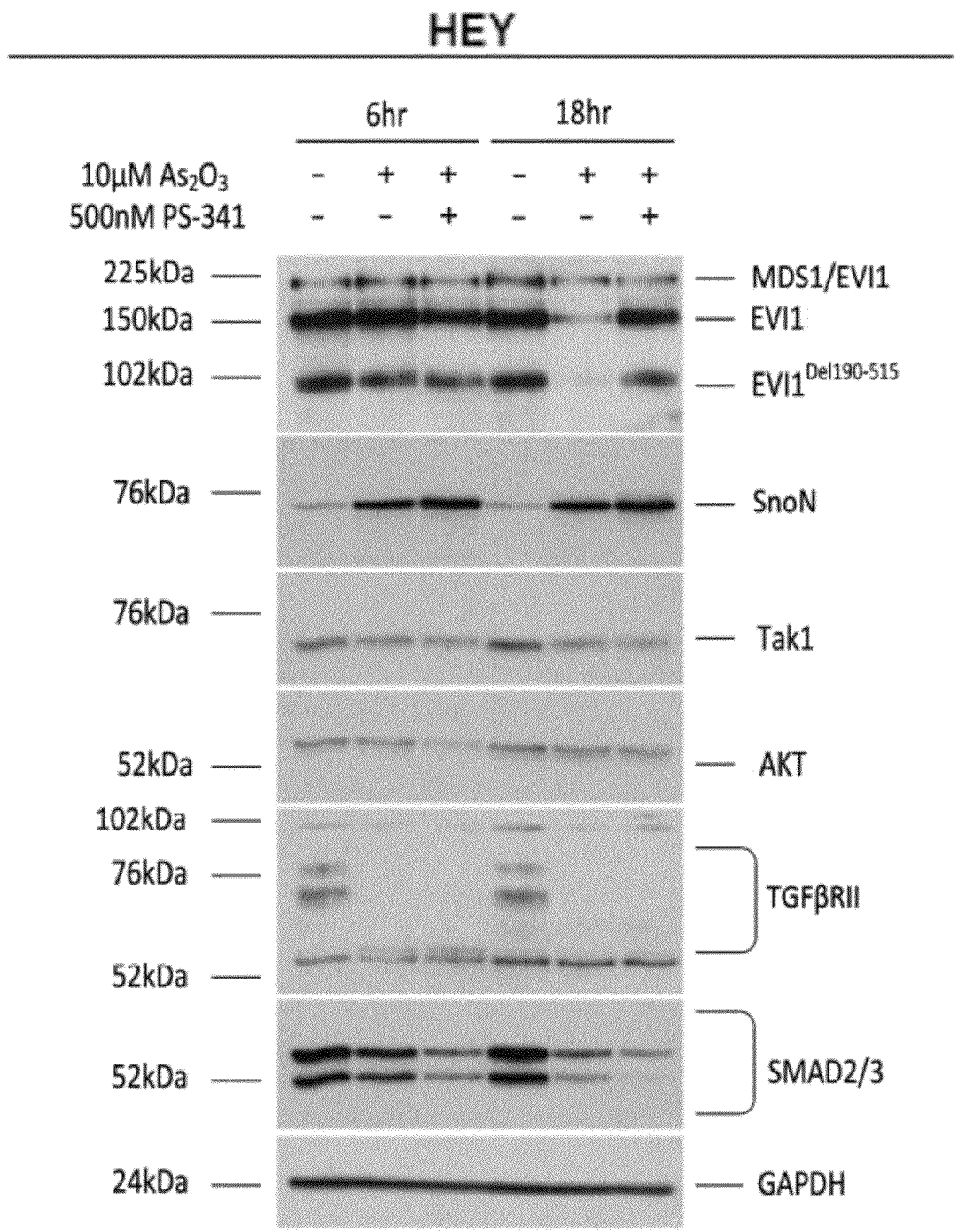
FIG. 18 is a Western blot showing dose response of $As_2O_3$ and 17-AAG in HEY ovarian cancer cells seeded at 250,000 cells per 6-well. After overnight attachment, the cells were treated with $As_2O_3$ and/or PS-341, for 18 hours, followed by Western analysis.

$As_2O_3$ Induces the Degradation of TGFβ Signaling Mediators Via Proteosome-Dependent and -Independent Pathways To determine whether the alterations in expression of TGFβ signaling mediators following treatment with $As_2O_3$ and 17-AAG were due to proteosome-mediated degradation, combinatorial studies were performed using a proteosome inhibitor (MG132). Generally, the response of HEY and OVCA429 to these drug combinations were similar, seen in FIGS. 16 and 17. Both EVI1 and EVI1$^{Del190-515}$ protein expression were reduced with 5 μM $As_2O_3$ while MDS1/EVI1 remained unchanged supporting previously reported data in murine leukemia cells, whereas MDS1 was insensitive to the effects of $As_2O_3$, seen in FIG. 16 (Shackelford, et al. 2006. Targeted degradation of the AML1/MDS1/EVI1 oncoprotein by arsenic trioxide. Cancer Res 66, 11360-11369). Interestingly, the reduction of EVI1 and EVI1$^{Del190-515}$ expression with $As_2O_3$ was recovered with the proteosome inhibitor MG132, suggesting that $As_2O_3$-induces the degradation of certain EVI1 forms through a proteosome-mediated pathway. Following 18 hour treatment with 5 µM 17-AAG, wild type EVI1 was not dramatically affected; however, MDS1/EVI1 and EVI1$^{Del190-515}$ were reduced and recovered with MG132, seen in FIG. 16. The increased sensitivity of EVI1 forms to $As_2O_3$ and 17-AAG following long-term treatments (18 hours) could be due to their inherent protein stability and long half-life. TGFβRII was recovered following 6 hour drug treatment with MG132, suggesting that both $As_2O_3$- and 17-AAG-induced degradation of TGFβRII can occur via a proteosome-mediated pathway. In addition, SnoN levels were further increased with MG132, suggesting that SnoN protein can be further stabilized via a proteosome-mediated pathway. Similar effects were observed with PS-341 (Bortezomid/Velcade) another proteosome inhibitor, which recovered EVI1 protein levels and further increased SnoN protein although TGFβRII levels did not appear to be recovered following PS341 treatment in contrast to MG132, seen in FIG. 18.

Figure 19:
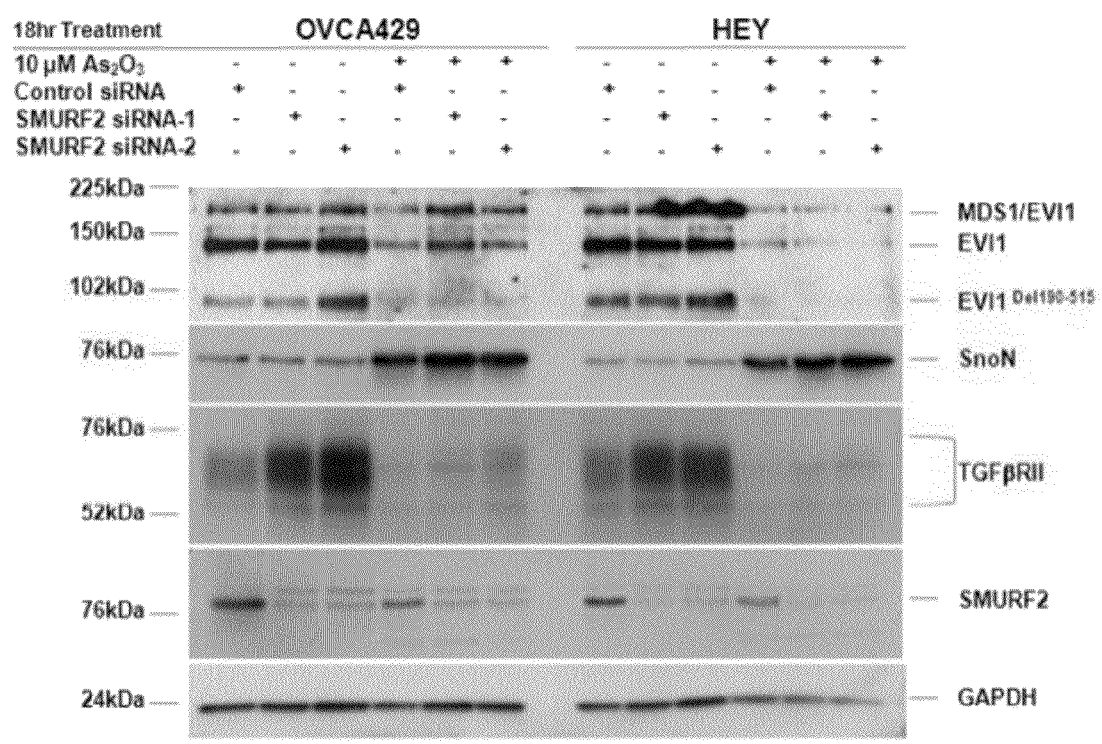
FIG. 19 is a Western blot showing dose response of $As_2O_3$ and 17-AAG in OVCA429 and HEY ovarian cancer cells seeded at 250,000 cells per 6-well. Cells were transfected with control non-targeting siRNA and two independent siRNAs against SMURF2, followed by 18 hour $As_2O_3$ treatment 24 hours post-transfection.

SMURF2 (an E3 ubiquitin ligase) is essential for 17-AAG induced TGFβRII degradation (Wrighton, et al. 2008. Critical regulation of TGF-β signaling by Hsp90. Proc Natl Acad Sci USA 105, 9244-9249). However, treatment of OVCA429 and HEY ovarian cancer cells with SMURF2 siRNA (>90% reduction in SMURF2 protein) did not significantly alter EVI1 SnoN, or TGFβRII protein in the absence or presence of $As_2O_3$, seen in FIG. 19, suggesting other E3 ubiquitin ligases involved in $As_2O_3$-induced degradation of TGFβRII, SnoN, or EVI1

Figure 20:
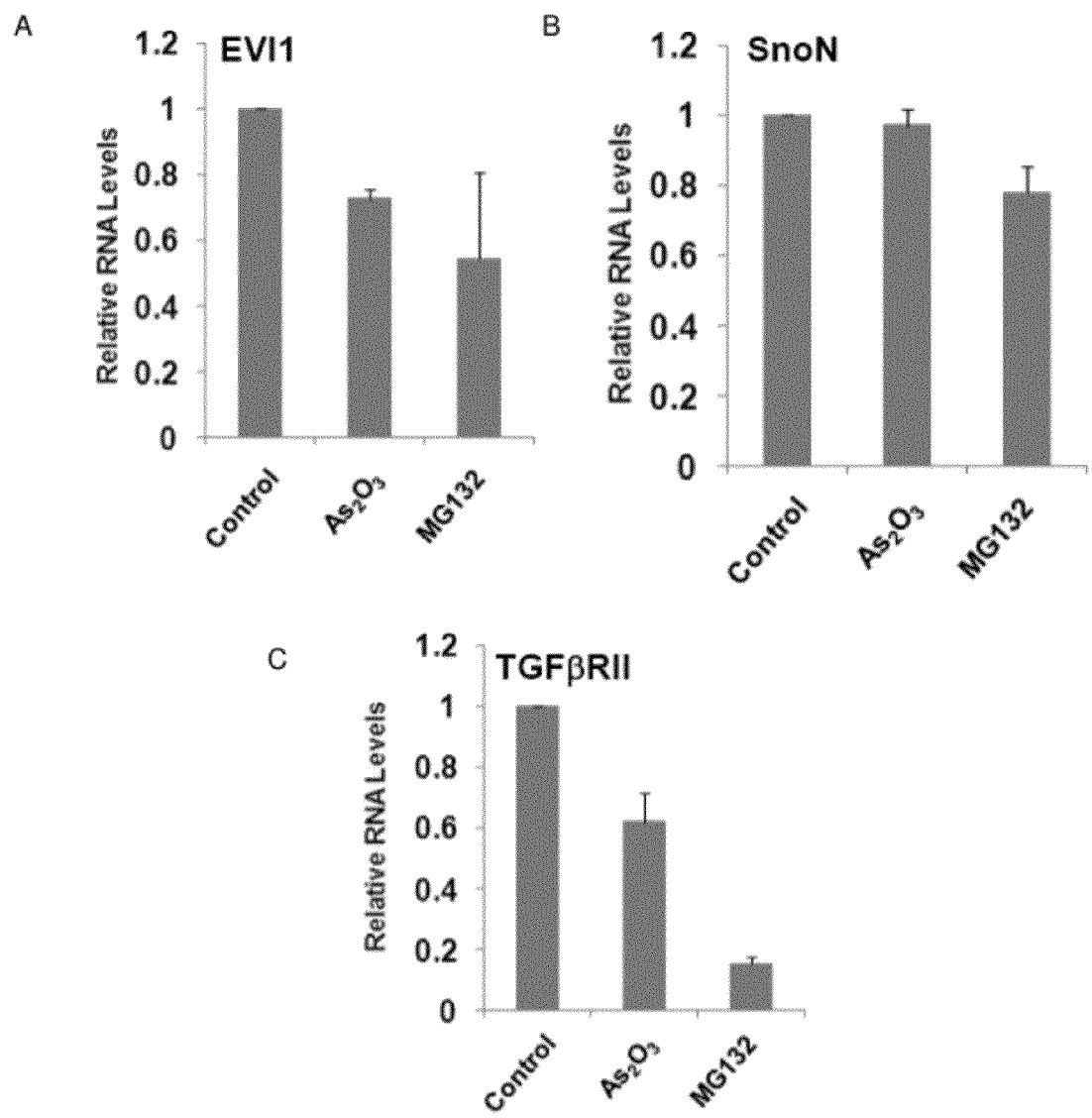
FIGS. 20(A) through (C) are graphs showing response of $As_2O_3$ and 17-AAG in HEY cells seeded at 500,000 cells per 6-well. Cells were treated with DMSO, 5 μM $As_2O_3$ and DMSO, or 5 μM MG132 for 18 hours, and qPCR performed from RNA isolates. Relative RNA-fold changes are presented for (A) EVI1, (B) SnoN, and (C) TGFβRII.
Figure 21:
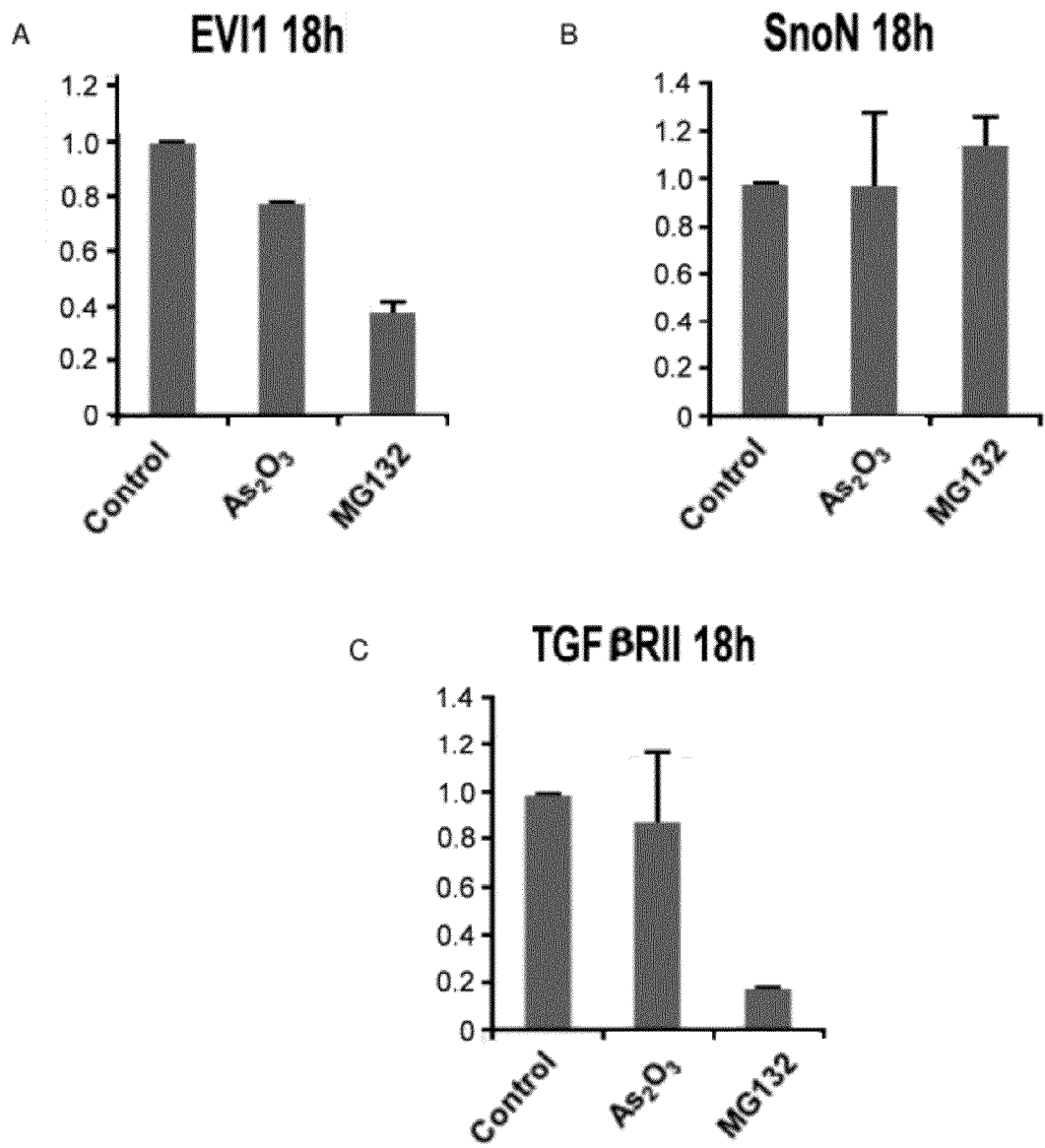
FIGS. 21(A) through (C) are graphs showing dose response of $As_2O_3$ and 17-AAG in OVCA429 ovarian cancer cells seeded at 500,000 cells per 6-well. Cells were treated with DMSO (control), 5 μM As$_2$O$_3$ and DMSO, or 5 μM MG132 for 18 hours, and qPCR performed from RNA isolates. Relative RNA-fold changes are presented for (A) EVI1, (B) SnoN, and (C) TGFβRII.
Figure 22:
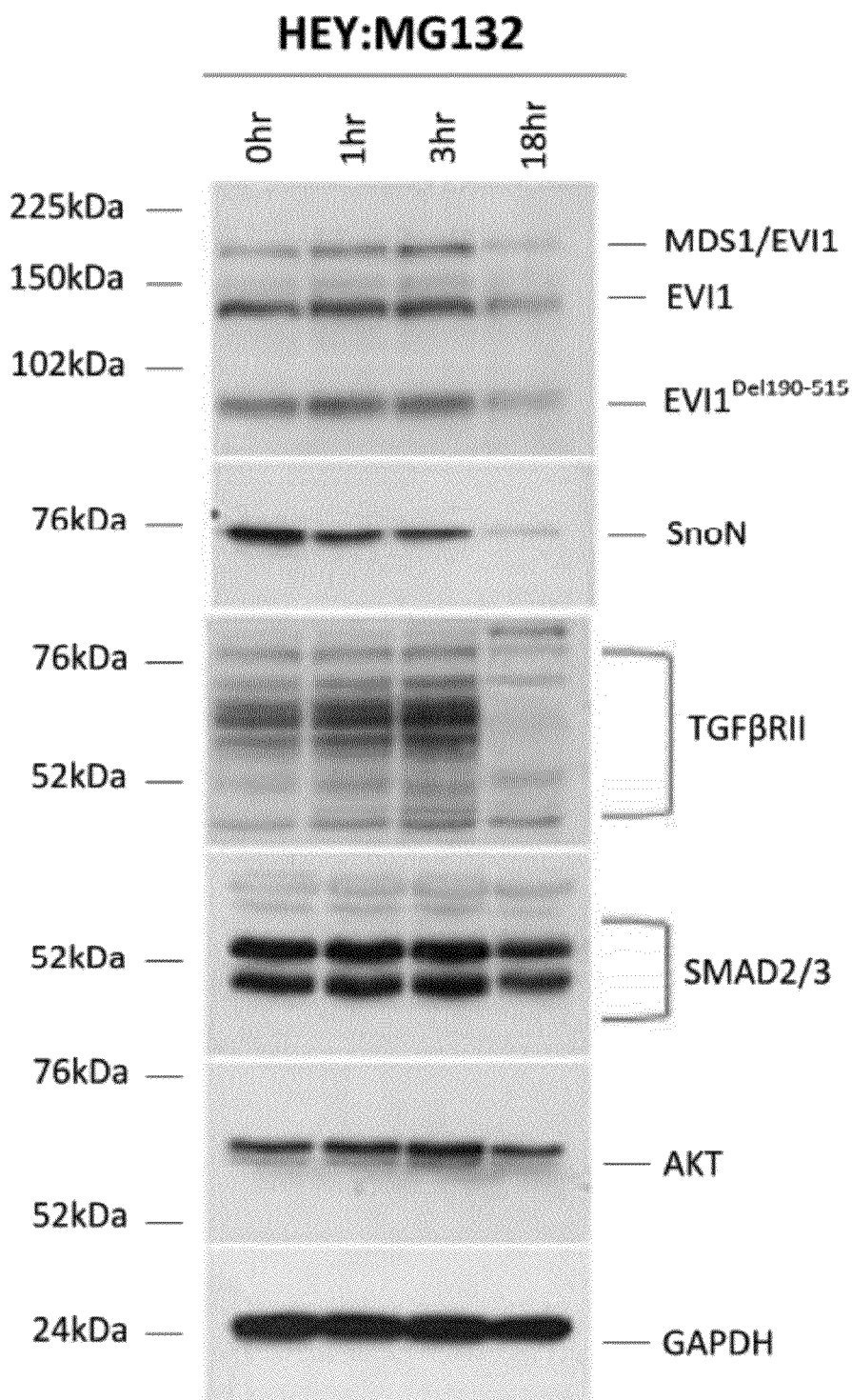
FIG. 22 is a Western blot showing dose response of As$_2$O$_3$ and 17-AAG in HEY ovarian cancer cell line seeded at 250,000 cells per 6-well. Cells were treated at different time points (1, 3, 18 h) with 5 μM MG132 and Western analysis was performed.

$As_2O_3$-induced alterations were then assessed in AKT, SMAD2/3, and TGFβRII protein with MG132 to determine changes to (1) protein expression independent of the proteosome or (2) RNA levels, seen in FIG. 22. MG132 treatment at 18 hours does not only significantly decreased their protein levels but also markedly reduce EVI1 and TGFβRII RNA levels, seen in FIGS. 20 and 21. Thus, MG132 can decrease protein expression by proteosome-independent mechanisms potentially by inhibition of protein translation, inhibition of RNA transcription, and induction of mRNA degradation. The effect of $As_2O_3$ on RNA levels, seen in FIG. 20, was also examined, since $As_2O_3$ can alter RNA expression such as survivin (Cheng, et al. 2008. Arsenic trioxide induced the apoptosis of laryngeal cancer via down-regulation of survivin mRNA. Auris, nasus, larynx 35, 95-101; Wu, et al. 2004. Arsenic trioxide inhibits proliferation in K562 cells by changing cell cycle and survivin expression. Journal of Huazhong University of Science and Technology. 24, 342-344, 353). However, a<20% decrease was observed in EVI1 and TGF-βRII RNA levels with little effect on SnoN RNA suggesting $As_2O_3$-induced changes in expression occurs to a major degree mostly at the protein level.

Example 4

Figure 23:
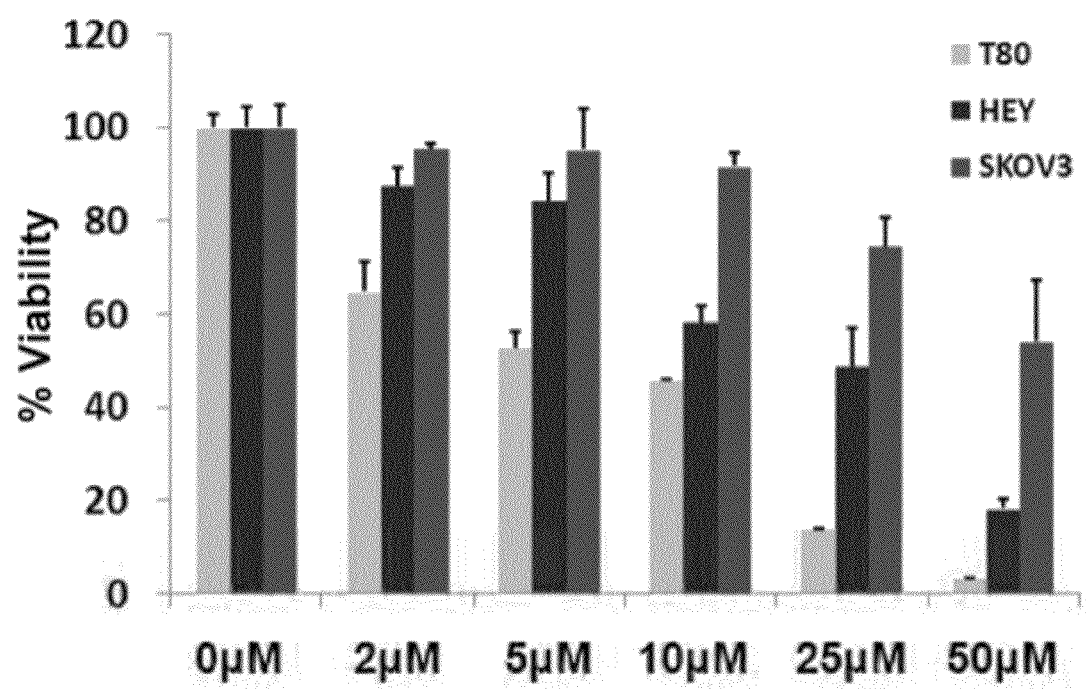
FIG. 23 is a graph showing arsenic trioxide induces cell death and inhibits migratory potential. Cell viability was assessed using the Cell titer glo assay in T80, HEY, and SKOV3 cells treated for 18 hours with varying doses (2-50 μM) As$_2$O$_3$. Results are presented as % cell viability relative to control cells (0 mM).
Figure 24:
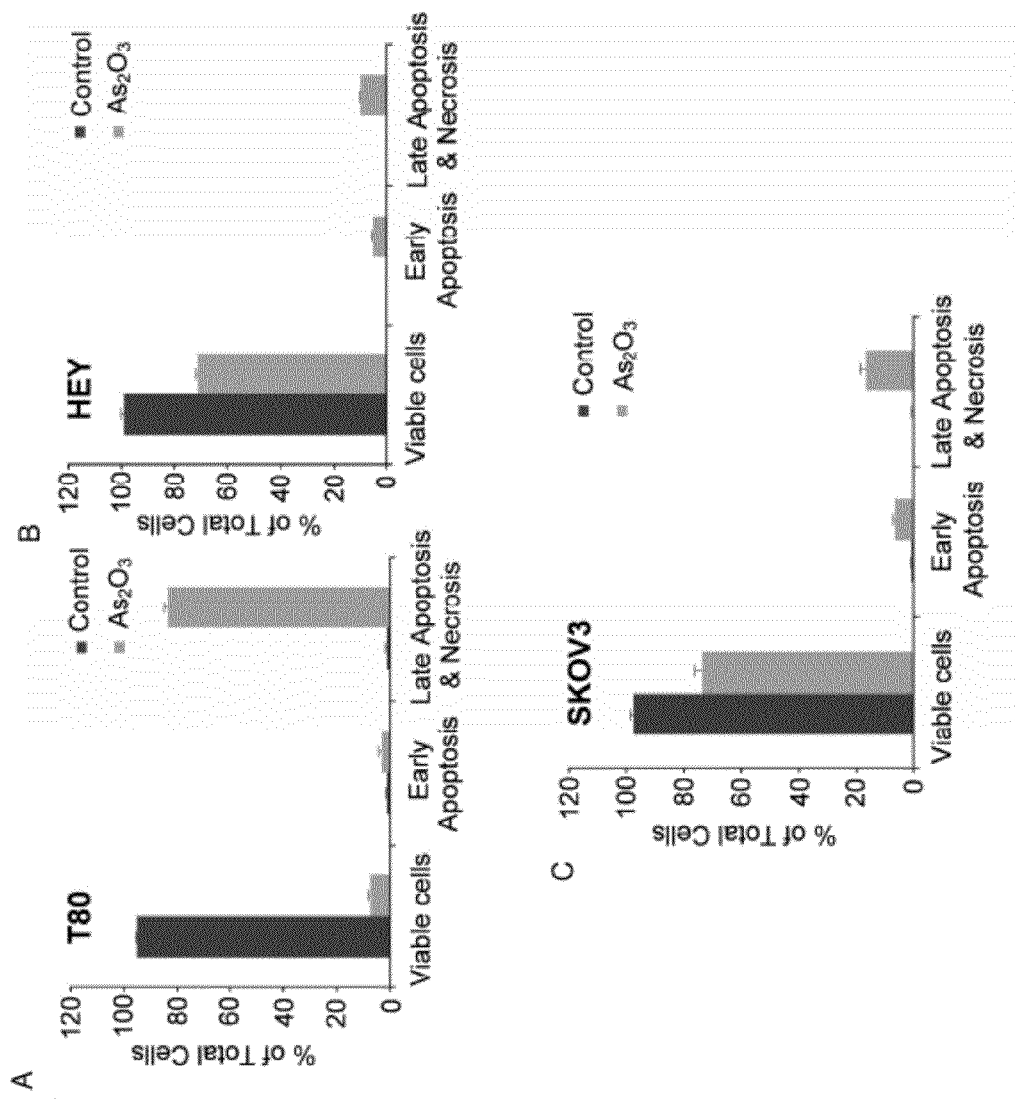
FIGS. 24(A) through (C) are graphs showing arsenic trioxide induces cell death and inhibits migratory potential, seen as a % total number of viable, early apoptotic, and late apoptotic/necrotic cells for (A) T80, (B) HEY, and (C) SKOV3.
Figure 25:
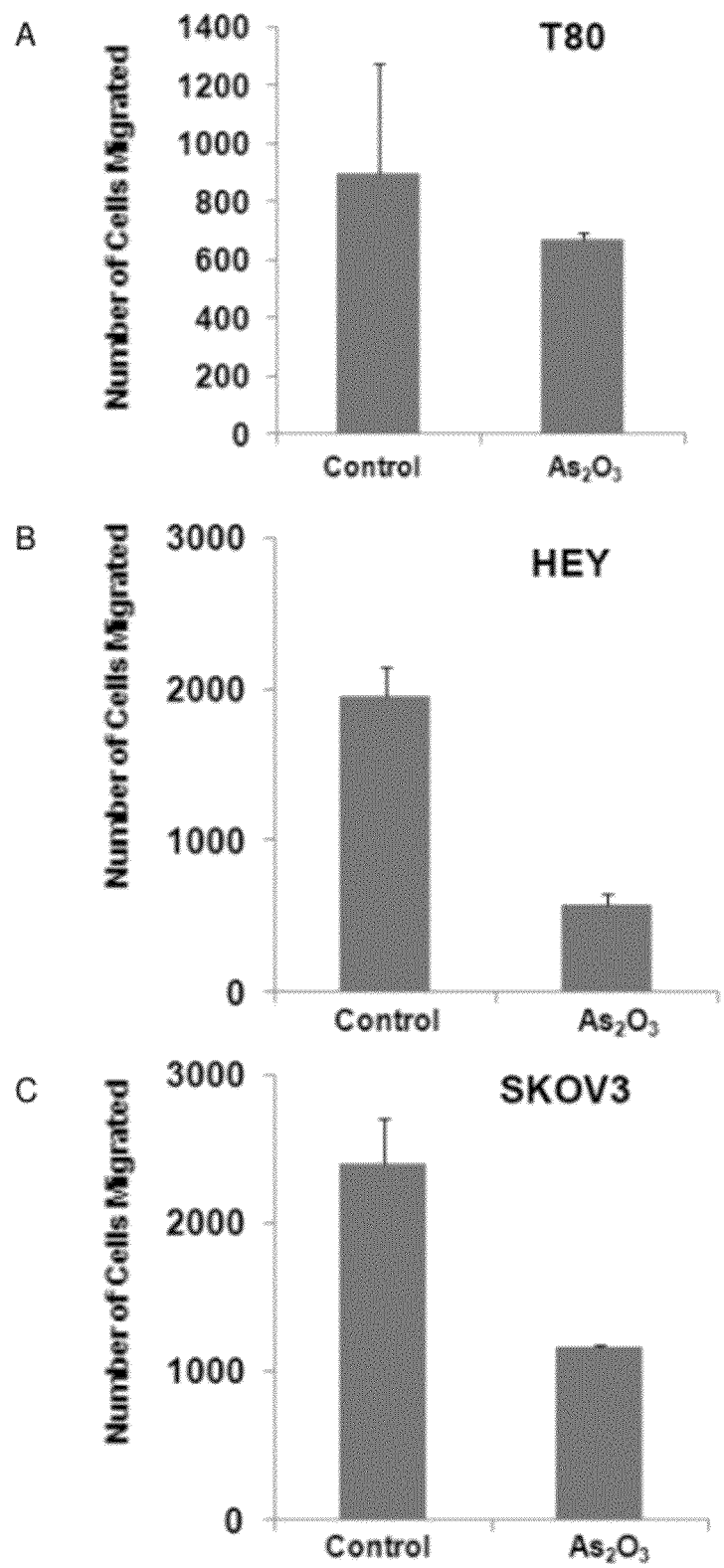
FIGS. 25(A) through (C) are graphs showing arsenic trioxide induces cell death and inhibits migratory potential. HEY cells were treated for 6 hours with 5 μM As$_2$O$_3$ and seeded at 25,000 cells into Boyden chamber inserts for 18 hours. Cells were stained with crystal violet and counted. The results are displayed as number of cells migrated in the absence and presence of As$_2$O$_3$.

$As_2O_3$ Alters Ovarian Cell Survival, Apoptosis, Autophagy, and Migration $As_2O_3$ induces autophagy, apoptosis, and necrosis in tumor cells of hematological origin and those from solid tumors such as small cell lung cancer cells (Pettersson, et al. 2009. Arsenic trioxide is highly cytotoxic to small cell lung carcinoma cells. Mol Cancer Ther 8, 160-170). In order to examine the functional effects of $As_2O_3$ on both normal and ovarian cancer cells, the effects of this drug were assessed on cell growth. The cells lines assessed include (1) T80, a large T antigen/hTERT immortalized normal ovarian surface epithelial cell line (a low expressing EVI1 cell line), (2) HEY (moderate expressing EVI1 cell line), and (3) SKOV3, an ovarian carcinoma cell line with an amplification at the EVI1 region (Nanjundan, et al. 2007. Amplification of MDS1/EVI1 and EVI1, located in the 3q26.2 amplicon, is associated with favorable patient prognosis in ovarian cancer. Cancer Res 67, 3074-3084). The expression profile of EVI1 was previously reported in these ovarian cell lines (Nanjundan, et al. 2007. Amplification of MDS1/EVI1 and EVI1, located in the 3q26.2 amplicon, is associated with favorable patient prognosis in ovarian cancer. Cancer Res 67, 3074-3084). Investigation of the effects of $As_2O_3$ treatment on cellular viability, seen in FIG. 23, indicated that high expressing EVI1 ovarian cell lines (SKOV3) were more resistant to the effects of $As_2O_3$ compared to low EVI1 expressing cell lines (T80 cells). Upon microscopic examination of the cells, the ovarian cell lines were undergoing apoptosis as evidenced by the presence of membrane blebbing, apoptotic bodies, and nuclear breakdown, data not shown. In addition, the development of numerous cytoplasmic vacuoles was observed in the HEY ovarian carcinoma cell line. Staining with annexin V-FITC and propidium iodide (PI) to quantify changes in apoptosis following $As_2O_3$ treatment, indicated that the low expressing EVI1 cell line (T80) had a markedly higher apoptotic percentage (>80%) compared to the ovarian cancer cell lines (SKOV3 and HEY; <20%, seen in FIG. 24. Thus, the sensitivity of ovarian cell lines to arsenic trioxide appears to correlate with EVI1 expression levels. In addition to the role of $As_2O_3$ in modulating the migratory potential of cervical and nasopharyngeal cells (Du, et al. 2006. Arsenic trioxide reduces the invasive and metastatic properties of nasopharyngeal carcinoma cells in vitro. Brazilian journal of medical and biological research 39, 677-685; Park, et al. 2005. Arsenic trioxide (As2O3) inhibits invasion of HT1080 human fibrosarcoma cells: role of nuclear factor-kappaB and reactive oxygen species. J Cell Biochem 95, 955-969), $As_2O_3$ reduced the migratory potential of both immortalized and cancer cell lines by more than fifty percent, seen in FIG. 25.

Example 5

Figure 26:
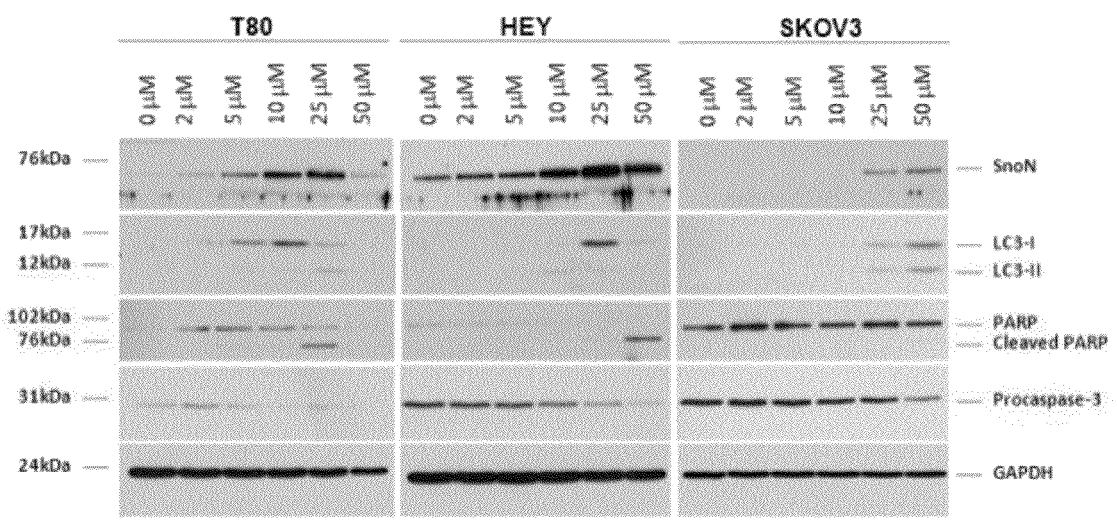
FIG. 26 is a Western blot showing arsenic trioxide mediates its effects on expression of TGFβ signaling mediators by generating reactive oxygen species. Cells were seeded at 250,000 cells per 6-well overnight, followed by treatment with arsenic trioxide, As$_2$O$_3$, for 18 hours and Western analysis.

$As_2O_3$ Mediates its Effects in Ovarian Cells Via the Generation of Reactive Oxygen Species The different sensitivities amongst the three ovarian cell lines (T80, HEY, and SKOV3) to $As_2O_3$ suggested that the signaling response to the drug may be altered. Indeed, induction of SnoN, seen in FIG. 26, occurred at 10 µM in T80 cells, >25 µM in HEY and SKOV3 cells which correlates with their sensitivity to $As_2O_3$, seen in FIG. 26. Since the numerous cytoplasmic vacuoles that developed with $As_2O_3$ treatment was suggestive of induction of autophagy, protein expression was examined for microtubule-associated protein light chain 3 (LC3), a phenotypic marker of autophagic vesicle formation. Interestingly, $As_2O_3$ increased levels of both the LC3-I (cytosolic form, 18 kDa) and LC3-II (membrane-bound form, 16 kDa) which correlated with SnoN expression, seen in FIG. 26. In addition, poly (ADP-ribose) polymerase (116 kDa, PARP), which is proteolytically fragmented to 89 and 24 kDa (an early marker of apoptosis) by caspase-3 which preceeds DNA fragmentation, dramatically increased at a dose of 25 µM (T80) and 50 µM (HEY and SKOV3) correlating with the apoptotic sensitivity determined by Annexin V staining, data not shown.

$As_2O_3$ treatment induces oxidative stress resulting in the accumulation of reactive oxygen species (ROS) by inhibition of glutathione peroxidase activity (Han, et al. 2008. Suppression of arsenic trioxide-induced apoptosis in HeLa cells by N-acetylcysteine. Molecules and cells 26, 18-25). To determine whether the changes observed in expression of TGFβ signaling mediators with $As_2O_3$ treatment are due to the effects of oxidative stress, ovarian cancer cells were treated with $As_2O_3$ in combination with the antioxidant N-acetyl-L-cysteine (NAC), a free radical scavenger/reducing agent and glutathione precursor which protects against $As_2O_3$-induced apoptosis in tumor cells (Han, et al. 2008. Suppression of arsenic trioxide-induced apoptosis in HeLa cells by N-acetylcysteine. Molecules and cells 26, 18-25). In contrast to $As_2O_3$ treatment alone, the addition of increasing doses of NAC markedly reduced SnoN expression with a corresponding recovery in EVI1 TAK1, and TGFβRII protein expression in HEY ovarian carcinoma cells, seen in FIG. 27. The results indicate that these changes in TGFβ signaling mediator expression with $As_2O_3$ can be altered by the presence of ROS.

Figure 28:
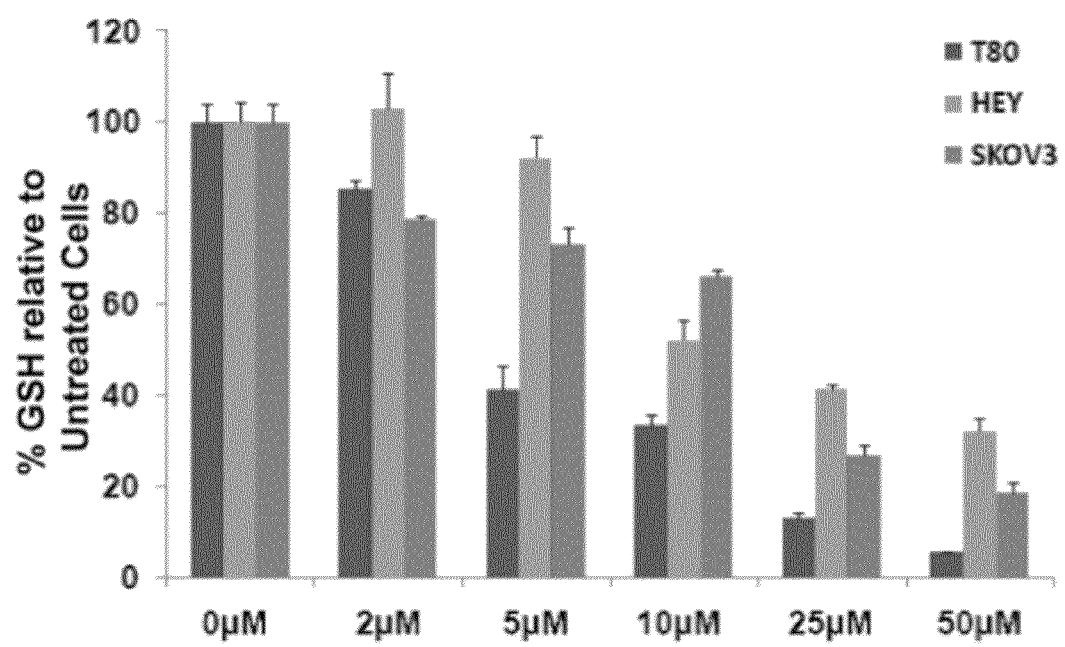
FIG. 28 is a graph showing arsenic trioxide mediates its effects on expression of TGFβ signaling mediators by generating reactive oxygen species. GSH levels were quantified in T80, HEY, and SKOV3 cells using the GSH-glo assay kit. Results are presented as % GSH relative to untreated cells.

Arsenic trioxide has been previously shown to reduce intracellular glutathione (GSH) levels (Davison, et al. 2003. Glutathione depletion overcomes resistance to arsenic trioxide in arsenic-resistant cell lines. Leukemia 17, 931-940). GSH levels were assessed in T80, HEY, and SKOV3 cells to determine whether there was any correlation with the sensitivity to arsenic trioxide, seen in FIG. 28. Although there was no significant difference in basal levels of GSH amongst these three cell lines, they had markedly reduced GSH levels following arsenic trioxide treatment. Since it has been reported that GSH binds to trivalent arsenic and is effluxed out of the cells through MRP1, the level of MRP1 protein expression were investigated in ovarian cell lines (Salerno, et al. 2002. The MRP1-mediated effluxes of arsenic and antimony do not require arsenic-glutathione and antimony-glutathione complex formation. J Bioenerg Biomembr 34, 135-145). Indeed, MRP1 was found highly expressed in SKOV3 cells (highly resistant to $As_2O_3$ mediated effects) and low in T80 and HEY cells (results not shown). Thus, high expression of MRP1 may lead to resistance to $As_2O_3$.

Example 6

$As_2O_3$ Induces Formation of Autophagosomes

Figure 29:
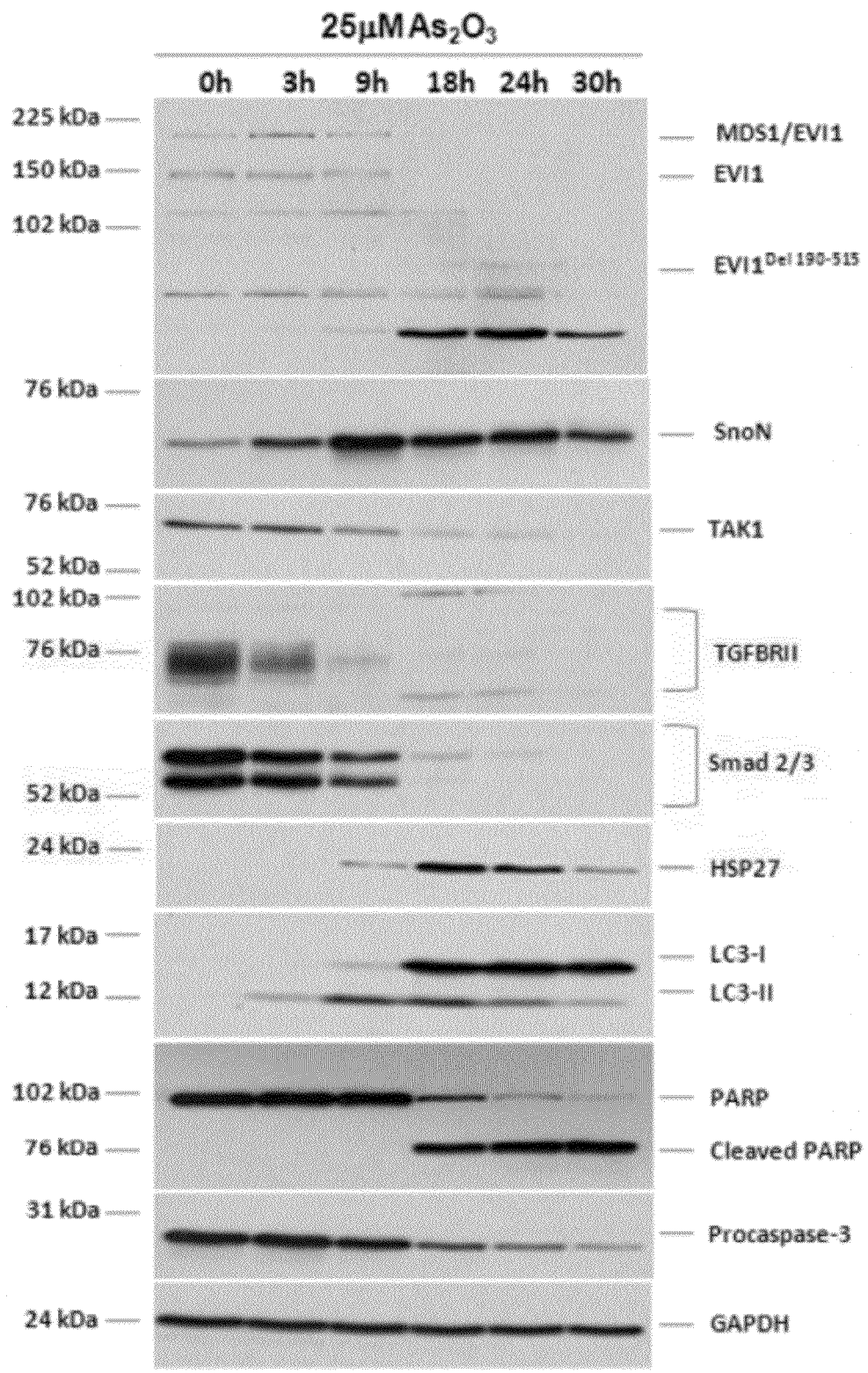
FIG. 29 is a Western blot showing time course studies of As$_2$O$_3$ treatment and identification of autophagosome by TEM. (b) HEY cells were seeded at 250,000 cells per well overnight, followed by treatment with As$_2$O$_3$. Cell lysates were harvested and western analysis was performed.

By light microscopy, dramatic development of cytoplasmic vacuoles was observed at 18 hours treatment followed by apoptosis, data not shown. Thus, a kinetic profile was performed to follow these events biochemically. Induction of SnoN was seen at 9 hour $As_2O_3$ treatment. SnoN levels were correlated with changes in LC3-II levels, a specific marker for autophagosome initiation and specifically targeted to phagophores. LC3-II is then reverted back to LC3-I likely by degradation and delipidation/recycling of the luminal and cytosolic-side bound pool of LC3-II, respectively during the generation of autolysosomes (Rubinsztein, et al. 2009. In search of an "autophagomometer". Autophagy 5, 585-589). Reduction in procaspase-3 and increased PARP cleavage at 18 hours correlated with the marked increases in the LC3-I levels, seen in FIG. 29. Dramatic decreases in EVI1, TAK1, SMAD2/3, TGFβRII expression levels were seen at 18 hours treatment, seen in FIG. 29. Induction of another potential splice variant of EVI1 seen in FIG. 29, (~60 kDa, detected using an antibody which detects multiple splice forms of EVI1) was observed, which follows HSP27 expression. Expression of heat shock protein, HSP27, was increased at 18 hours following SnoN induction possibly to elicit cytoprotective activity to protect against cellular stresses such as the apoptosis resulting from the effects of therapeutic drugs (Gamido, et al. 2003. HSP27 and HSP70: potentially oncogenic apoptosis inhibitors. Cell Cycle 2, 579-584).

Studies were performed to positively identify the presence of autophagosomes by transmission electron microscopy (TEM) which is the gold standard for identification of the autophagic process. TEM positively identified the presence of numerous double membrane autophagosomes with $As_2O_3$, data not shown. Following 3 hour $As_2O_3$ treatment, the formation of double membrane structures, phagophores or initiating membranes, were clearly observed. At 9 hours, the autophagosomes were fully formed and at 18 hours, there was clearing within autophagosomes suggesting degradation of the cytoplasmic contents. Beyond 18 hours, the cells underwent apoptosis (results not shown). In addition, EGFP-LC3 cDNA was transfected into HEY cells to identify fluorescent vacuoles following $As_2O_3$ treatment. A punctuate staining pattern around the nucleus was observed following $As_2O_3$ treatment between 5 μM to 25 μM, data not shown. Collectively, the results (western blotting of LC3 expression, TEM, and GFP-LC3) show that $As_2O_3$ induces the development of autophagosomes in parallel with levels of SnoN.

Figure 30:
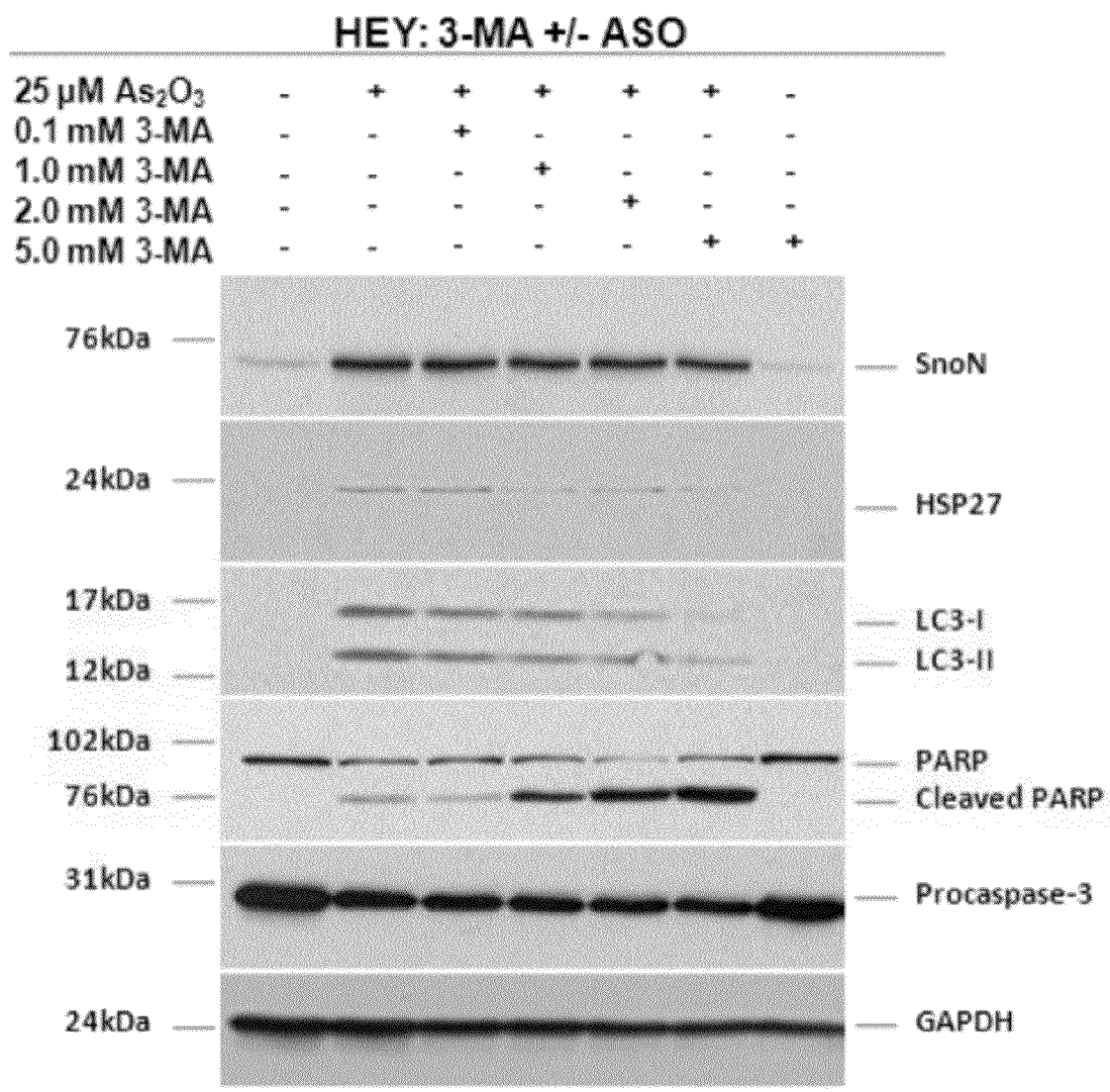
FIG. 30 is a Western blot showing autophagy as a cell survival mechanism. HEY cells were seeded at 250,000 cells per well for 24 hours, followed by treatment with As$_2$O$_3$ and/or varying concentrations of 3-MA for 18 hours. Cell lysates were harvested and western analysis was performed.

To determine whether autophagy is a necessary step in induction of cell death via $As_2O_3$, the effects of various inhibitors were tested for autophagy and apoptosis. 3-Methyladenine (3-MA) is a class III phosphatidylinositol-3-kinase (PI3K) inhibitor that prevents autophagy at the earliest stage of the autophagosome formation process (Hoang, et al. 2009. Effect of autophagy on multiple myeloma cell viability. Mol Cancer Ther 8, 1974-1984). Treatment with 3-MA is normally associated with decreased LC3-II expression and inhibition of autophagy (Hoang, et al. 2009. Effect of autophagy on multiple myeloma cell viability. Mol Cancer Ther 8, 1974-1984). Light microscopy images showed a noticeable reduction in the number of cytoplasmic vacuoles with 3-MA in the presence of $As_2O_3$ in contrast to HEY cells treated with $As_2O_3$ alone, data not shown. 3-MA not only reduced the formation of GFP-LC3 punctuate staining pattern, data not shown, and LC3-II/LC3-I levels in cells treated with $As_2O_3$ but further increased PARP cleavage (used as an early apoptotic marker), seen in FIG. 30. SnoN levels were not dramatically altered with 3-MA treatment suggesting that SnoN lies upstream to the effect of 3-MA in the autophagic pathway. HSP27 levels were also observed reduced dramatically following 3-MA treatment supporting its cytoprotective role towards apoptosis. These results indicate that 3-MA inhibits the autophagic process with a shift towards increased induction of apoptosis.

Figure 31:
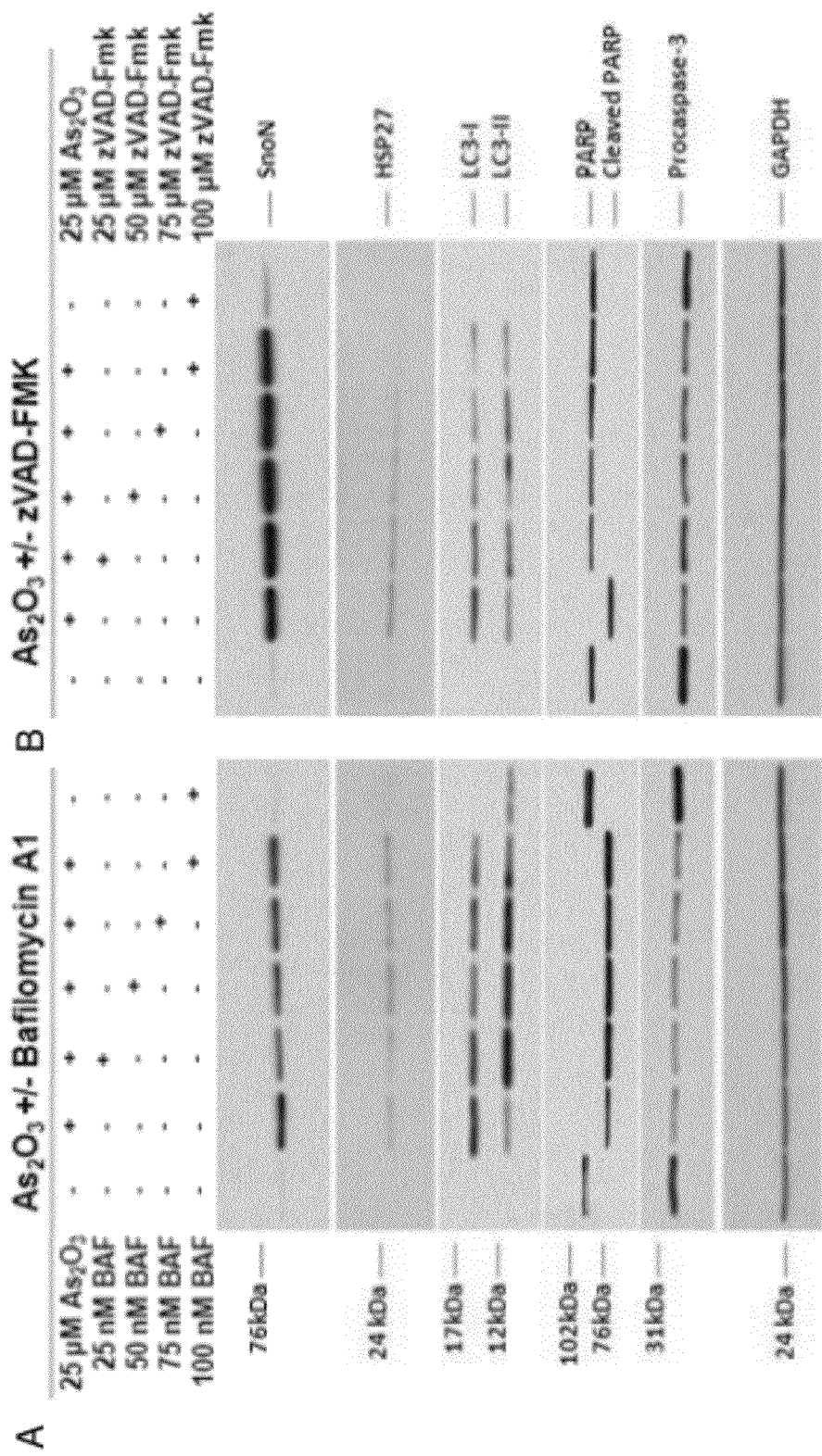
FIGS. 31(a) and (b) are Western blots showing autophagy as a cell survival mechanism. HEY cells were seeded at 250,000 cells per well for 24 hours, followed by treatment with (A) As$_2$O$_3$ and/or varying amounts of Bafilomycin A, or (B) As$_2$O$_3$ and/or varying amounts of zVAD-Fmk for 18 hours. Cell lysates were harvested and western analysis was performed.

The effect of Bafilomycin A, a late-stage autophagy inhibitor that inhibits the maturation of autolysosomes (fusion of lysosomes to autophagosomes) leading to inhibition of the degradation of the inner contents and an accumulation of uncleaved LC3-II protein which remains bound to the autophagophore (Wu, et al. 2009 Inhibition of macroautophagy by bafilomycin A1 lowers proliferation and induces apoptosis in colon cancer cells. Biochem Biophys Res Commun 382, 451-456) was investigated. Indeed, western analysis of HEY cells treated with $As_2O_3$ in the presence of Bafilomycin A1 showed increased LC3-II (membrane-bound form) and cleaved PARP levels, seen in FIG. 31(a). SnoN levels were slightly reduced with Bafilomycin A1 in the presence of arsenic trioxide suggesting a role for SnoN in this process. These results suggest that inhibition of late stage autophagy leads to increased apoptosis.

In addition, the effect of z-VAD-fmk, a caspase inhibitor which inhibits apoptosis (White, et al. 2008. Autophagic cell death unraveled: Pharmacological inhibition of apoptosis and autophagy enables necrosis. Autophagy 4, 399-401) were investigated. Although the levels of SnoN and LC3 remained unchanged with increasing concentrations of zVAD-fmk, seen in FIG. 31(b), cleaved PARP was dramatically reduced implicating a reduction in apoptosis. SnoN protein expression remained unchanged indicating it lies upstream to the effects of this inhibitor while HSP27 slightly decreased with increasing concentration of zVAD-fmk promoting its role as cytoprotective. Collectively, these inhibitor studies indicate that autophagy induced by $As_2O_3$ treatment confers a protective role against apoptosis which is the primary cell death mechanism induced by $As_2O_3$.

Figure 32:
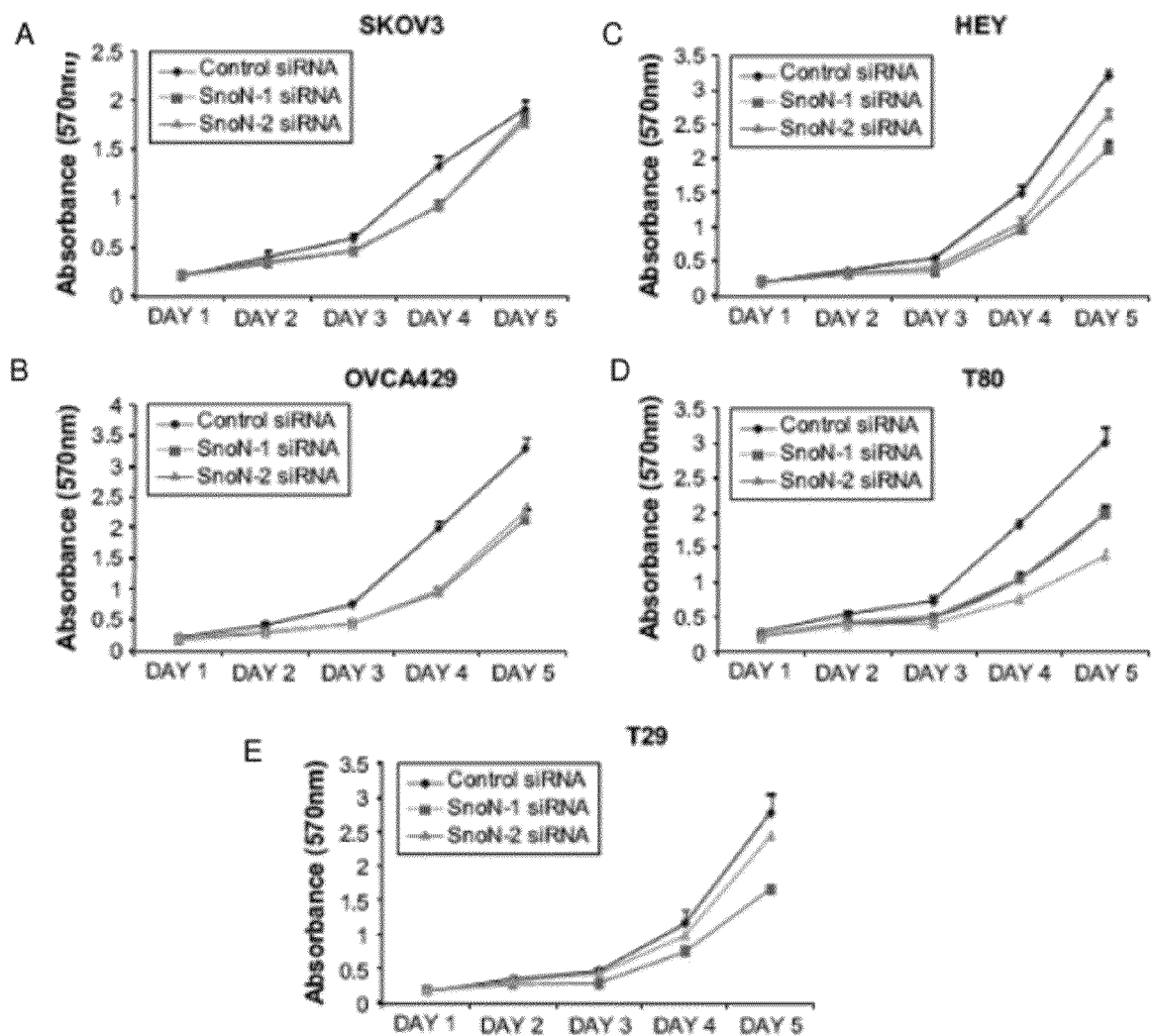
FIGS. 32(A) through (E) are graphs showing siRNA knockdown of SnoN alters normal immortalized ovarian epithelial and ovarian carcinoma cell growth, as assessed by staining with crystal violet and measured at absorbance of 570 nm. Cell lines tested were (A) SKOV3, (B) OVCAR429, (C) HEY, (D) T80, and (E) T259.

As indicated in the introduction, SnoN can act as an oncogene or tumor suppressor gene either promoting transformation or tumor suppression which may contribute to the well-established dual effects of TGF-β in tumor development (Elliott and Blobe, 2005. Role of transforming growth factor Beta in human cancer. J. Clin. Oncol. 23, 2078-2093; Liu et al., 2001. Ski/Sno and TGF-β signaling. Cytokine Growth Factor Rev. 12, 1-8). To investigate the role of SnoN in ovarian tumorigenesis, the effect of decreasing SnoN levels by siRNA were assessed in both immortalized normal (TIOSE: T29 and T80) and ovarian carcinoma cell lines (OVCAR8, SKOV3, HEY, and OVCA429) using multiple siRNAs. P21 protein levels were increased by SnoN knockdown, data not shown. Concordantly, SnoN knockdown conferred a consistent (20-50%) growth disadvantage in multiple ovarian cell lines, seen in FIG. 32. Moreover, SnoN shRNA failed to give rise to any puromycin resistant colonies when expressed in HEY, SKOV3, and T80 cells providing additional support that knockdown of SnoN inhibits cell growth. In addition to altered p21 levels, decreased plasminogen activator inhibitor-1 (PAI-1) protein was observed with SnoN knockdown, data not shown. PAI-1 has been reported to reduce cell migration and invasion in breast and gynecological cancer cells (Whitley et al., 2004. Expression of active plasminogen activator inhibitor-1 reduces cell migration and invasion in breast and gynecological cancer cells. Exp. Cell Res. 296, 151-162).

Further, SnoN has been proposed to decrease epithelial-mesenchymal transition (EMT) and motility in breast and lung cancer cell lines (Zhu et al., 2007. Dual role of SnoN in mammalian tumorigenesis. Mol. Cell. Biol. 27, 324-339). Thus, the ability of SnoN to regulate cellular motility of normal immortalized ovarian epithelial cells (T80, T29) was analyzed as well as ovarian carcinoma cell lines (SKOV3 and HEY) using siRNA against SnoN. However, no reproducible or consistent alteration was observed in cellular migration by reducing SnoN levels using multiple sources of siRNA (results not shown). Collectively, these results indicate that knockdown of SnoN reduces the growth of both normal and carcinoma ovarian cell lines with no dramatic effect on cellular migration.

Example 7

Figure 33:
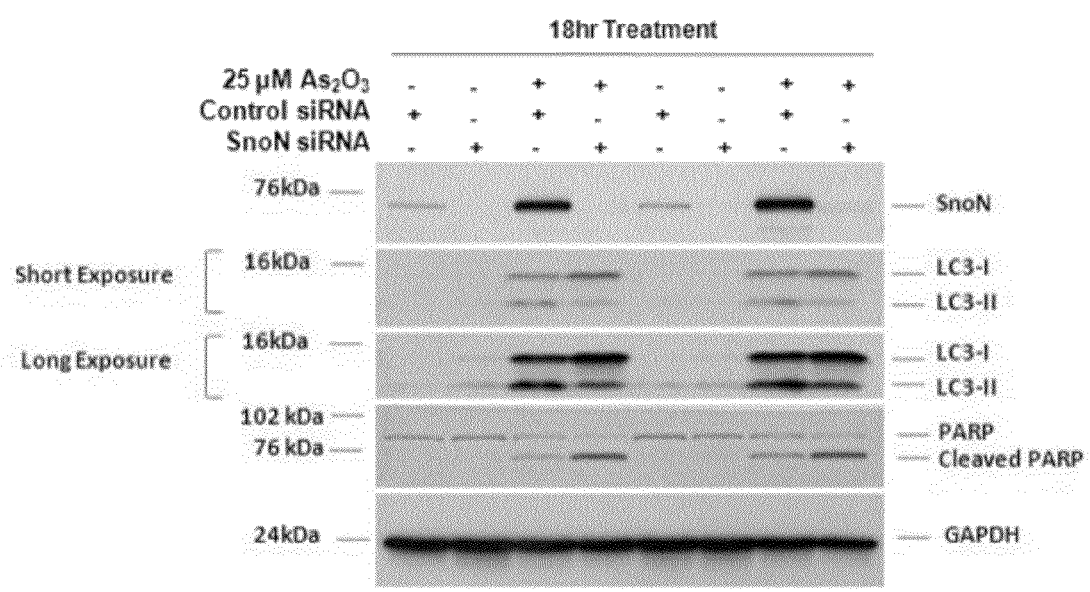
FIG. 33 is a Western blot showing knockdown of SnoN modulates the sensitivity of ovarian cancer cells to arsenic trioxide. HEY cells were seeded at 250,000 cells per 6-well plates for 24 hours, followed by transient transfection with non-targeting (control) siRNA or SnoN siRNA. Cells were treated with As$_2$O$_3$ 24 hours post-transfection, and western analysis was performed 18 hour after incubation.
Figure 34:
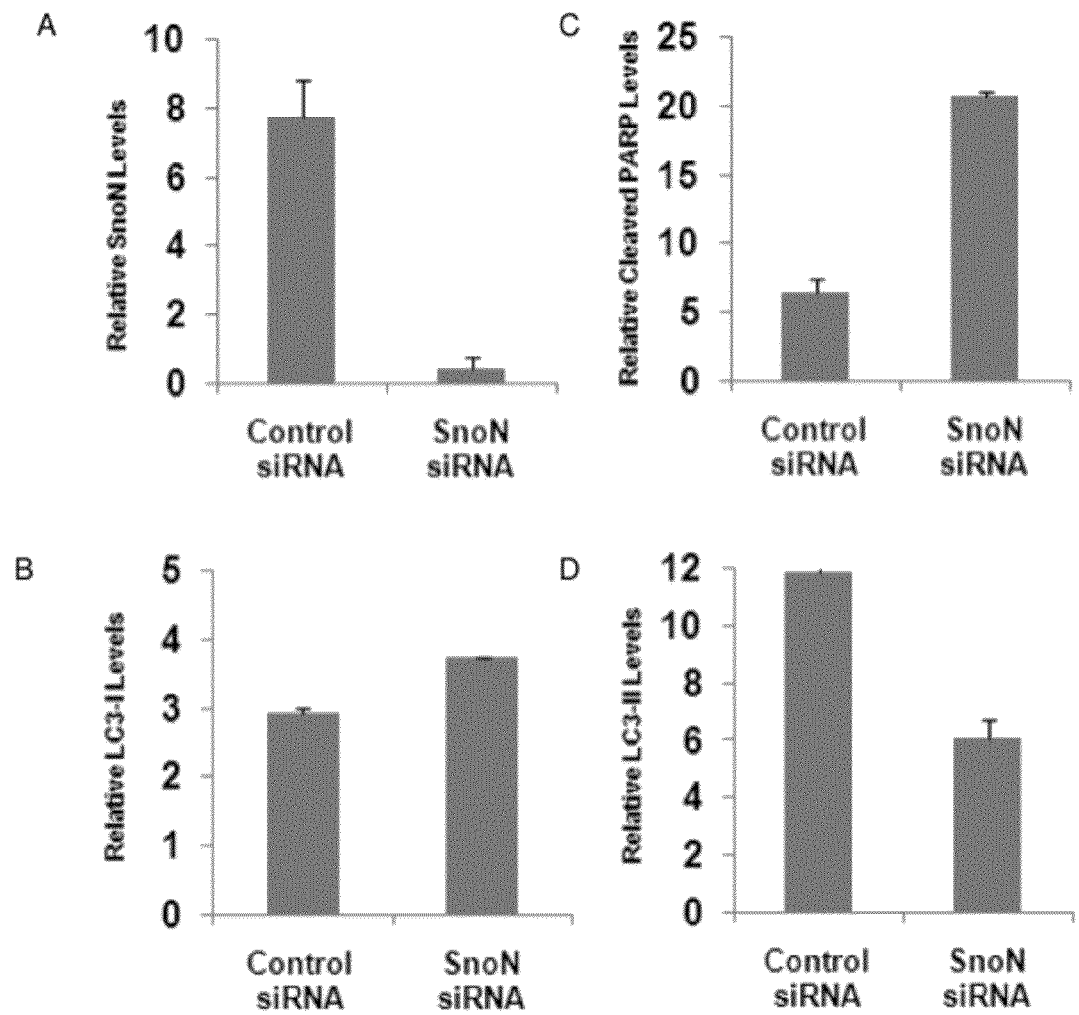
FIG. 34(A) through (D) are graphs showing densitometric analyses of selected data presented in FIG. 33. Samples displayed are arsenic trioxide treated samples only for (A) SnoN, (B) LC3-I, (C) cleaved PARP, and (D) LC3-II.

Modulation of the Sensitivity of Ovarian Cancer Cells to $As_2O_3$ by SnoN Knockdown Since SnoN levels were found to observe paralleled those of LC3, SnoN was investigated to determine if it could alter LC3-II levels. Knockdown of SnoN using siRNA did alter cleaved PARP levels and the LC3-II/I ratio, seen in FIGS. 33 and 34. qPCR measurements of LC3 RNA transcripts indicated that generally LC3 RNA transcripts are low and SnoN siRNA did not alter LC3 RNA transcript levels (results not shown). These results suggest alternative mechanisms other than direct transcriptional regulation of LC3 by SnoN. Since low and high expressing EVI1 ovarian cell lines differed in their response to the apoptotic effects of $As_2O_3$, seen in FIG. 23, the effect of EVI1 siRNA was assessed on the sensitivity of ovarian cancer cells to arsenic trioxide. However, EVI1 siRNA (Exon VII) did not dramatically alter $As_2O_3$ induced sensitivity to apoptosis based on PARP cleavage levels, seen in FIGS. 35 through 37. Knockdown of HSP27 (reduced HSP27 protein ~50%) also did not alter PARP cleavage whereas SnoN siRNA knockdown (reduced SnoN protein >90%) had a significant effect on PARP cleavage (~75% increase) following 6 hour treatment, seen in FIGS. 35 through 37. Thus, the sensitivity of ovarian cancer cells to $As_2O_3$-induced apoptosis and autophagy can be modulated by altering SnoN levels.

Figure 35:
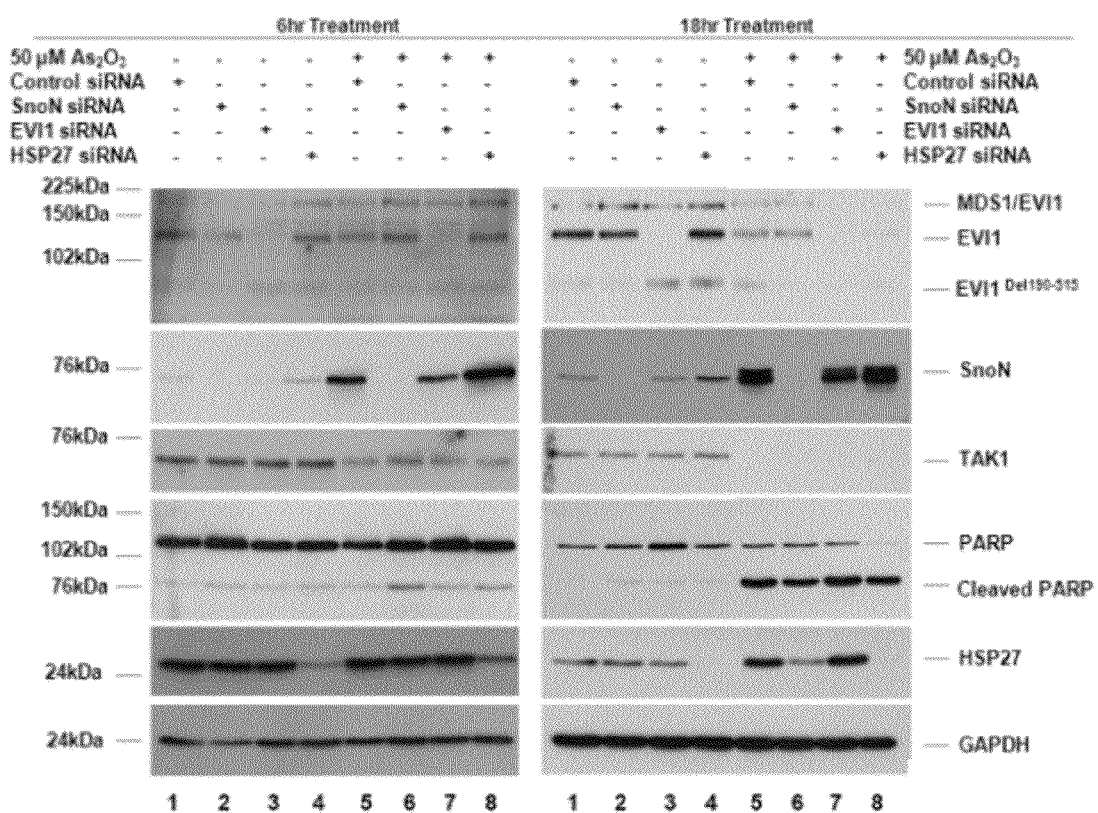
FIG. 35 is a Western blot showing knockdown of SnoN modulates the sensitivity of ovarian cancer cells to arsenic trioxide. HEY cells were seeded at 250,000 cells per 6-well for 24 hours, followed by transient transfection with non-targeting (control) siRNA, SnoN siRNA, EVI1 siRNA, and HSP27 siRNA. Cells were treated with As$_2$O$_3$ 24 hours post-transfection, for either 6 hours (left) or 18 hours (right). Cell lysates were harvested and western analysis was performed.
Figure 36:
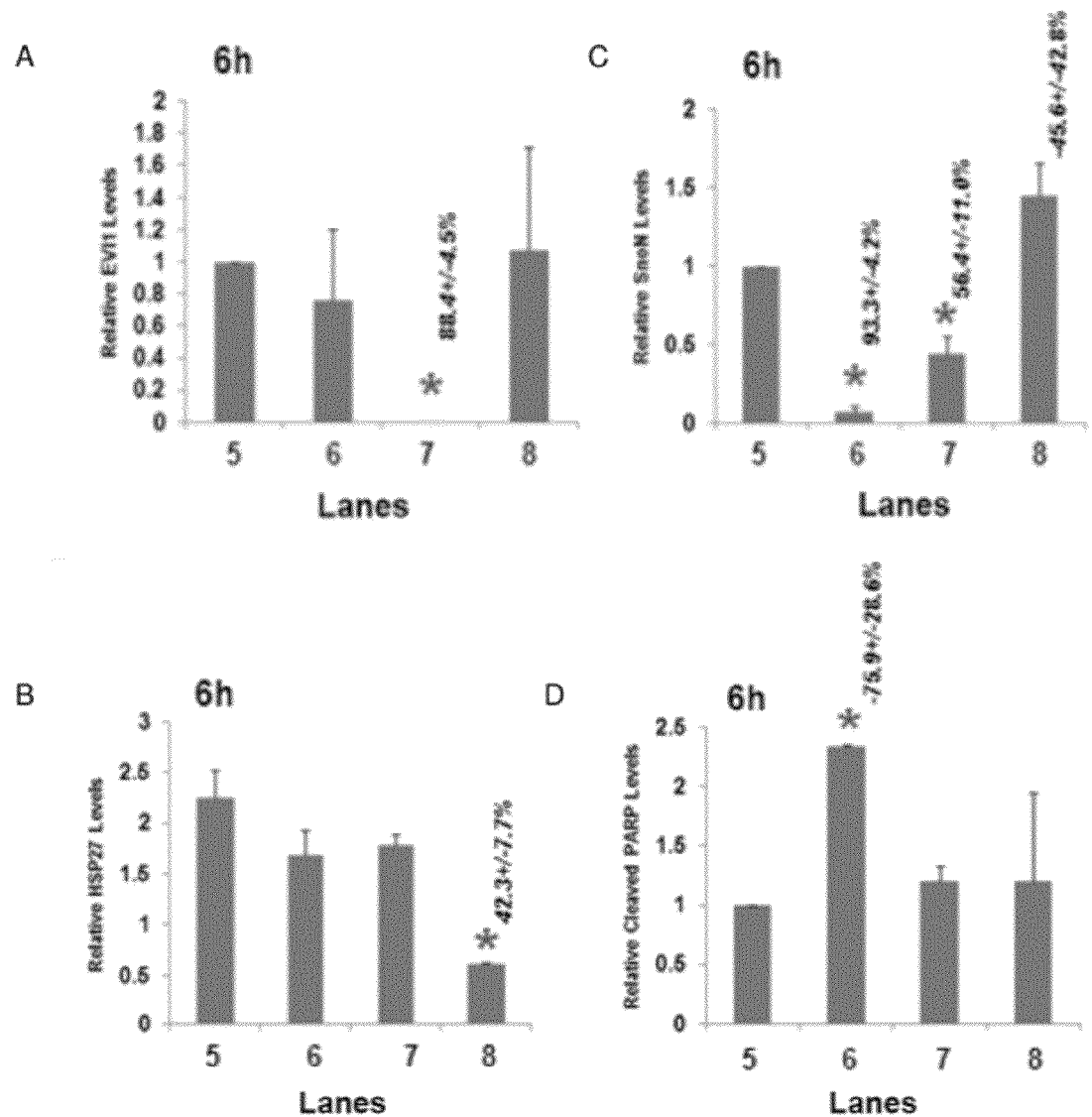
FIGS. 36(A) through (D) are graphs showing densitometric analyses of selected 6-hour treated data presented in FIG. 35. Samples displayed are arsenic trioxide treated samples only (lanes 5-8 by western analysis) for (A) EVI1, (B) HSP27, (C) SnoN, and (D) cleaved PARP.
Figure 37:
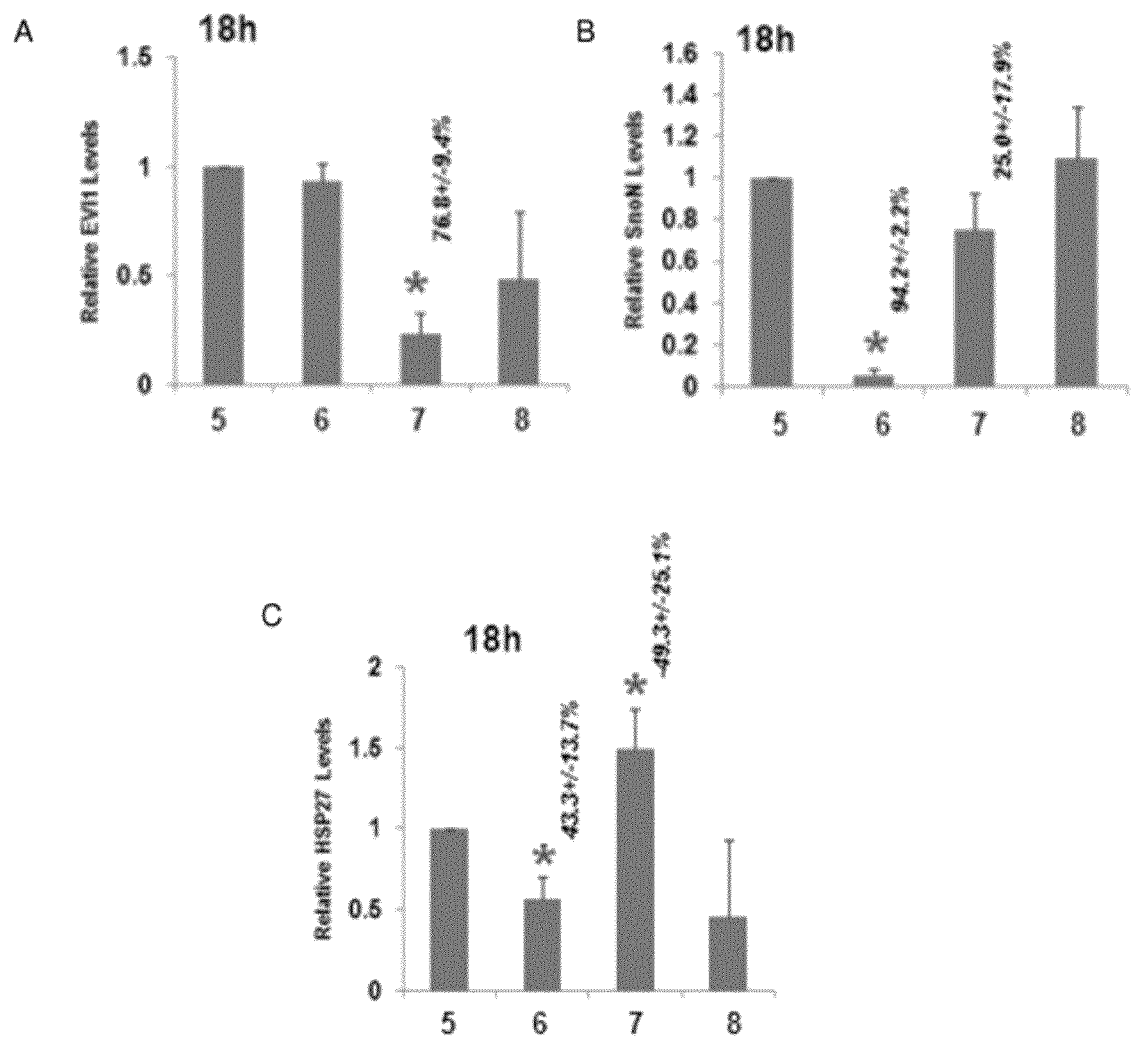
FIGS. 37(A) through (C) are graphs showing densitometric analyses of selected 6-hour treated data presented in FIG. 35. Samples displayed are arsenic trioxide treated samples only (lanes 5-8 by western analysis) for (A) EVI1, (B) SnoN, and (C) HSP27.
Figure 38:
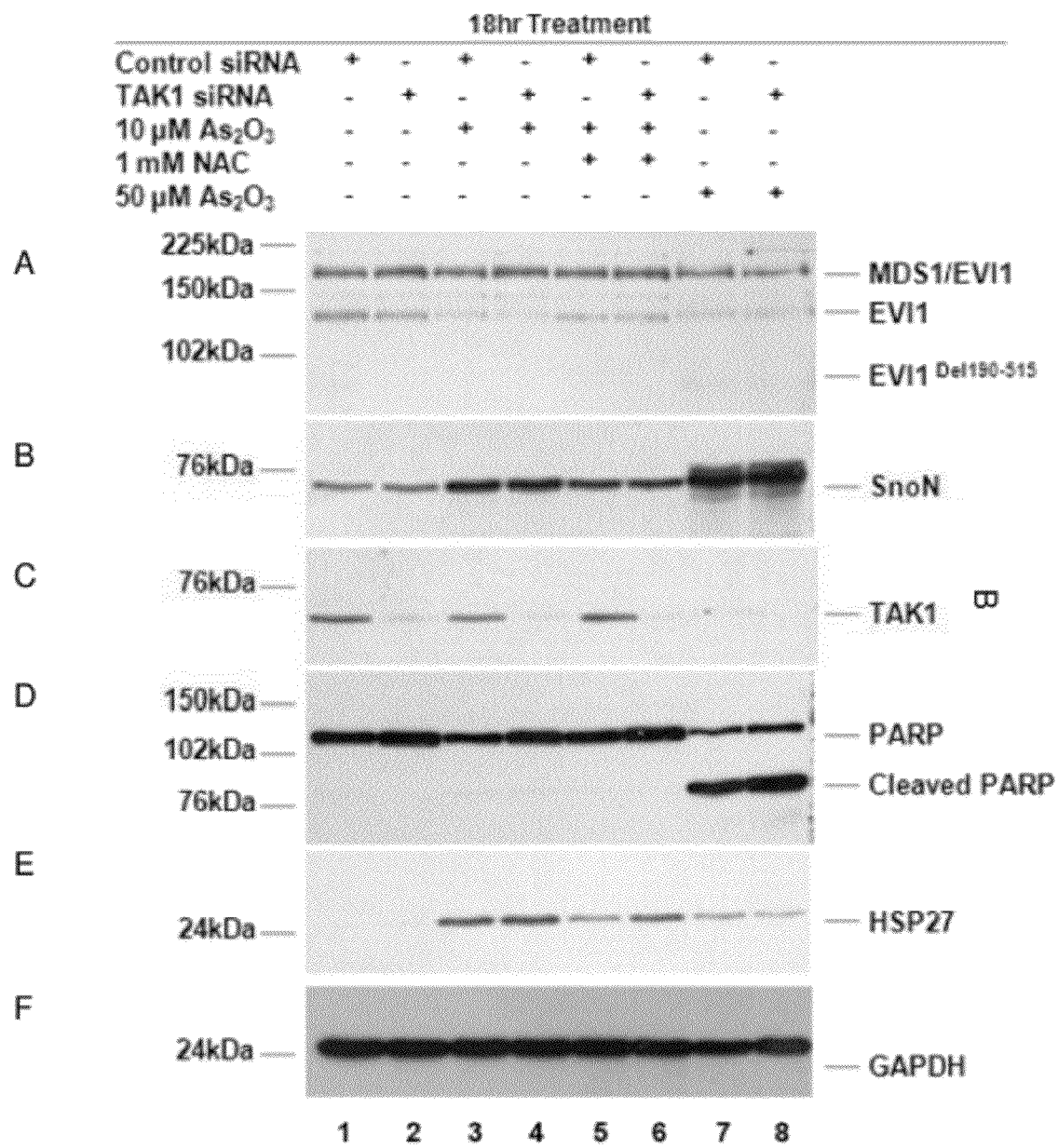
FIGS. 38(A) through (G) show AKT knockdown modulates apoptosis in response to arsenic trioxide. HEY cells were seeded at 375,000 cells per 6-well for 24 hours, followed by transient transfection with non-targeting (control) siRNA or TAK1 siRNA. Cells were then treated with As$_2$O$_3$ and/or NAC 18 hours later. Cell lysates were harvested and western analysis was performed for (A) MDS1/EVI1; (B) SnoN; (C) TAK1; (D) PARP; (E) HSP27; and (F) GAPDH. (G) Densitometric analyses of selected data are collected for TAK1 (Lane 1-8).
Figure 38:
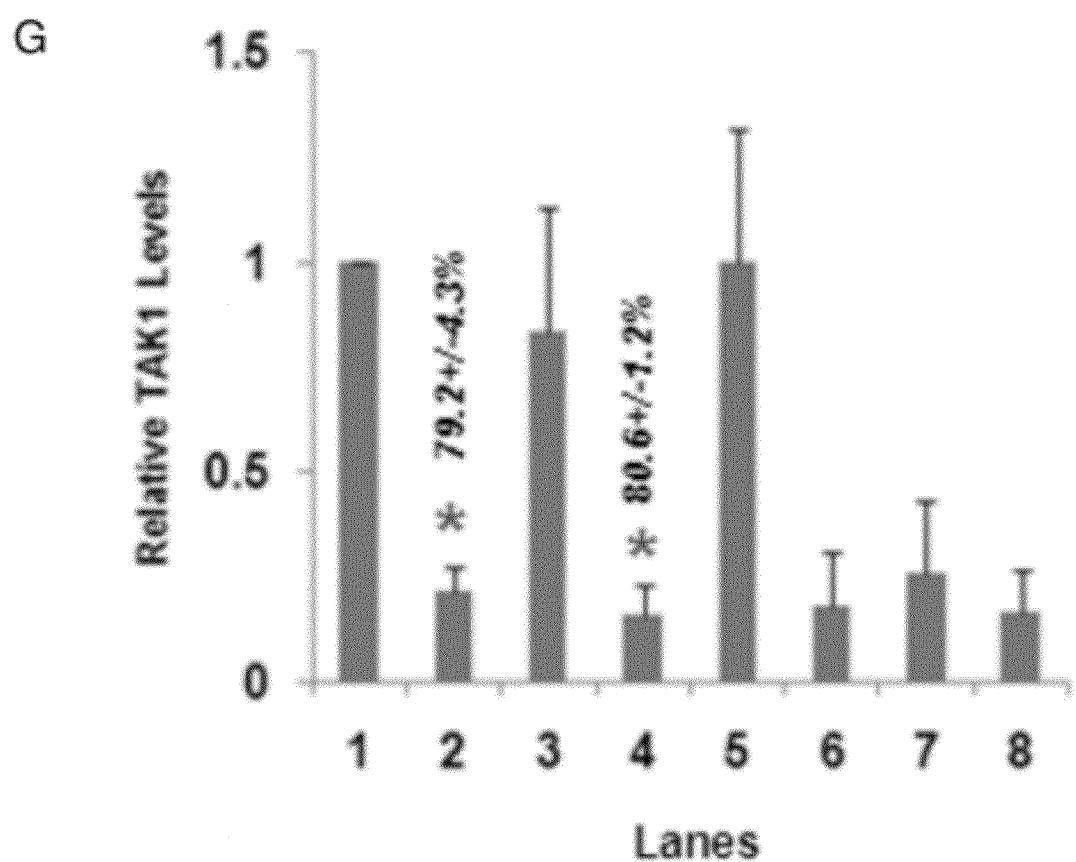

Knockdown of SnoN reproducibly decreased HSP27 levels (by >90%) with 18 hour $As_2O_3$ (50 μM) treatment suggesting that HSP27 may elicit its effects downstream to SnoN, seen in FIGS. 35 through 37. In addition, EVI1 siRNA treated cells had markedly reduced SnoN levels (>50%) both in the absence and presence of $As_2O_3$ (6 and 18 h hours, 50 μM), seen in FIGS. 35 through 37, indicating that SnoN/SkiL levels can be regulated by EVI1. Since $As_2O_3$ treatment decreased TAK1 levels and it is reported that SnoN is rapidly degraded upon TGFβ stimulation by TAK1 via the ubiquitin-dependent proteosome pathway (Kajino, et al. 2007. TAK1 MAPK kinase kinase mediates transforming growth factor-beta signaling by targeting SnoN oncoprotein for degradation. J Biol Chem 282, 9475-9481), TAK1 levels were investigated as to whether reducing TAK1 could prevent SnoN-induced degradation. However, TAK1 siRNA treatment (>80% knockdown) did not modulate SnoN levels or alter the sensitivity of ovarian cancer cells to $As_2O_3$ suggesting TAK1-independent mechanisms regulate SnoN expression, seen in FIGS. 38(A) through (G).

Figure 39:
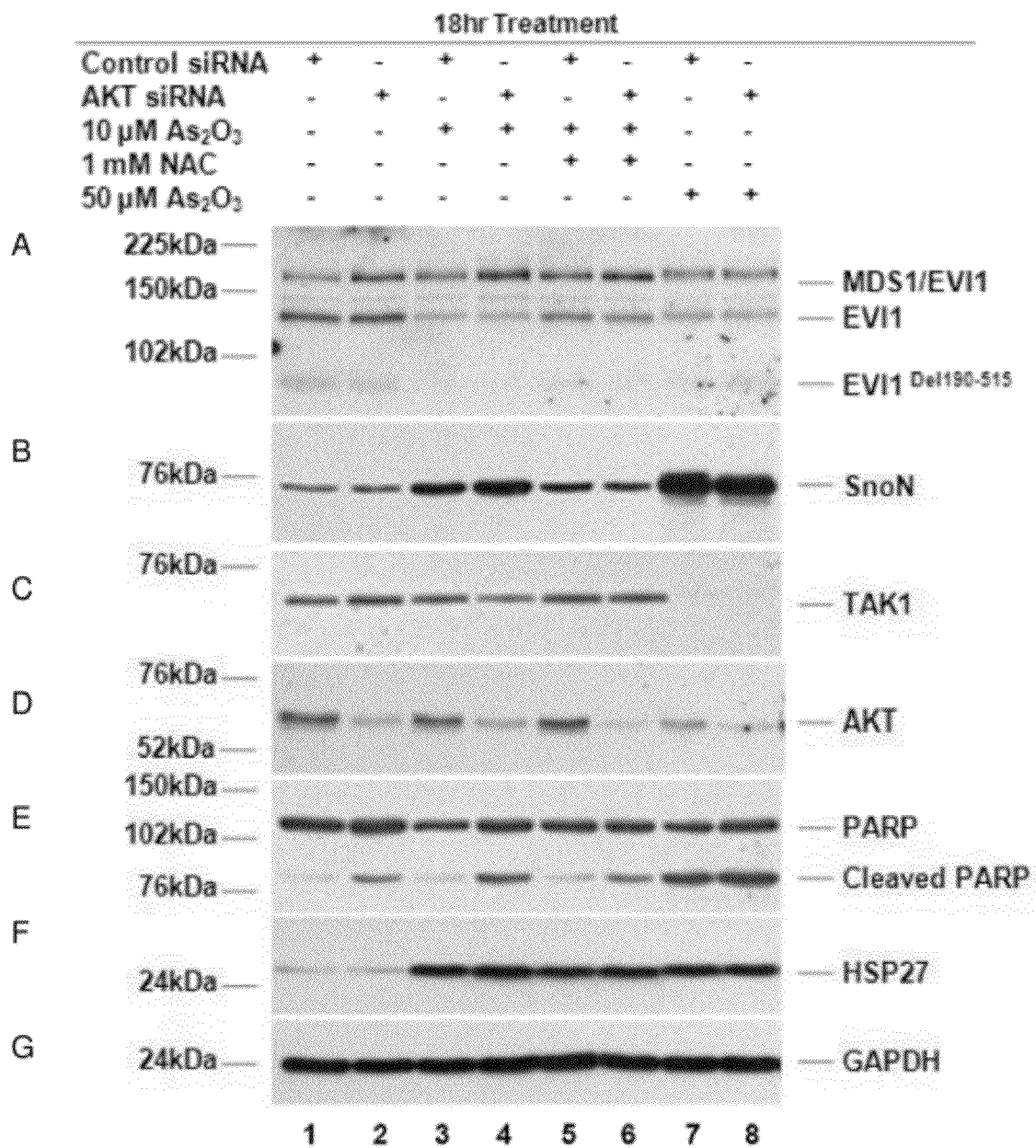
FIGS. 39(A) through (I) show AKT knockdown modulates apoptosis in response to arsenic trioxide. HEY cells were seeded at 375,000 cells per 6-well for 24 hours, followed by transient transfection with non-targeting (control) siRNA or AKT siRNA. Cells were then treated with As$_2$O$_3$ and/or NAC 18 hours later. Cell lysates were harvested and western analysis was performed for (A) MDS1/EVI1; (B) SnoN; (C) TAK1; (D) AKT; (E) PARP; (F) HSP27; and (G) GAPDH. (H) Densitometric analyses of selected data are collected for (H) TAK1 and (I) PARP (Lane 1-8).
Figure 39:
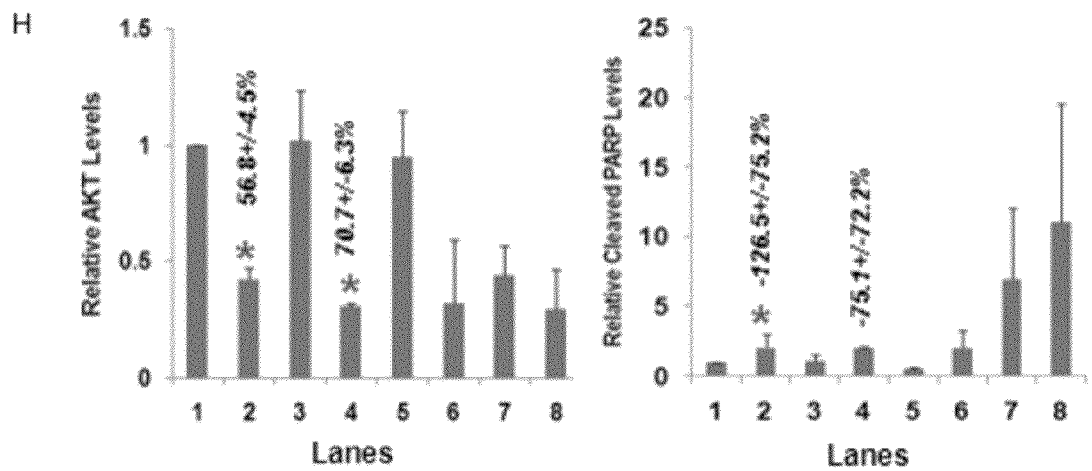

PI3K, which activates AKT (Bellacosa, et al. 1995. Molecular alterations of the AKT2 oncogene in ovarian and breast carcinomas. Int J Cancer 64, 280-285), which is a promising target for therapy in ovarian cancer and is amplified at chromosome 3q26.2 in close proximity to EVI1 in ovarian carcinomas (Shayesteh, et al. 1999. PIK3CA is implicated as an oncogene in ovarian cancer. Nat Genet 21, 99-102; Meng, et al. 2006. Role of PI3K and AKT specific isoforms in ovarian cancer cell migration, invasion and proliferation through the p70S6K1 pathway. Cell Signal 18, 2262-2271). In myeloid leukemia cells, the PI3K/AKT inhibitor, LY294002, increases the apoptotic potential of $As_2O_3$ via modulation of ROS and increasing HSP27 expression (Ramos, et al. 2005. Pharmacologic inhibitors of PI3K/Akt potentiate the apoptotic action of the antileukemic drug arsenic trioxide via glutathione depletion and increased peroxide accumulation in myeloid leukemia cells. Blood 105, 4013-4020). Although AKT siRNA did increase PARP cleavage, seen in FIG. 39(E), it did not alter HSP27 levels suggesting an alternative mechanism in ovarian cells, seen in FIGS. 39(A) through (I).

SnoN RNA and protein levels are elevated with a greater frequency and to a greater degree than are DNA levels in ovarian cancers. PIK3CA, which resides in the 3q26 amplicon, and other processes have been demonstrated to result in frequent activation of the PI3K pathway in ovarian cancer. The regulation of the SnoN levels by signaling through the PI3K pathway suggests that activation of the pathway could cooperate with genomic amplification of SnoN to increase SnoN protein levels. The localization of both PIK3CA and SnoN to the 3q26 amplicon may represent a case of "cooperative" oncogenesis. Greater than 75% of ovarian carcinomas are resistant to the growth inhibitory and pro-apoptotic effects of TGF-β, which may be a critical event in the pathogenesis of this disease. It has been reported that the TGF-β or other signaling components (i.e. SMAD2) may be mutated or altered in ovarian cancer potentially explaining the resistance to TGF-β (Baldwin et al., 2003. Loss of c-myc repression coincides with ovarian cancer resistance to transforming growth factor beta growth arrest independent of transforming growth factor beta/Smad signaling. Cancer Res. 63, 1413-1419). However, these mutations or alterations account for only a minority of TGF-β-resistant ovarian carcinomas indicative of other potential alterations responsible for the observed resistance to TGF-β.

Since successful treatment of cancer cells with chemotherapeutic drugs is dependent on their ability to trigger cell death, it is critical to understand their mechanisms of action. $As_2O_3$ can induce apoptosis in various cells via mechanisms that are presently unclear. A previous study using RNA protection of established primary ovarian epithelial cells and ovarian cancer cell lines failed to detect differences in mRNA levels for SnoN or in TGF-β induced degradation of SnoN (Baldwin et al., 2003. Loss of c-myc repression coincides with ovarian cancer resistance to transforming growth factor beta growth arrest independent of transforming growth factor beta/Smad signaling. Cancer Res. 63, 1413-1419). However, the data presented demonstrate an increase in DNA copy number and elevated RNA levels for SnoN assessed immediately ex vivo by qPCR suggests that in the in vivo tumor environment, SnoN levels are indeed markedly elevated in ovarian cancer. TGF-β induces a rapid loss of SnoN in immortalized normal epithelium followed by a rapid return to normal levels. The striking effects of altering SnoN expression on the behavior of TIOSE suggest that the amplification and increased expression of SnoN plays a major role in ovarian tumorigenesis. Previous data indicates that differential expression of SnoN or SkiL does not appear to account for resistance to TGF-β in ovarian cancer as they found that basal expression levels in normal and malignant ovarian primary cell cultures were similar and moreover, the same rate and amount of SnoN degradation was observed after TGF-β treatment (Baldwin et al., 2003. Loss of c-myc repression coincides with ovarian cancer resistance to transforming growth factor beta growth arrest independent of transforming growth factor beta/Smad signaling. Cancer Res. 63, 1413-1419).

Further, $As_2O_3$, commonly used to treat APL, can target TGFβ signaling mediators via proteosome-dependent (i.e. EVI1 and TGFβRII) and -independent pathways (SMAD2/3 and AKT) in ovarian cancer cell lines. Although low (T80) and high (SKOV3 and HEY) expressing EVI1 ovarian cell lines differed in their response to the apoptotic effects of $As_2O_3$, knockdown of EVI1 (siRNA designed against Exon VII) failed to alter the sensitivity to arsenic trioxide induced apoptosis. There are numerous factors likely dictating cellular resistance or sensitivity to arsenic trioxide including (1) GSH levels, (2) enzymes involved in biosynthesis of GSH, (3) enzymes using GSH (glutathione-S-transferase), (4) free radical scavenging and peroxide metabolism (GSH peroxidase, catalase), and (5) MRP1 levels which is involved in the efflux of $As_2O_3$ in drug-resistant cell lines. Indeed, MRP1 is highly expressed in SKOV3 cells, an $As_2O_3$ resistant cell line. Interestingly, knockdown of EVI1 decreased SnoN protein in both steady-state and $As_2O_3$-treated cells which supports a previous report in murine cells that SnoN is a target of EVI1 (Yatsula, et al. 2005. Identification of binding sites of EVI1 in mammalian cells. J Biol Chem 280, 30712-30722).

Oxidative stress generates ROS which can induce autophagy. Since ROS oxidizes cellular lipids, proteins, and DNA which cellular damage, autophagy serves to prevent accumulation of these damaged toxic products and organelles by sequestering these cellular components into autophagosomes (double membraned vesicles) which fuse with lysosomes for degradation. Specifically, ROS can oxidize the cysteine protease, ATG4, which is involved in initiating the conjugation of LC3-I to autophagosomal membranes and its consequent release from the autophagore membrane (Scherz-Shouval, et al. 2007. Oxidation as a post-translational modification that regulates autophagy. Autophagy 3, 371-373). Superoxide anion appears to be the major reactive oxygen species regulating autophagic process (Chen, et al. 2009. Superoxide is the major reactive oxygen species regulating autophagy. Cell death and differentiation 16, 1040-1052). Signaling pathways determining whether cells undergo autophagy or apoptosis are complex. In malignant glioma cells, $As_2O_3$ appears to initiate an autophagic response that leads to cell death (Kanzawa, et al. 2003. Induction of autophagic cell death in malignant glioma cells by arsenic trioxide. Cancer Res 63, 2103-2108). This contrasts data in ovarian cell lines based on inhibitor studies with 3-MA and zVAD-fmk suggesting cell-type specific effects of $As_2O_3$. Indeed, autophagy has been described as a "double edged sword" promoting (1) survival in response to stress and starvation as well as (2) programmed cell death (Rubinsztein, et al. 2009. In search of an "autophagomometer". Autophagy 5, 585-589).

Figure 27:
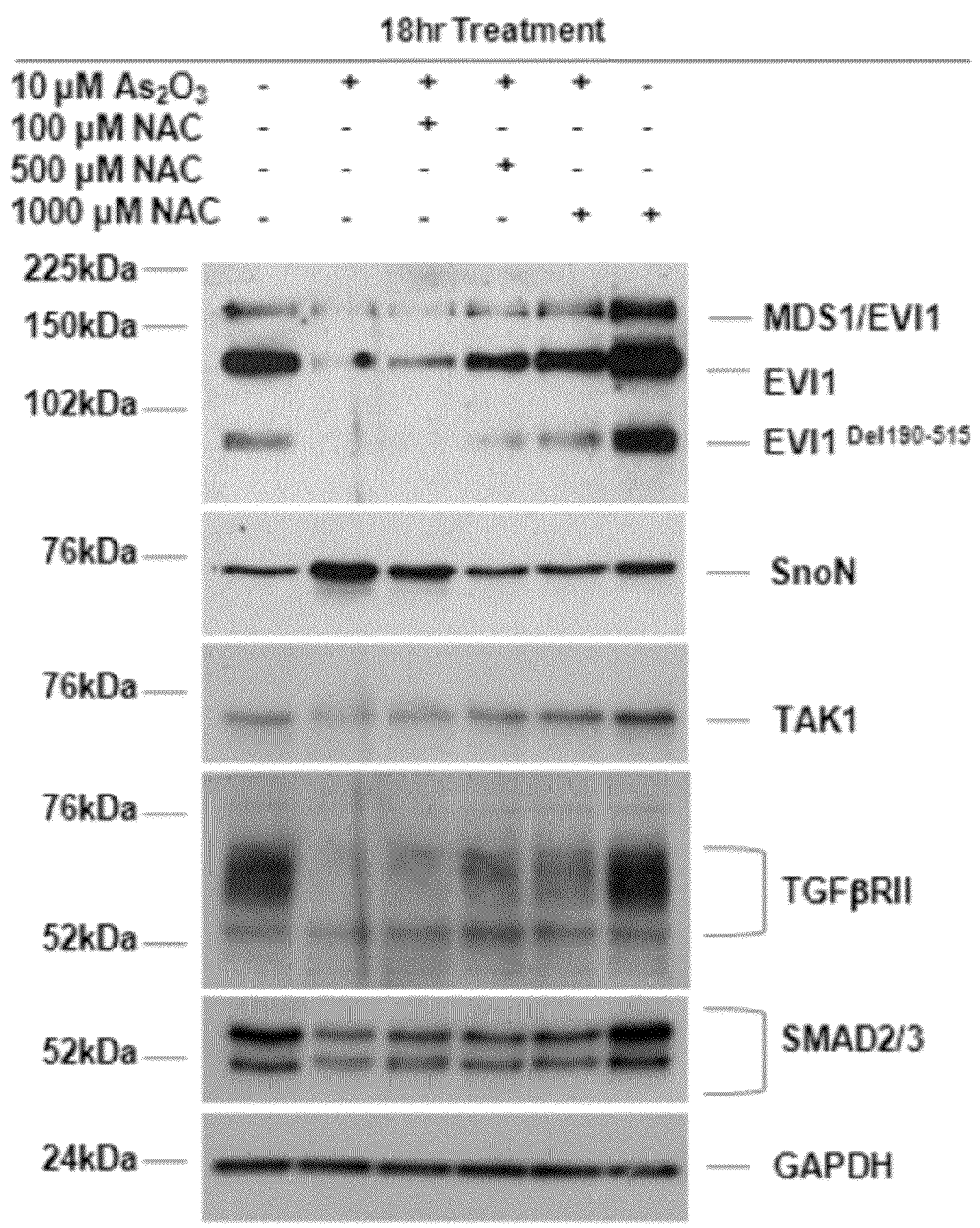
FIG. 27 is a Western blot showing arsenic trioxide mediates its effects on expression of TGFβ signaling mediators by generating reactive oxygen species. HEY cells were seeded at 250,000 cells per 6-well for 24 hours. Cells were treated with As$_2$O$_3$ and/or varying amounts of NAC for 18 hours, followed by Western analysis.

Strikingly, $As_2O_3$ treatment dramatically elevated SnoN levels mediated through a ROS-dependent and TAK1-independent pathway, seen in FIG. 27. SnoN protein not only paralleled LC3-II (an autophagy marker) but knockdown of SnoN altered LC3-II/I ratios. This suggests that LC3-II lies downstream to SnoN. SnoN also modulated HSP27 levels, an "anti-apoptotic" factor. Other mediators important in $As_2O_3$-induced programmed cell death includes p21 which itself leads to cell cycle arrest and apoptosis (Liu & Huang. 2008 Inhibitory role of TGIF in the As2O3-regulated p21 WAF1/CIP1 expression. Journal of biomedical science 15, 333-342). Indeed, it has been previously shown that SnoN knockdown increases p21 protein levels (Nanjundan, et al. 2007. Overexpression of SnoN/SkiL, amplified at the 3q26.2 locus, in ovarian cancers: A role in ovarian pathogenesis. Molecular Oncology 2). Nonetheless, SnoN plays a key role in autophagy by regulating LC3-II levels as a cell survival mechanism to protect against $As_2O_3$ induced apoptosis.

In contrast to immortalized normal ovarian epithelial cells, SnoN levels in ovarian carcinoma cell lines (OVCAR8, OVCA429, SKOV3 and HEY cells) did not appear to undergo degradation with 1 h following TGF-β stimulation, which may account for the resistance to TGF-β-mediated growth arrest, but instead increased 3-6 h following treatment with TGF-β. Combined with the observation that SnoN alters TGF-β induced activation of the PAI-1 promoter, aspects of the TGF-β signaling cascade remain intact in ovarian cancer (i.e. both EVI1 and DACH1 inhibited TGF-β signaling, a dominant negative DACH1 partially restored signaling in ovarian cancer cell lines resistant to TGF-β) (Sunde et al., 2006. Expression profiling identifies altered expression of genes that contribute to the inhibition of transforming growth factor-{beta} signaling in ovarian cancer. Cancer Res. 66, 8404-8412). During cancer progression, when epithelial cells become resistant to the growth inhibitory effects of TGF-β, the cells become increasingly more sensitive to TGF-β responses to EMT and metastasis (Elliott and Blobe, 2005. Role of transforming growth factor Beta in human cancer. J. Clin. Oncol. 23, 2078-2093). Thus, it is likely that cancers which have an intact TGF-β-pathway (i.e. able to promote SnoN-mediated degradation) may be more aggressive than those with a defective pathway (i.e. increased SnoN). This is supported by a recent report where colorectal carcinoma patients with advanced stage tumors had decreased expression of SnoN levels which correlated with poor patient outcome (Chia et al., 2006. SnoN expression is differently regulated in microsatellite unstable compared with microsatellite stable colorectal cancers. BMC Cancer 6, 252).

Reduction of SnoN levels with siRNA in both TIOSE and ovarian carcinoma cell lines decreased cell growth by 20-50% concurrent with increased p21 levels. PAI-1 levels were reduced in SnoN knockdown cells. PAI-1 has been reported to be significantly overexpressed and correlated with an unfavorable prognosis in ovarian cancer (Kuhn et al., 1999. Prognostic significance of urokinase (uPA) and its inhibitor PAI-1 for survival in advanced ovarian carcinoma stage FIGO IIIc. Br. J. Cancer 79, 1746-1751). PAI-1 not only has been shown to be a marker of senescence (Chen, 2000. Replicative senescence and oxidant-induced premature senescence. Beyond the control of cell cycle checkpoints. Ann. N.Y. Acad. Sci. 908, 111-125) but also is involved in increasing the migratory and invasive potential of TGF-β activated cells (Kutz et al., 2001. TGF-β1-induced PAI-1 gene expression requires MEK activity and cell-to-substrate adhesion. J. Cell Sci. 114, 3905-3914). Thus, induction of PAI-1 may, in addition to inducing replicative senescence, also contribute to TGF-β-independent effects of SnoN on cellular motility. Collectively, these results may indicate that SnoN, perhaps in cooperation with other amplified genes, is required to affect cellular migration.

Surprisingly, stable expression of SnoN in an TAg/hTert immortalized ovarian surface epithelial cell line did not stimulate proliferation but rather provoked senescence reversing cellular immortalization by hTert, which was accompanied by upregulation of p21, cyclin D1, PAI-1, p-ERK signaling in combination with a reduction in pRb and reduced p-AKT signaling independently of p53. Similar to the effects of SMURF2, a TGF-β-induced E3 ubiquitin ligase, on senescence (Zhang and Cohen, 2004. Smurf2 upregulation activates telomere-dependent senescence. Genes Dev. 18, 3028-3040), SnoN is able to bypass cellular immortalization induced by hTert. Given the TGF-β-induced targeting of SnoN by SMURF2, these two processes may be linked. Further, the induction of PAI-1 may contribute to the induction of senescence (Chen, 2000. Replicative senescence and oxidant-induced premature senescence. Beyond the control of cell cycle checkpoints. Ann. N.Y. Acad. Sci. 908, 111-125). The ability of SnoN to promote growth arrest and senescence is in contrast to its oncogenic role in several cell lines (Zhu et al., 2005. Requirement for the SnoN oncoprotein in transforming growth factor beta-induced oncogenic transformation of fibroblast cells. Mol. Cell. Biol. 25, 10731-10744), where, with the exception of lung epithelial cells, it has been reported to act as a tumor suppressor (Sarker et al., 2005. SnoN is a cell type specific mediator of transforming growth factor-beta responses. J. Biol. Chem. 280, 13037-13046). Multiple oncogenes that increase the aggressiveness of cancer cell lines have been reported to induce senescence in normal epithelium including ERBB2 (Trost et al., 2005. Premature senescence is a primary fail-safe mechanism of ERBB2-driven tumorigenesis in breast carcinoma cells. Cancer Res. 65, 840-849), RAS (Braig and Schmitt, 2006. Oncogene-induced senescence: putting the brakes on tumor development. Cancer Res. 66, 2881-2884) and BRAF (Michaloglou et al., 2005. BRAFE600-associated senescence-like cell cycle arrest of human naevi. Nature 436, 720-724). Indeed, BRAF mutations are extremely frequent in normal nevi; however, these nevi remain in replicative senescence for decades and rarely progress to melanomas (Michaloglou et al., 2005. BRAFE600-associated senescence-like cell cycle arrest of human naevi. Nature 436, 720-724), indicating the importance of oncogene-induced senescence. Further, overexpression of oncogenic ERBB2 in breast cancer cells can provoke premature senescence accompanied by upregulation of p21 (Trost et al., 2005. Premature senescence is a primary fail-safe mechanism of ERBB2-driven tumorigenesis in breast carcinoma cells. Cancer Res. 65, 840-849). Although expression of SnoN induced p21, this did not appear to be required for the growth inhibition and senescence induced by SnoN as siRNA to PML markedly decreased p21 levels but did not restore proliferative potential.

The frequent and high-level increase in SnoN DNA and RNA levels in ovarian cancer suggests that during tumor progression, SnoN acquires tumor-promoting activity. Compatible with these observations, as noted above, SnoN has been proposed to have both tumor promoting and inhibiting activity dependent on the cellular context. These observations are similar to those reported for the role of TGF-β in tumorigenesis. TGF-β exhibits dual effects during carcinogenesis where in early stages of tumor development, it acts as a tumor suppressor inhibiting cell growth and inducing apoptosis, whereas in later stages of tumorigenesis, it promotes metastasis (Elliott and Blobe, 2005. Role of transforming growth factor Beta in human cancer. J. Clin. Oncol. 23, 2078-2093). Thus, depending on the cell context and wiring of the TGF-β signaling pathway, the activities of SnoN/SkiL may either promote transformation or tumor suppression. Clearly, TGF-β function is aberrant in ovarian cancer and SnoN, from data presented herein, is dysregulated in ovarian cancers. Thus, SnoN may contribute to aberrant TGF-β signaling and thus, lead to altered functional outcomes.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of compositions and methods for treatment of cancer, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of identifying a tumor comprising:
   obtaining baseline levels of at least one cellular characteristic in a non-tumorous cell line, wherein the at least one cellular characteristic is SnoN mRNA expression levels;
   obtaining the levels of the at least one cellular characteristic in at least one test cell;
   comparing the levels of the at least one cellular characteristic in the at least one test cell to the least one cellular characteristic in a non-tumorous cell line;
      wherein the levels are compared using the formula Ct of gene—Ct of β-actin; and
   analyzing the levels of the at least one cellular characteristic for elevations in the levels of the at least one cellular characteristic;
   wherein an elevation in SnoN mRNA expression level in the test cell over the baseline levels is indicative of a tumor.

2. The method of claim 1, wherein the test cell is a sample taken from a patient suspected of having ovarian cancer.

3. The method of claim 1, further comprising
   inducing a change in SnoN mRNA expression level by exposing the at least one test cell to TGF-β or $As_2O_3$ prior to obtaining the levels of the at least one cellular characteristic; and
   waiting at least 15 minutes and obtaining the changed SnoN mRNA expression level of the at least one test cell;
   wherein an elevation in SnoN mRNA expression level after exposure is indicative of a tumor.

4. The method of claim 3, wherein the at least one test cell is exposed to TGF-β for a time selected from the group consisting of 15 minutes to 3 hours; 1 hour; and 3 hours.

5. The method of claim 3, wherein the at least one test cell is exposed to $As_2O_3$; for a time selected from the group consisting of 3 hours to 9 hours, and 6 hours.

6. A method of identifying a tumor comprising:
   obtaining a baseline level of SnoN mRNA expression levels in at least one test cell;
   inducing a change in SnoN mRNA expression level by exposing the at least one test cell to TGF-β or $As_2O_3$;
   waiting at least 15 minutes and obtaining the changed SnoN mRNA expression level of the at least one test cell; and
   comparing the levels of the baseline SnoN mRNA expression level and the changed SnoN mRNA expression level;
   wherein an elevation in SnoN mRNA expression level after exposure is indicative of a tumor.

7. The method of claim 6, wherein the at least one test cell is exposed to TGF-β for 15 minutes to 3 hours.

8. The method of claim 7, wherein the at least one test cell is exposed to TGF-β for 1 hour.

9. The method of claim 7, wherein the at least one test cell is exposed to TGF-β for 3 hours.

10. The method of claim 6, wherein the at least one test cell is exposed to $As_2O_3$; for 3 hours to 9 hours.

11. The method of claim 6, wherein the at least one test cell is exposed to $As_2O_3$; for 6 hours.

12. The method of claim 6, further comprising
    comparing the levels of the at least one cellular characteristic in the at least one test cell to the least one cellular characteristic in a non-tumorous cell line;
    wherein the levels are compared using the formula Ct of gene—Ct of β-actin.

* * * * *